United States Patent
Boulares et al.

(10) Patent No.: US 11,723,906 B2
(45) Date of Patent: Aug. 15, 2023

(54) PARP-1 AND METHODS OF USE THEREOF

(71) Applicant: The Board of Supervisors of Louisiana State University and Agricultural and Mechanical College, Baton Rouge, LA (US)

(72) Inventors: Hamid Boulares, New Orleans, LA (US); Mohamed Ghonim, New Orleans, LA (US); Amir Al-Khami, New Orleans, LA (US); Augusto Ochoa, New Orleans, LA (US)

(73) Assignee: The Board of Supervisors of Louisiana State University and Agricultural and Mechanical College, Baton Rouge, LA (US)

( * ) Notice: Subject to any disclaimer, the term of this patent is extended or adjusted under 35 U.S.C. 154(b) by 0 days.

(21) Appl. No.: 16/564,735

(22) Filed: Sep. 9, 2019

(65) Prior Publication Data
US 2020/0069682 A1 Mar. 5, 2020

Related U.S. Application Data

(63) Continuation-in-part of application No. PCT/US2018/021855, filed on Mar. 9, 2018.

(60) Provisional application No. 62/469,436, filed on Mar. 9, 2017.

(51) Int. Cl.
*A61K 31/498* (2006.01)
*C07K 16/28* (2006.01)
*A61P 35/00* (2006.01)

(52) U.S. Cl.
CPC ........ *A61K 31/498* (2013.01); *C07K 16/2818* (2013.01); *A61P 35/00* (2018.01)

(58) Field of Classification Search
CPC .............................. A61K 31/498; A61P 35/00
See application file for complete search history.

(56) References Cited

U.S. PATENT DOCUMENTS

| | | | | |
|---|---|---|---|---|
| 8,894,989 B2 * | 11/2014 | Xu | ............................ | A61P 35/02 424/85.2 |
| 8,912,187 B2 * | 12/2014 | Martin | ...................... | A61P 31/20 514/248 |
| 2005/0143370 A1 | 6/2005 | Helleday et al. | | |
| 2006/0142231 A1 | 6/2006 | Ashworth et al. | | |
| 2008/0058325 A1 | 3/2008 | Kalish et al. | | |
| 2013/0209517 A1 | 8/2013 | Akle et al. | | |
| 2015/0283237 A1 * | 10/2015 | Felder | ................. | A61K 31/7068 424/142.1 |

FOREIGN PATENT DOCUMENTS

| | | |
|---|---|---|
| WO | 2016/087994 | 6/2016 |
| WO | 2017/032289 | 3/2017 |

OTHER PUBLICATIONS

Kerbel et al. Nature Reviews, Jun. 2004, vol. 4, pp. 423-436 (Year: 2004).*
Lien et al. European Journal of Cancer, 2013, vol. 49, pp. 3387-3395 (Year: 2013).*
Maraveyas et al. British Journal of Cancer, 2005, vol. 92, pp. 1588-1590 (Year: 2005).*
Lynparza® (olaparib) Prescribing Information, 25 pages, Revised Aug. 2017 (Year: 2017).*
Jiao et al. Clin. Cancer Res., 2017, vol. 23, No. 14, pp. 3711-3720 (Published online Feb. 6, 2017) (Year: 2017).*
Higuchi et al. Cancer Immunol. Res., 2015, vol. 3, No. 11, pp. 1257-1268 (Year: 2015).*
Lynparza Prescribing Information (https://www.accessdata.fda.gov/drugsatfda_docs/label/2017/206162s003lbl.pdf; Revised Jan. 2017; 16 pages) (Year: 2017).*
Chen et al. Invest. New Drugs, 2016, vol. 34, pp. 450-457 (Year: 2016).*
Tang et al. Molecular Pharmacology, 2012, vol. 82, No. 2, pp. 322-332 (Year: 2012).*
Senra et al. Molecular Cancer Therapeutics, Oct. 2011, vol. 10, No. 10, pp. 1949-1958 (Year: 2011).*
Menear et al. J. Med. Chem., 2008, vol. 51, pp. 6581-6591 (Year: 2008).*
Zerfaoui M et al., Poly(ADP-ribose) polymerase-1 is a determining factor in Crm1-mediated nuclear export and retention of p65 NF-kappa B upon TLR4 stimulation. J. Immunol 185, 1894-1902 (2010).
Zingarelli, Basilia, Andrew L. Salzman, and Csaba Szabó. "Genetic disruption of poly (ADP-ribose) synthetase inhibits the expression of P-selectin and intercellular adhesion molecule-1 in myocardial ischemia/reperfusion injury" Circulation research 83.1 (1998): 85-94. v.
Kinzler K W. Lessons from hereditary colorectal cancer. Cell. 1996; 87:159-170.
Larmonier CB, et al., Transcriptional Reprogramming and Resistance to Colonic Mucosal Injury in Poly(ADP-ribose) Polymerase 1 (PARP1)-deficient Mice. J. Biol Chem 291, 8918-8930 (2016).
Lee J M, et al. Safety and clinical activity of the programmed death-ligand 1 inhibitor durvalumab in combination with poly (adp-ribose) polymerase inhibitor olaparib or vascular endothelial growth factor receptor 1-3 inhibitor cediranib in women's cancers: A dose-escalation, phase I study. J Clin Oncol. 2017; 35:2193-2202.
Leichman L et al., Phase II Study of Olaparib (AZD-2281) After Standard Systemic Therapies for Disseminated Colorectal Cancer. Oncologist 21, 172-177 (2016).
Lieberman, H.A. and Lachman, L., Eds., Pharmaceutical Dosage Forms: Tablets, Marcel Decker, New York, N.Y., 1989.
Luo, Xin, and W. Lee Kraus. "On PAR with PARP: cellular stress signaling through poly (ADP-ribose) and PARP-1." Genes & development 26.5 (2012): 417-432.

(Continued)

*Primary Examiner* — James D. Anderson
(74) *Attorney, Agent, or Firm* — Baker Donelson

(57) ABSTRACT

The invention is directed to roles for PARP-1 in disease.

8 Claims, 58 Drawing Sheets
(52 of 58 Drawing Sheet(s) Filed in Color)
Specification includes a Sequence Listing.

(56) References Cited

OTHER PUBLICATIONS

Marchetti A, et al. Why anti-PD1/PDL1 therapy is so effective? Another piece in the puzzle. J. Thorac Dis 9, 4863-4866 (2017).
Martinez-Zamudio R, HA HC. Histone ADP-ribosylation facilitates gene transcription by directly remodeling nucleosomes Mol Cell Biol. Jul. 2012;32(13):2490-502.
Martínez-Zamudio, Ricardo Iván, and Hyo Chol Ha. "PARP 1 enhances inflammatory cytokine expression by alteration of promoter chromatin structure in microglia." Brain and behavior 4.4 (2014): 552-565.
McClellan J L, et al. Intestinal inflammatory cytokine response in relation to tumorigenesis in the apcmin/+mouse. Cytokind. 2012; 57:113-119.
Mei, Z, et al. Tumour-infiltrating inflammation and prognosis in colorectal cancer: Systematic review and meta-analysis Br J Cancer. 2014; 110:1595-1605.
Mellman, Ira, George Coukos, and Glenn Dranoff. "Cancer immunotherapy comes of age." Nature 480.7378 (2011): 480-489.
Min, Wookee, and Zhao-Qi Wang. "Poly (ADP-ribose) glycohydrolase (PARG) and its therapeutic potential." Front Biosci 14.9 (2009): 1619-1626.
Nambiar P R, GirnunG, Lillo N A, Gude K, Whiteley H E, Rosenberg D W. Preliminary analysis of azoxymethane induced colon tumors in inbred mice commonly used as transgenic/knockout progenitors. Int J Oncol. 2003; 22:145-150.
Naura AS et al., Reciprocal regulation of iNOS and PARP-1 during allergen-induced eosinophilia. Eur Respir J 33, 252-262 (2009).
Nozaki, Tadashige, et al. "Parp-1 deficiency implicated in colon and liver tumorigenesis induced by azoxymethane." Cancer science 94.6 (2003): 497-500.
Oumouna M et al., Poly(ADP-ribose) polymerase-1 inhibition prevents eosinophil recruitment by modulating Th2 cytokines in a murine model of allergic airway inflammation: a potential specific effect on IL-5. J Immunol 177, 6489-6496 (2006).
Oumouna-Benachour K et al., Intrinsic resistance to apoptosis of color epithelial cells is a potential determining factor in the susceptibility of the A/J mouse strain to dimenthylhydrazine-induced colon tumorigenesis. Mol Carcinog 46, 993-1002 (2007).
Oumouna-Benachour K, et al. Poly(adp-ribose) polymerase inhibition reduces atherosclerotic plaque size and promotes factor of plaque stability in apolipoprotein e-deficient mice: Effects on macrophage recruitment, nuclear factor-kappab nuclear translocation, and foam cell death. Circulation. 2007; 115:2442-2450.
Pacher, Pal, and Csaba Szabo. "Role of the peroxynitrite-poly (ADP-ribose) polymerase pathway in human disease." The American journal of pathology 173.1 (2008): 2-13.
Palmai-Pallag, Timea, and Csanád Z. Bachrati. "Inflammation-induced DNA damage and damage-induced inflammation: a vicious cycle." Microbes and infection 16.10 (2014): 822-832.
Pardoll, Drew M. "The blockade of immune checkpoints in cancer immunotherapy." Nature Reviews Cancer 12.4 (2012): 252-264.
Park EM, et al. Interaction between inducible nitric oxide synthase and poly(ADP-ribose) polymerase in focal ischemic brain injury. Stroke. Dec. 2004;35(12):2896-901.
Pereira C, Grácio D, Teixeira JP, Magro F. Oxidative Stress and DNA Damage: Implications in Inflammatory Bowel Disease. Inflamm Bowel Dis. Oct. 2015;21(10):2403-17.
Pommier Y, O'Connor M J, de Bono J. Laying a trap to kill cancer cells: Parp inhibitors and their mechanisms of action. Sci Transl Med. 2016; 8:362ps317.
Powell, Steven M., et al. "APC mutations occur early during colorectal tumorigenesis." Nature 359.6392 (1992): 235-237.
Prendergast, George C., et al. Discovery of IDO1 inhibitors: from bench to bedside. Cancer research 77.24 2017: 6795-6811.
Remington: The Science and Practice of Pharmacy, Nineteenth Ed (Easton, Pa.: Mack Publishing Company, 2000).
Remington's Pharmaceutical Sciences, Mack Publishing Co., Easton, Pa. 1980.

Rosado M M, Bennici E, Novelli F, Pioli C. Beyond DNA repair, the immunological role of parp-1 and its siblings. Immunology. 2013; 139:428-437.
Sceneay J et al., Tracking the fate of adoptively transferred myeloid-derived suppressor cells in the primary breast tumor microenvironment. PLoS One 13, e0196040 (2018).
Schlaeger T M, et al. Uniform vascular-endothelial-cell-specific gene expression in both embryonic and adult transgenic mice. Proc Natl Acad Sci USA. 1997; 94:3058-3063.
Schreiber, Valérie, et al. "Poly (ADP-ribose): novel functions for an old molecule." Nature reviews Molecular cell biology 7.7 (2006): 517-528.
Serebrennikova O B, et al. Tpl2 ablation promotes intestinal inflammation and tumorigenesis in Apc(min) mice by inhibiting il-10 secretion and regulatory t-cell generation. Proc Natl Acad Sci USA. 2012; 109:E1082-1091.
Sethi, Gurupreet S., Vivek Dharwal, and Amarjit S. Naura. "Poly (ADP-ribose) polymerase-1 in lung inflammatory disorders: a review." Frontiers in immunology 8 (2017): 1172.
Sharp, C., et al. "Poly ADP ribose-polymerase inhibitors prevent the upregulation of ICAM-1 and E-selectin in response to Th1 cytokine stimulation." Inflammation 25.3 (2001): 157-163.
Snider AJ et al., Murine Model for Colitis-Associated Cancer of the Colon. Methods Ml Biol 1438, 245-254 (2016).
Swindall, Amanda F., Jennifer A. Stanley, and Eddy S. Yang. "PARP-1: friend or foe of DNA damage and repair in tumorigenesis?." Cancers 5.3 (2013): 943-958.
Tanaka T, Kohno H, Suzuki R, Yamada Y, Sugie S, Mori H. A novel inflammation-related mouse colon carcinogenesis model induced by azoxymethane and dextran sodium sulfate. Cancer science. 2003; 94:965-973.
Tarhuni, Abdelmetalab, et al. "Paradoxical Roles of PARP-1 in Colon Inflammation and Tumorigenesis." Abstract Only. The FASEB Journal 29 (2015): 629-11.
Thevenot P T, et al. The stress-response sensor chop regulates the function and accumulation of myeloid-derived suppressor cells in tumors. Immunity. 2014; 41:389-401.
Thomas, Anish, et al. "Durvalumab in combination with olaparib in patients with relapsed SCLC: results from a phase II study." Journal of Thoracic Oncology 14.8 (2019): 1447-1457.
Thorén, Fredrik B., Ana I. Romero, and Kristoffer Hellstrand. "Oxygen radicals induce poly (ADP-ribose) polymerase-dependent cell death in cytotoxic lymphocytes." The Journal of Immunology 176.12 (2006): 7301-7307.
Ullrich, Oliver, et al. "Regulation of microglial expression of integrins by poly (ADP-ribose) polymerase-1." Nature cell biology 3.12 (2001): 1035-1042.
Velazquez KT et al., Quercetin Supplementation Attenuates the Progression of Cancer Cachexia in Apc(Min/+) Mice. Journal of Nutrition 144, 868-875 (2014).
Von Lukowicz, Tobias, et al. "PARP1 is required for adhesion molecule expression in atherogenesis." Cardiovascular research 78.1 (2008): 158-166.
Wang Z Q, et al. Mice lacking aADPRT and poly(adp-ribosyl)ation develop normally but are susceptible to skin disease. Genes & Development 1995; 9:509-520.
Written Opinion of the International Searching Authority for PCT/US2018/021855, dated Jun. 25, 2018.
Zerfaoui M et al., Effects of PARP-1 deficiency on airway inflammatory cell recruitment in response to LPS or TNF: differential effects on CXCR2 ligands and Duffy Antigen Receptor for Chemokines. J Leukoc Biol 86, 1385-1392 (2009).
Zerfaoui M et al., Nuclear translocation of p65 NF-kappaB is sufficient for VCAM-1, but not ICAM-1, expression in TNF-stimulated smooth muscle cells: Differential requirement for PARP-1 expression and interaction. Cell Signal 20, 186-194 (2008).
Al-Khami A A, et al. Energy metabolic pathways control the fate and function of myeloid immune cells. J Leukoc Biol. 2017; 102:369-380.
Al-Khami, Amir A., et al. "Fueling the mechanisms of asthma: Increased tally acid oxidation in inflammatory immune cells may represent a novel therapeutic target." Clinical & Experimental Allergy 47.9 (2017): 1170-1184.

(56) References Cited

OTHER PUBLICATIONS

Al-Khami, Amir A., et al. "Metabolic reprogramming of myeloid-derived suppressor cells (MDSC) in cancer." Oncoimmunology 5.8 (2016): e1200771.
Aldinucci A, et al. A key role for poly(adp-ribose) polymerase-1 activity during human dendritic cell maturation. J Immunol. 2007; 179:305-312.
Althaus, Felix R., et al. "Poly ADP-ribosylation: a DNA break signal mechanism." Molecular and cellular biochemistry 193.1 (1999): 5-11.
Amé, Jean-Christophe, et al. "The PARP superfamily." Bioessays 26.8 (2004): 882-893.
Aris, Mariana, et al. "Immunomodulatory monoclonal antibodies in combined immunotherapy trials for cutaneous melanoma." Frontiers in immunology 8 (2017): 1024.
Ba, Xueqing, and Nisha Jain Garg. "Signaling mechanism of poly (ADP-ribose) polymerase-1 (PARP-1) in inflammatory diseases." The American journal of pathology 178.3 (2011): 946-955.
Benzekry S et al., Metronomic reloaded: Theoretical models brining chemotherapy into the era of precision medicine. Semin Cancer Biol 35, 53-61 (2015).
Bissahoyo A, et al. Azoxymethane is a genetic background-dependent colorectal tumor initiator and promoter in mice: Effects of dose, route, and diet. Toxicological sciences: an official journal of the Society of toxicology. 2005; 88:340-345.
Boulares A H, et al. Gene knockout or pharmacological inhibition of poly(adp-ribose) polymerase-1 prevents lung inflammation in a murine model of asthma. Am J Respir Cell Mol Biol. 2003; 28:322-329.
Boulares AH, et al. NF-kappaB activation is delayed in mouse L929 cells infected with interferon suppressing, but not inducing, vesicular stomatitis virus strains. Virology 218, 71-80 (1996).
Bronte V et al., Recommendations for myeloid-derived suppressor cell nomenclature and characterization standards. Nat Commun 7, 12150 (2016).
Chacon-Cabrera A et al., Role of PARP activity in lung cancer-induced cachexia: Effects on muscle oxidative stress, proteolysis, anabolic markers, and phenotype. J. Cell Physiol 232, 3744-3761 (2017).
Chen E X, et al. A phase I study of olaparib and irinotecan in patients with colorectal cancer: Canadian cancer trials group ind 187. Invest New Drugs. 2016; 34-450-457.
Chiang, Jasson, et al. "Honokiol protects rats against eccentric exercise-induced skeletal muscle damage by inhibiting NF-?B induced oxidative stress and inflammation." European journal of pharmacology 610.1-3 (2009): 119-127.
Claybon A, et al. PARP1 suppresses homologous recombination events in mice in vivo. Nucleic Acids Res 38, 7538-7545 (2010).
Condamine, Thomas, et al. "Transcriptional regulation of myeloid-derived suppressor cells." Journal of leukocyte biology 98.6 (2015): 913-922.
D'amours D, et al. Poly(ADP-ribosyl)ation reactions in the regulation of nuclear functions. Biochem J. Sep. 1, 1999;342( Pt2)(Pt2):249-68.
Dalgleish AG, et al. The failure of radical treatments to cure cancer: can less deliver more? Ther Adv Vaccines Immunother 6, 69-76 (2018).
Darvin, Pramod, et al. "Immune checkpoint inhibitors: recent progress and potential biomarkers." Experimental & molecular medicine 50.12 (2018): 1-11.
Datta R, et al. Parp-1 deficiency blocks il-5 expression through calpain-dependent degradation of stat-6 in a murine asthma model. Allergy. 2011; 66:853-861.
De Murcia JM et al., Requirement of poly (ADP-ribose) polymerase in recovery from DNA damage in mice and in cells. Proc Natl Acad Sci USA 94, 7303-7307 (1997).
Deslee, Gaetan, et al. "Oxidative damage to nucleic acids in severe emphysema." Chest 135.4 (2009): 965-974.

Diesendruck Y and Benhar I. Novel immune check point inhibiting antibodies in cancer therapy—Opportunities and challenges. Drug Resist Updat. Jan. 2017;30:39-47.
Dorsam B et al., PARP-1 protects against colorectal tumor induction, but promotes inflammation-driven colorectal tumor progression. Proc Natl Acad Sci USA 115, E4061-E4070 (2018).
Errami Y, et al. Icad deficiency in human color cancer and predisposition to colon tumorigenesis: Linkage to apoptosis resistance and genomic instability. PLoS One. 2013; 8:e57871.
Fahs SA, et al. A conditional knockout mouse model reveals endothelial cells as the principal and possibly exclusive source of plasma factor viii. Blood 2014; 123:3706-3713.
Fearnhead, Nicola S., et al. "The abc of ape." Human molecular genetics 10.7 (2001): 721-733.
Fouquerel, Elise, et al. "ARTD1/PARP1 negatively regulates glycolysis by inhibiting hexokinase 1 independent of NAD+ depletion." Cell reports 8.6 (2014): 1819-1831.
Gabrilovich DI, Myeloid-Derived Suppressor Cells. Cancer Immunol Res. 5, 3-8 (2017).
George, Angela, et al. "Delivering widespread BRCA testing and PARP inhibition to patients with ovarian cancer." Nature reviews Clinical oncology 14.5 (2017): 284-296.
Ghonim M A, et al. Parp inhibition by olaparib or gene knockout blocks asthma-like manifestation in mice by modulating cd4(+) t cell function. Journal of translational medicine. 2015; 13:225.
Ghonim M A, et al. Parp is activated in human asthma and it inhibition by olaparib blocks house dust mite-induced disease in mice Clin Sci (Lond). 2015; 129:951-962.
Gounaris E, et al. Mast cells are an essential hematopoietic compontent for polyp development. Proc Natl Acad Sci USA. 2007; 104:19977-19982.
Gourley, Charlie, et al. "Moving from poly (ADP-ribose) polymerase inhibition to targeting DNA repair and DNA damage response in cancer therapy." Journal of Clinical Oncology 37.25 (2019): 2257-2269.
Ha HC, et al. Poly(ADP-ribose) polymerase is a mediator of necrotic cell death by ATP depletion. Proc Natl Acad Sci U S A. Nov. 23, 1999;96(24):13978-82.
Hassa PO and Hottiger MO. The functional role of poly(ADP-ribose)polymerase 1 as novel coactivator of NF-kappaB in inflammatory disorders. Cell Mol Life Sci. Sep. 2002;59(9):1534-53.
Highfill S L, et al. Disruption of exer2-mediated mdse tumor trafficking enhances anti-pd1 efficacy. Science translational medicine. 2014; 6:237ra267.
Hopkins TA et al., PARP1 Trapping by Parp inhibitors drives cytotoxicity in both cancer cells and healthy bone marrow. Mol Cancer Res 17, 409-419 (2019).
Hossain F, et al. Inhibition of fatty acid oxidation modulates immunosuppressive functions of myeloid-derived suppressor cells and enhances cancer therapies. Cancer Immunol Res. 2015; 3:1236-1247.
International Search Report for PCT/US2018/021855, dated Jun. 25, 2018.
Islam, Badar, et al. "Pathophysiological role of peroxynitrite induced DNA damage in human diseases: a special focus on poly (ADP-ribose) polymerase (PARP)." Indian Journal of Clinical Biochemistry 30.4 (2015): 368-385.
Jiao S, et al. Parp inhibitor upregulates pd-11 expression and enhances cancer-associated immunosuppression. Clin. Cancer Res. 2017; 23:3711-3720.
Kanai M, et al. Haploinsufficiency of poly(adp-ribose) polymerase-1-mediated poly(adp-ribosyl)ation for centrosome duplication. Biochemical and biophysical research communications. 2001; 359:426-430.
Kim, Mi Young, et al. "NAD+-dependent modulation of chromatin structure and transcription by nucleosome binding properties of PARP-1." Cell 119.6 (2004): 803-814.
Ansel et al. Pharmaceutical Dosage Forms and Drug Delivery Systems (1999) H.C. eds., 7th ed., Lippincott, Williams and Wilkins, pp. 1-563.
Berger, Nathan A., et al. "Opportunities for the repurposing of PARP inhibitors for the therapy of non-oncological diseases." British journal of pharmacology 175.2 (2018): 192-222.

(56) References Cited

OTHER PUBLICATIONS

Kim, Hogyoung, et al. "Cordycepin blocks lung injury-associated inflammation and promotes BRCA1-deficient breast cancer cell killing by effectively inhibiting PARP." Molecular medicine 17.9 (2011): 893-900. 11.

* cited by examiner

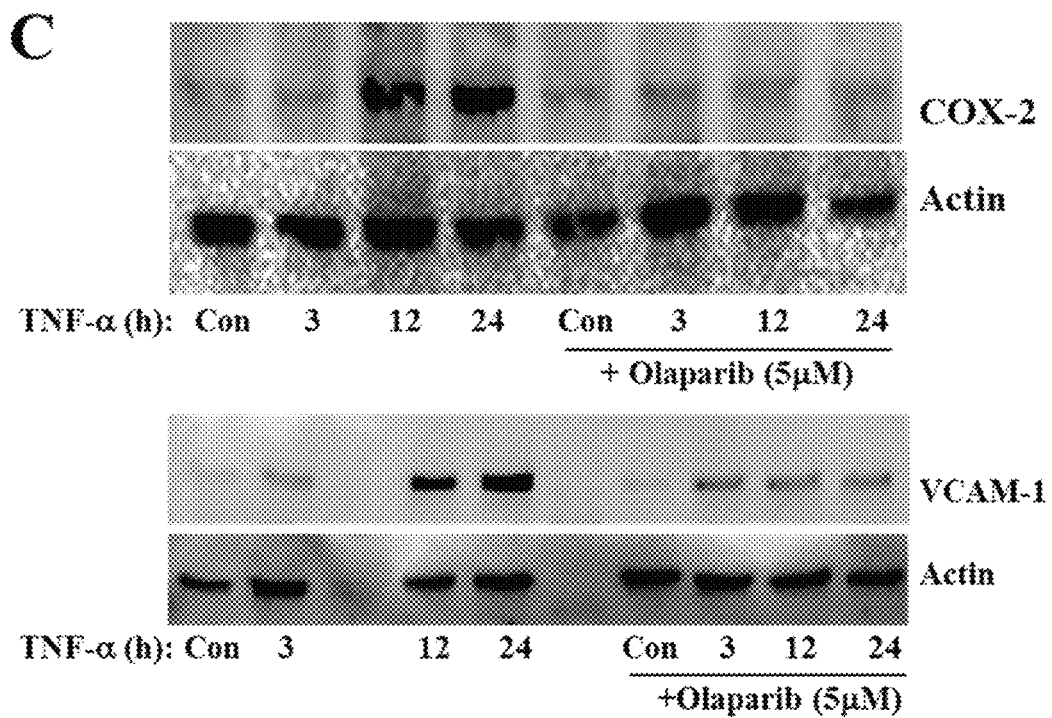
FIG. 1 - CONT.

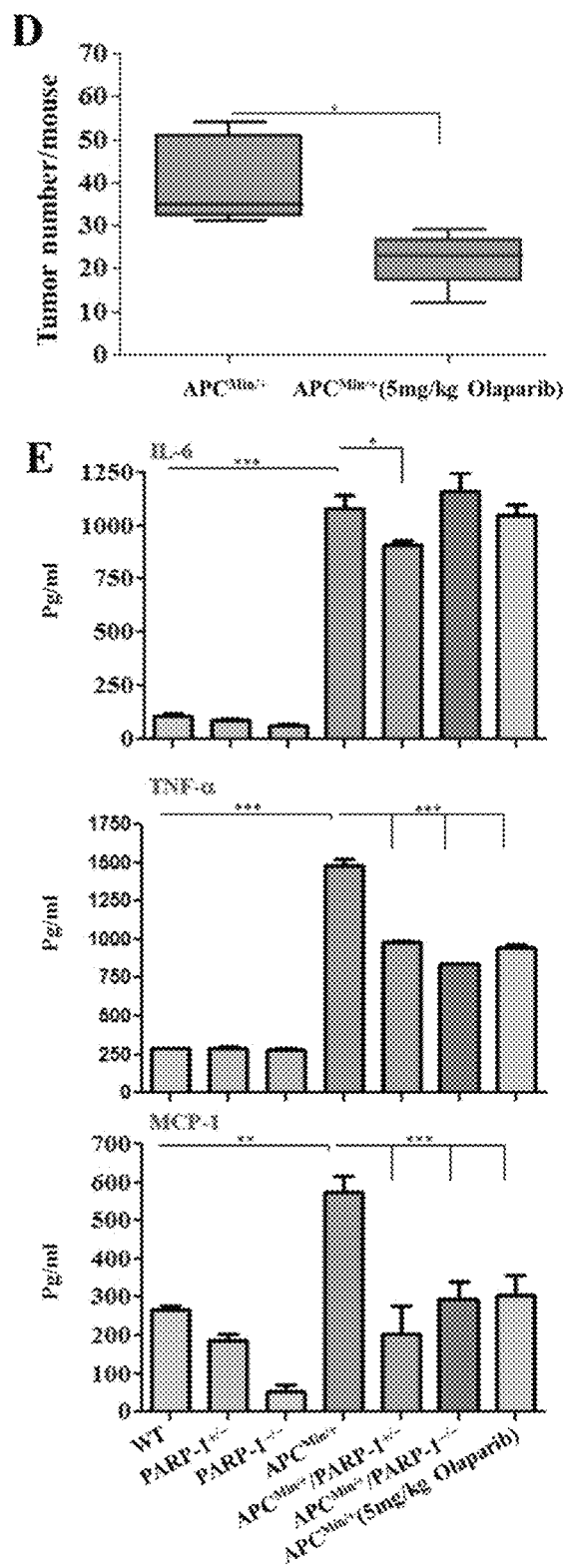
FIG. 5 - CONT.

A.

B.

A.

Primary macrophages

B.

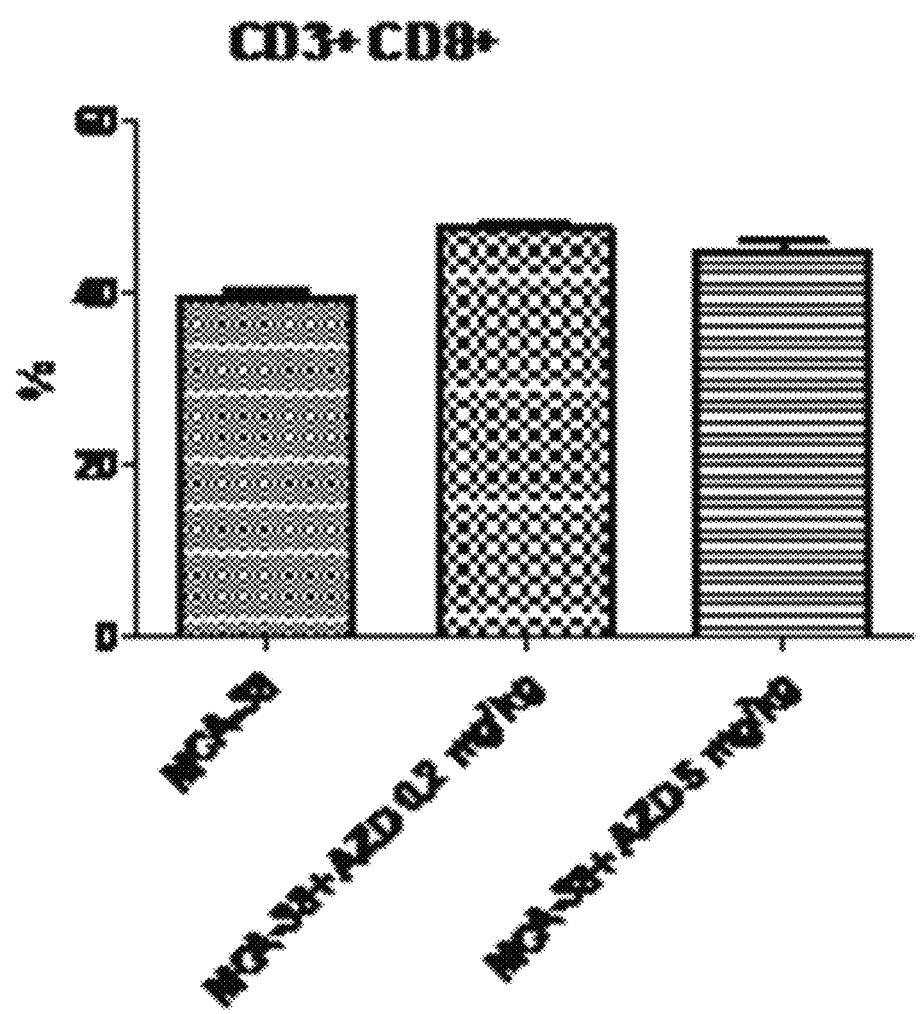
FIG. 31 CON'T

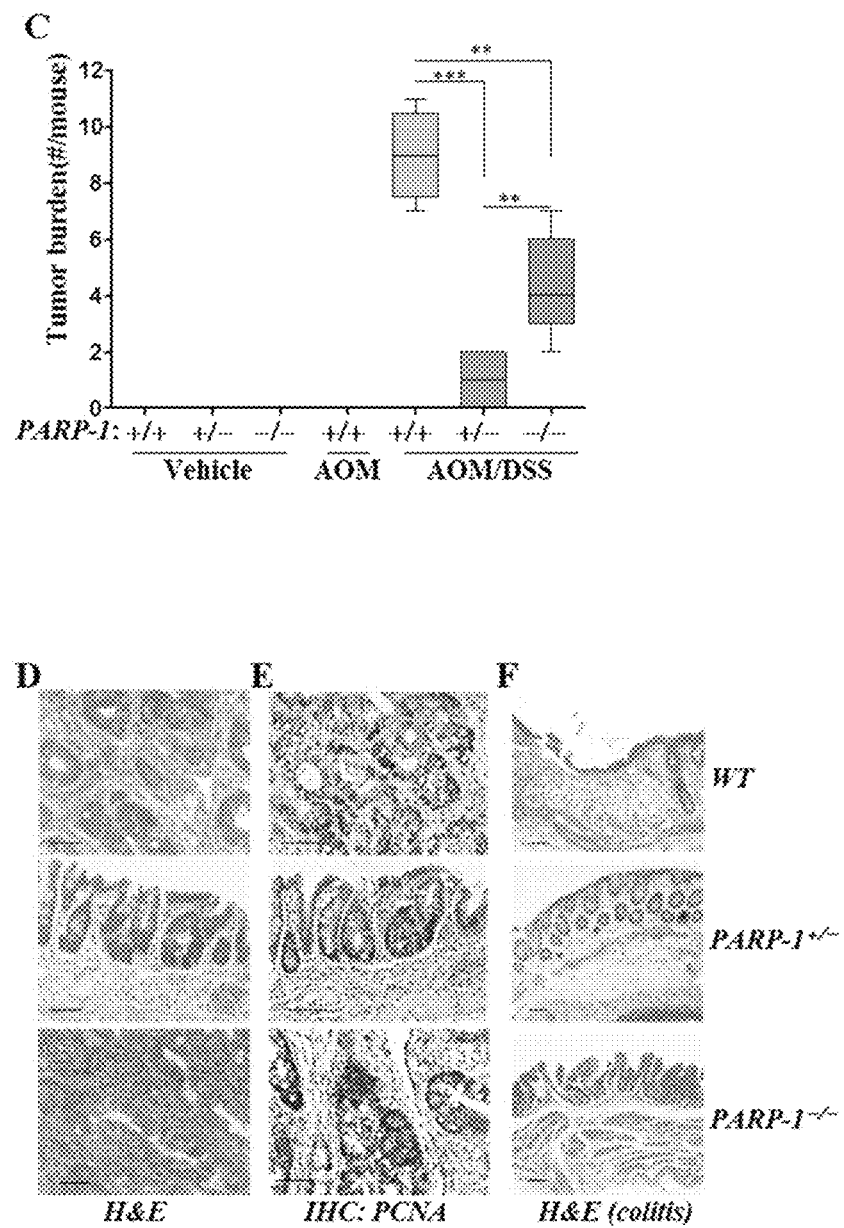
FIG. 32 CON'T

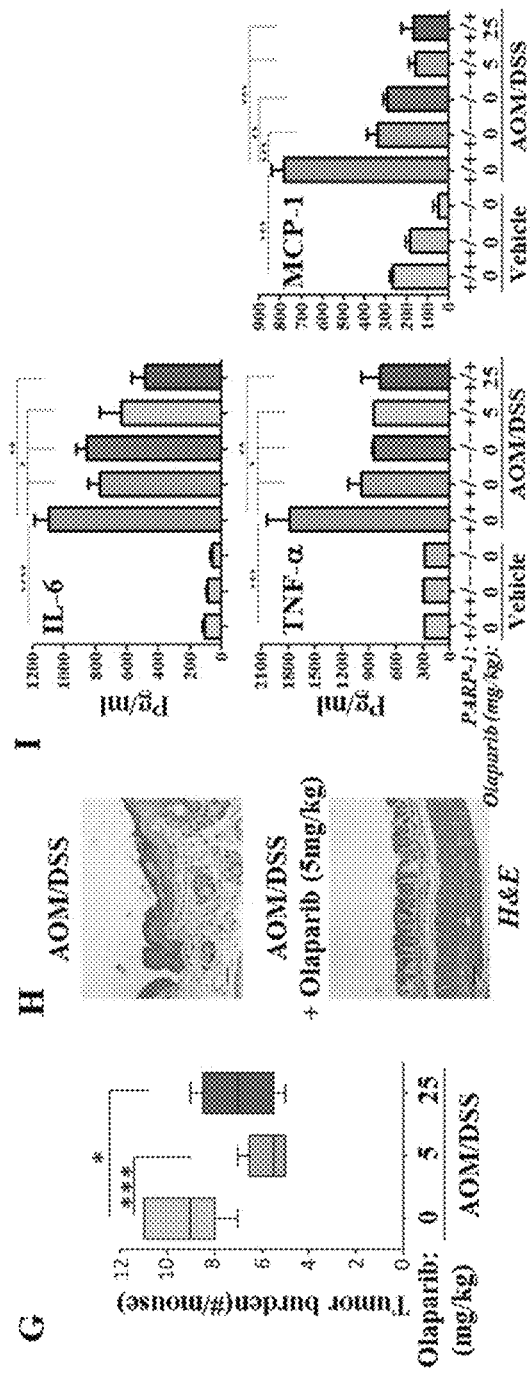
FIG. 32 CON'T

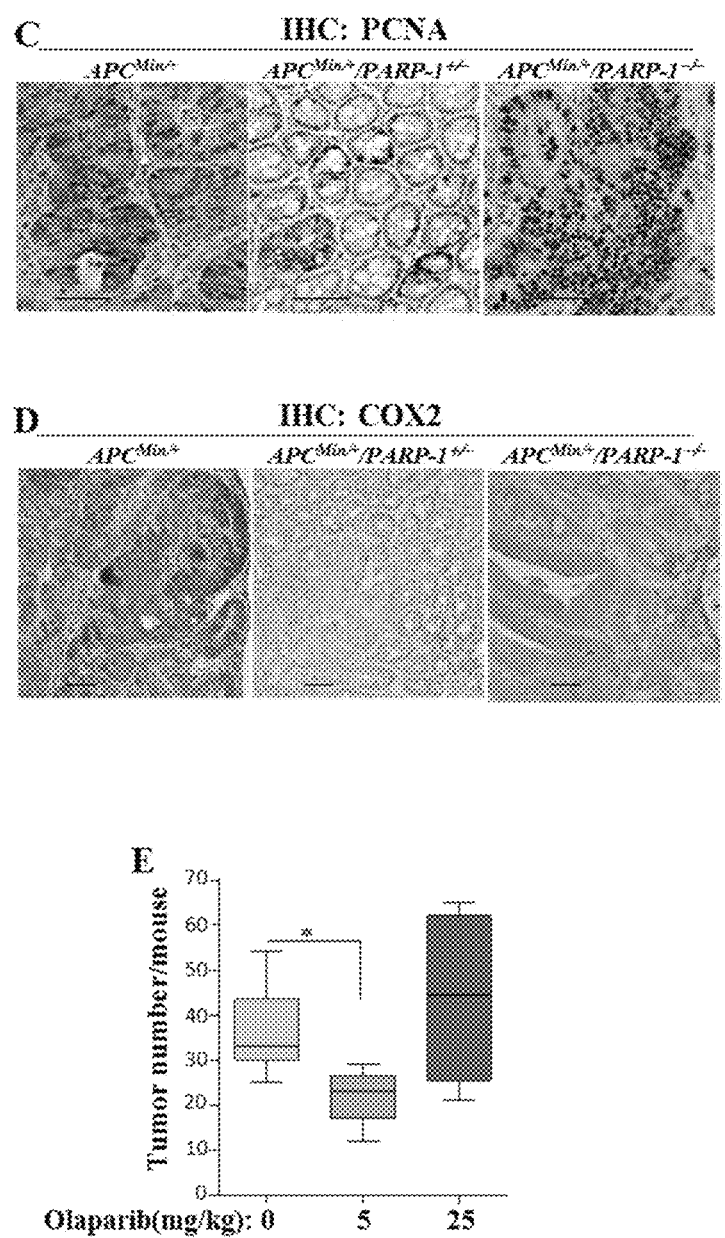
FIG. 33 CON'T

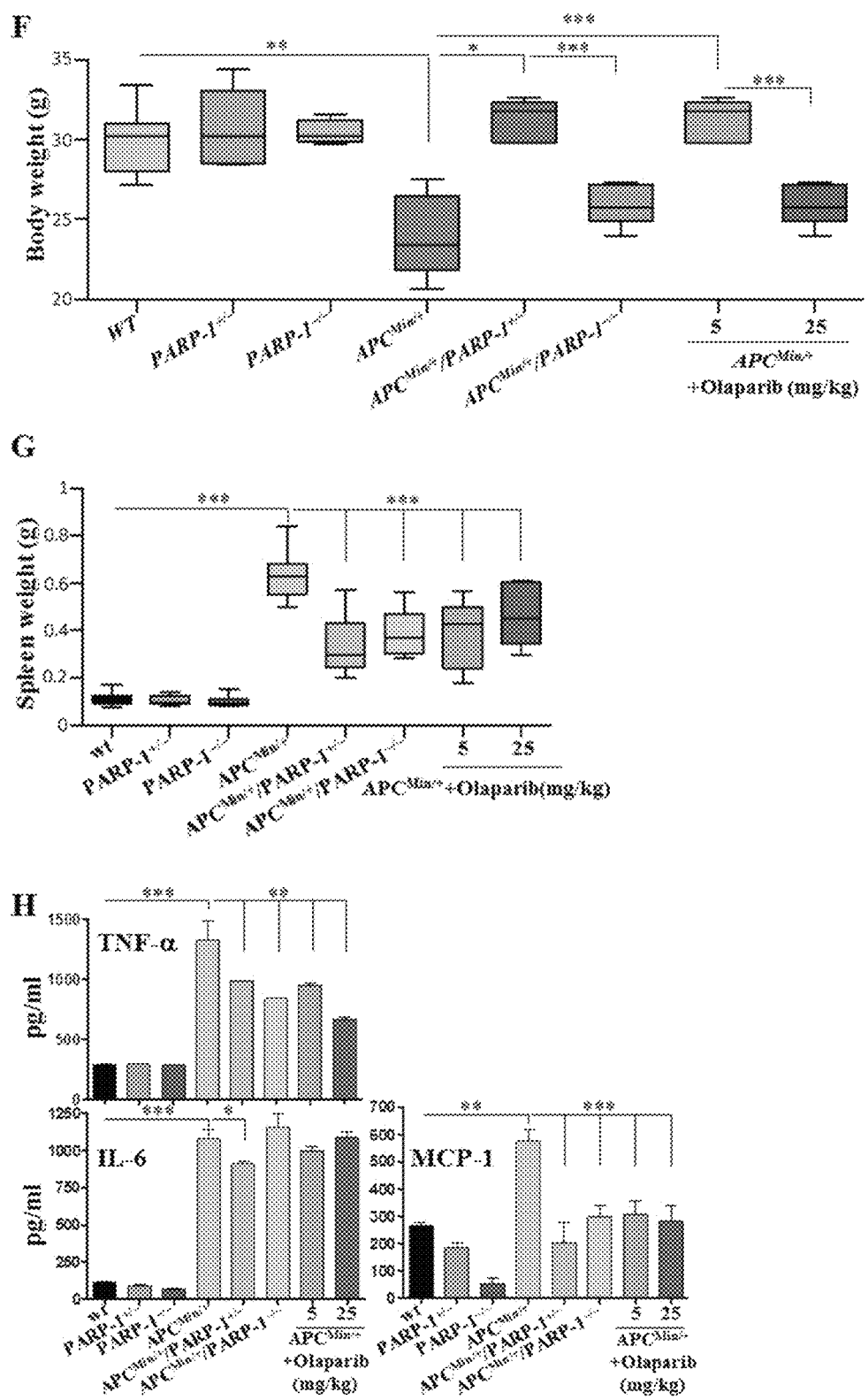
FIG. 33 CON'T

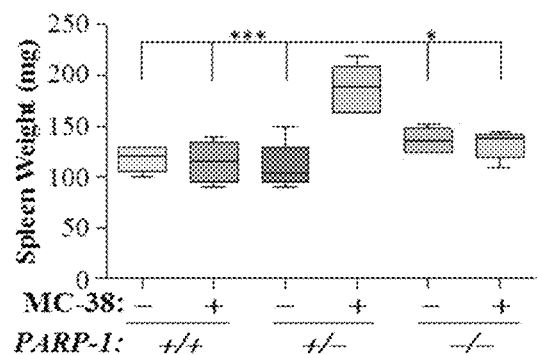
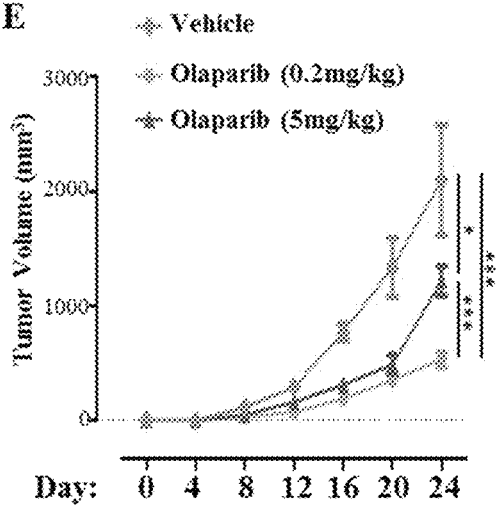
*FIG. 34 CON'T*

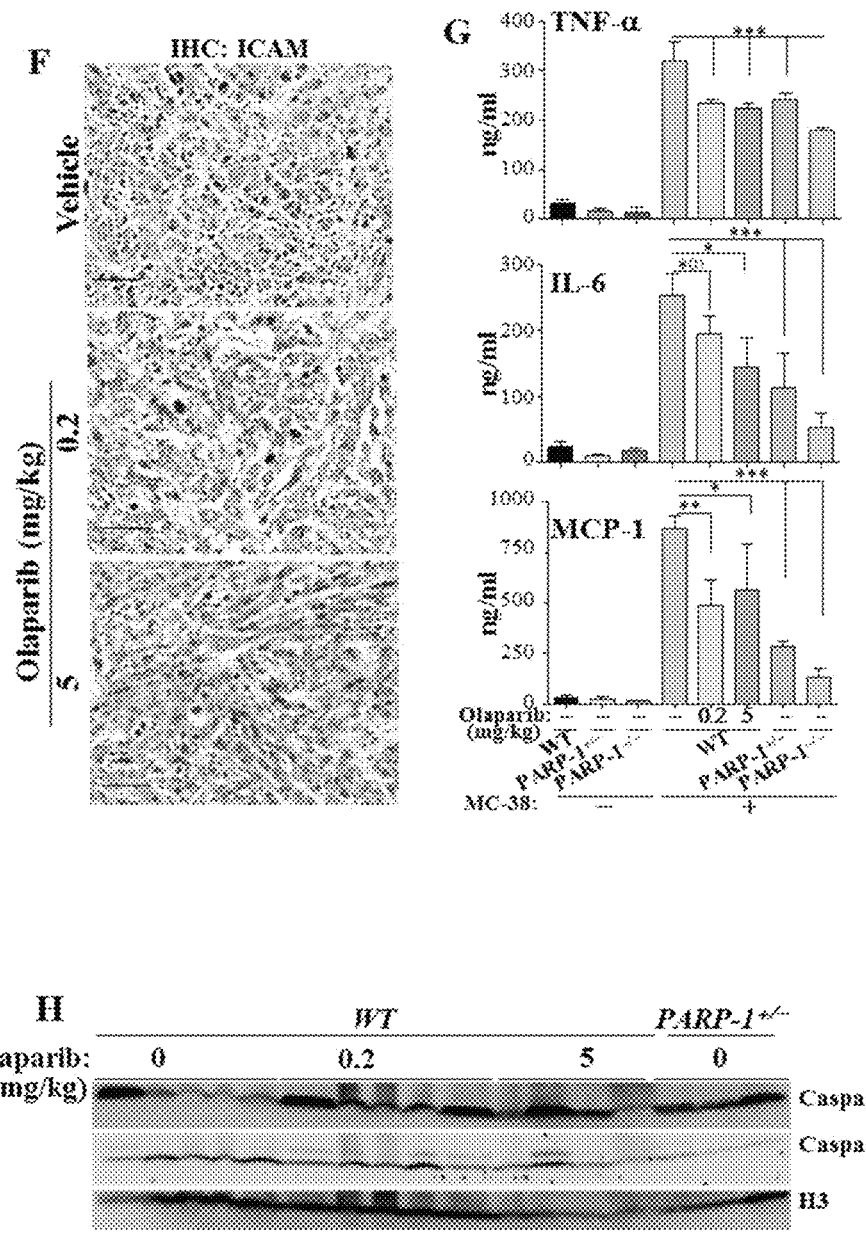
FIG. 34 CON'T

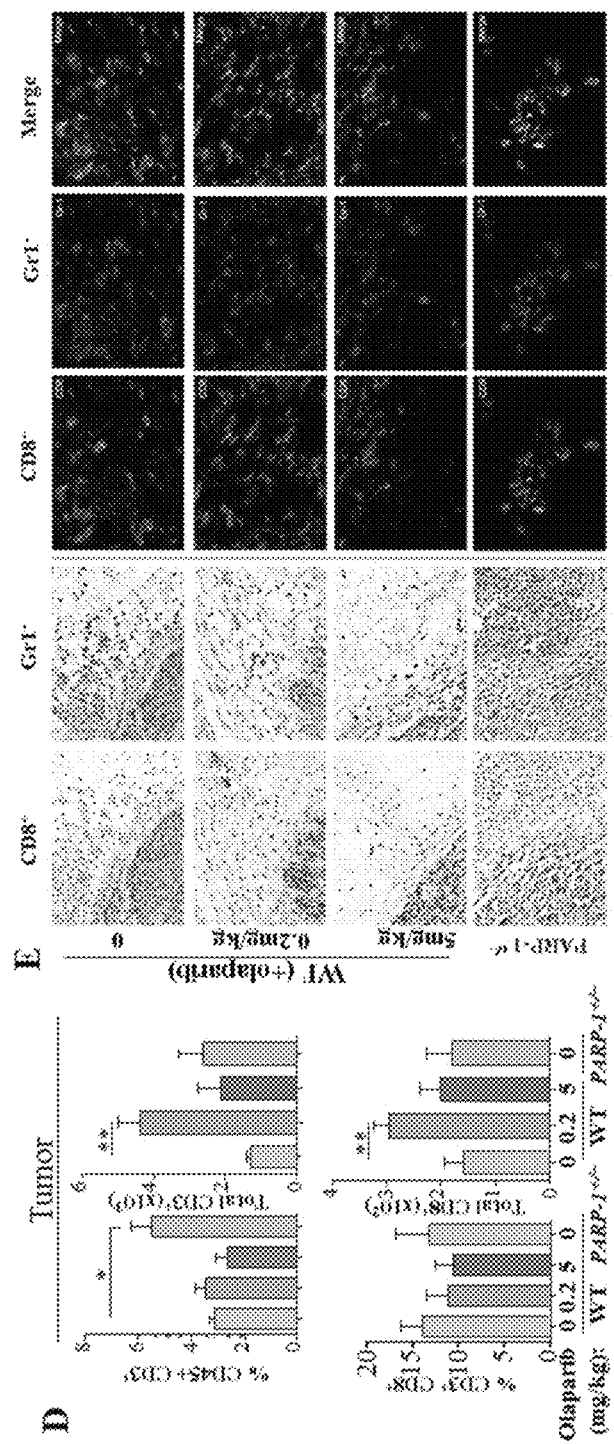
FIG. 35 CON'T

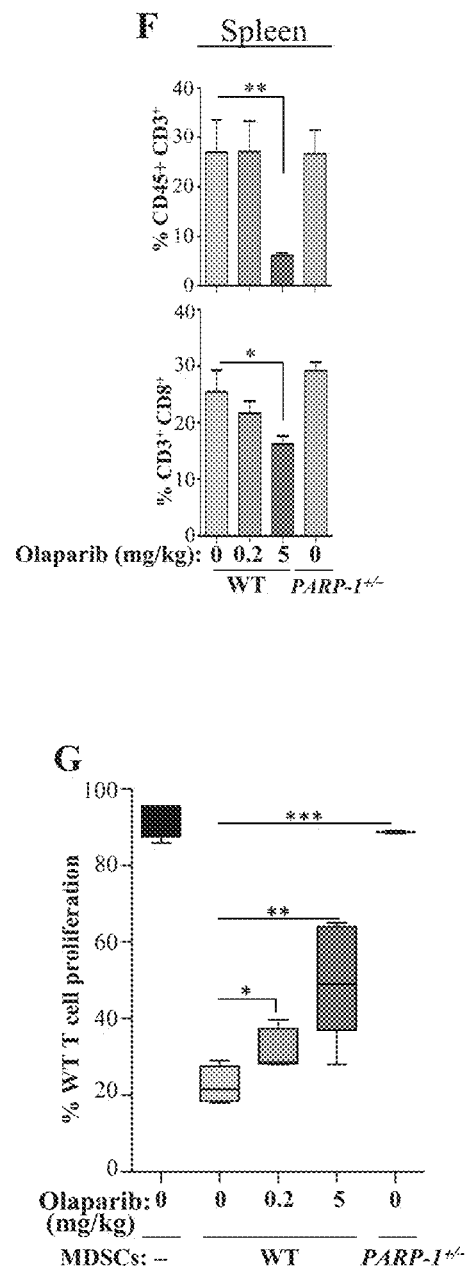
FIG. 35 CON'T

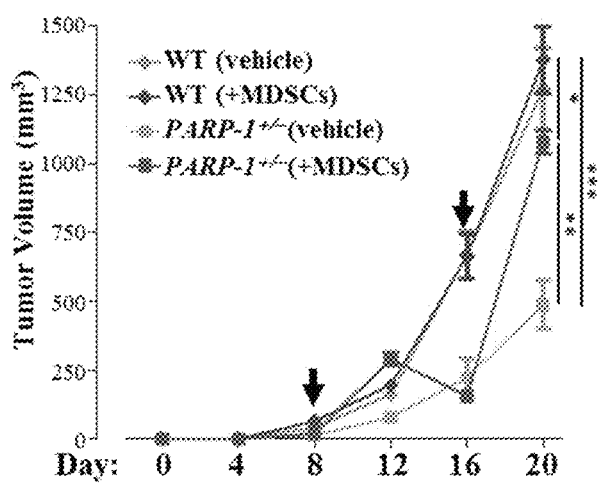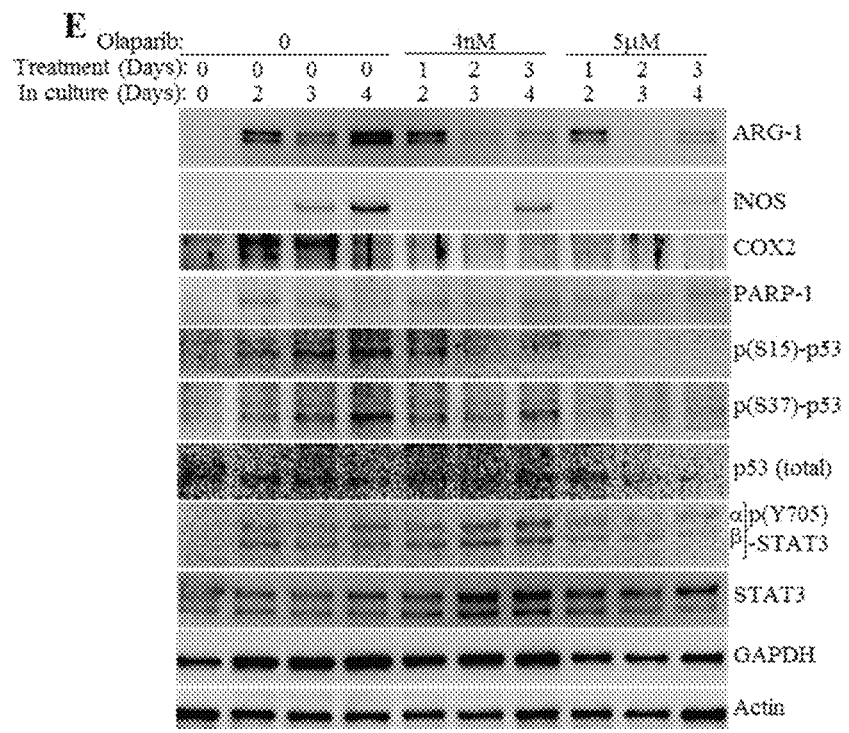
FIG. 36 CON'T

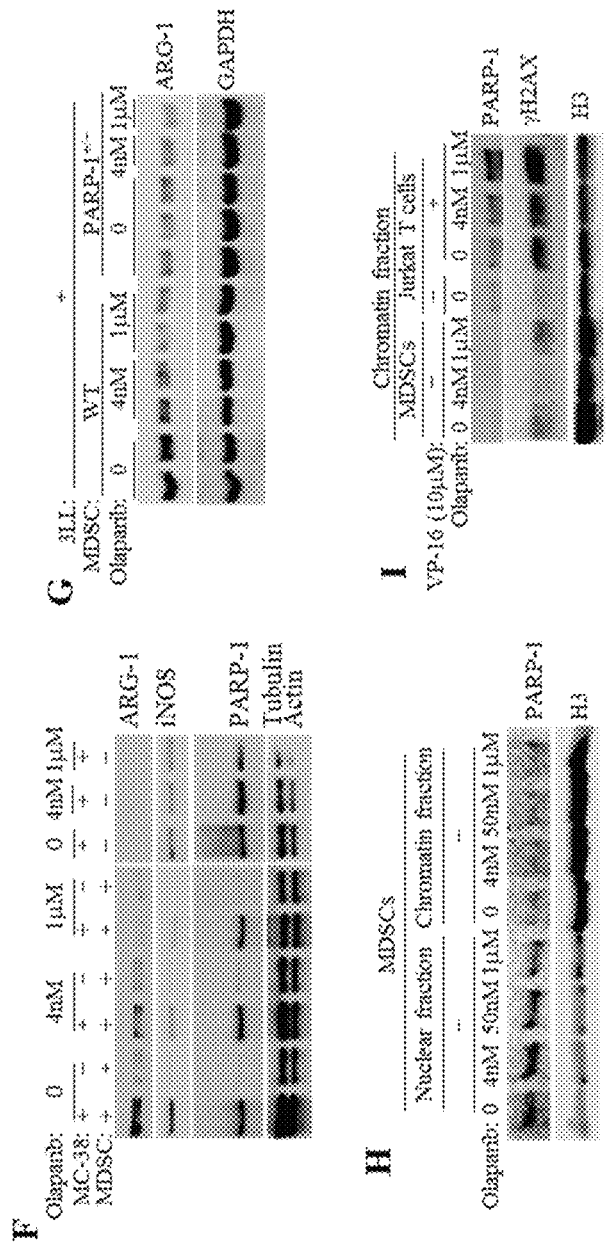
FIG. 36 CON'T

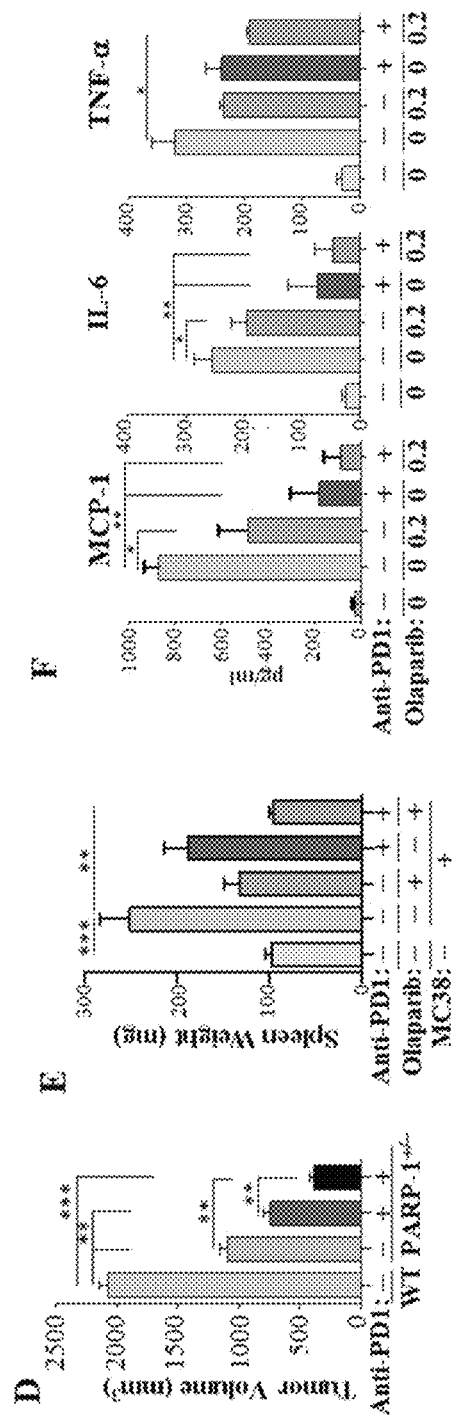
FIG. 37 CON'T

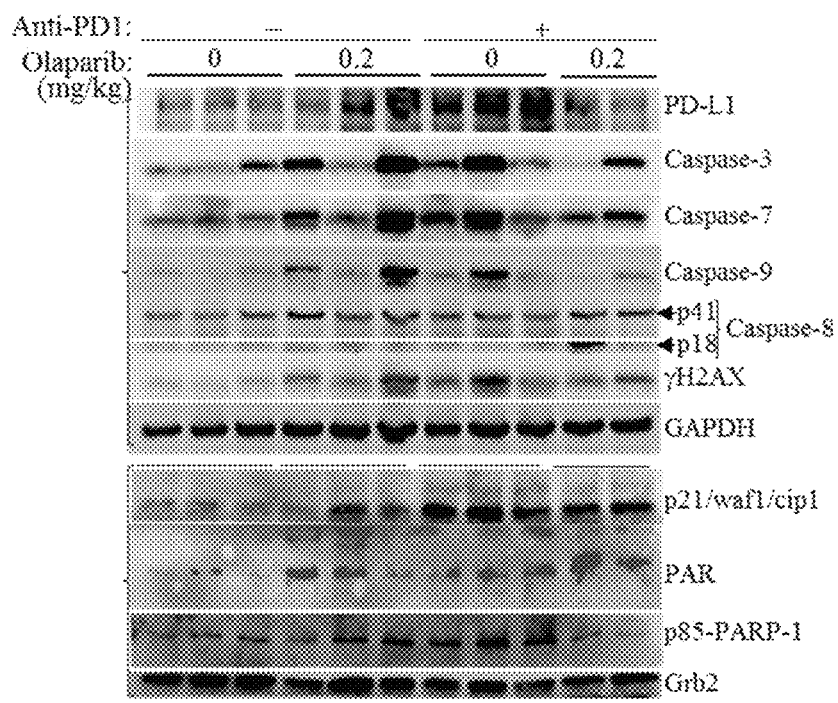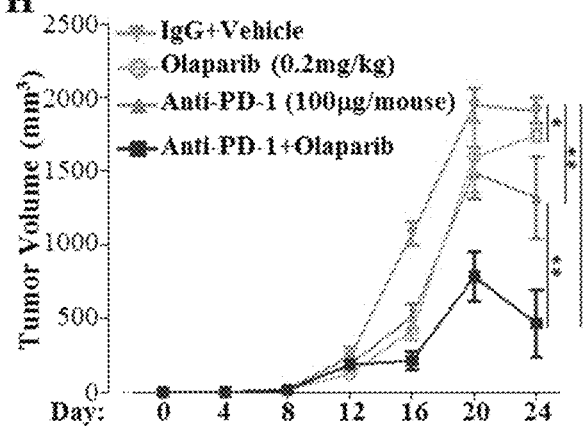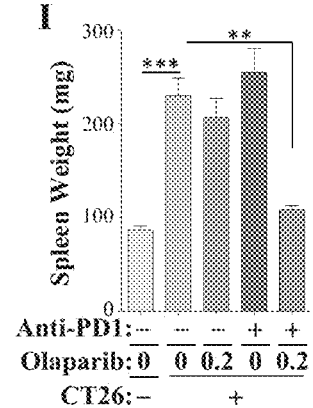
FIG. 37 CON'T

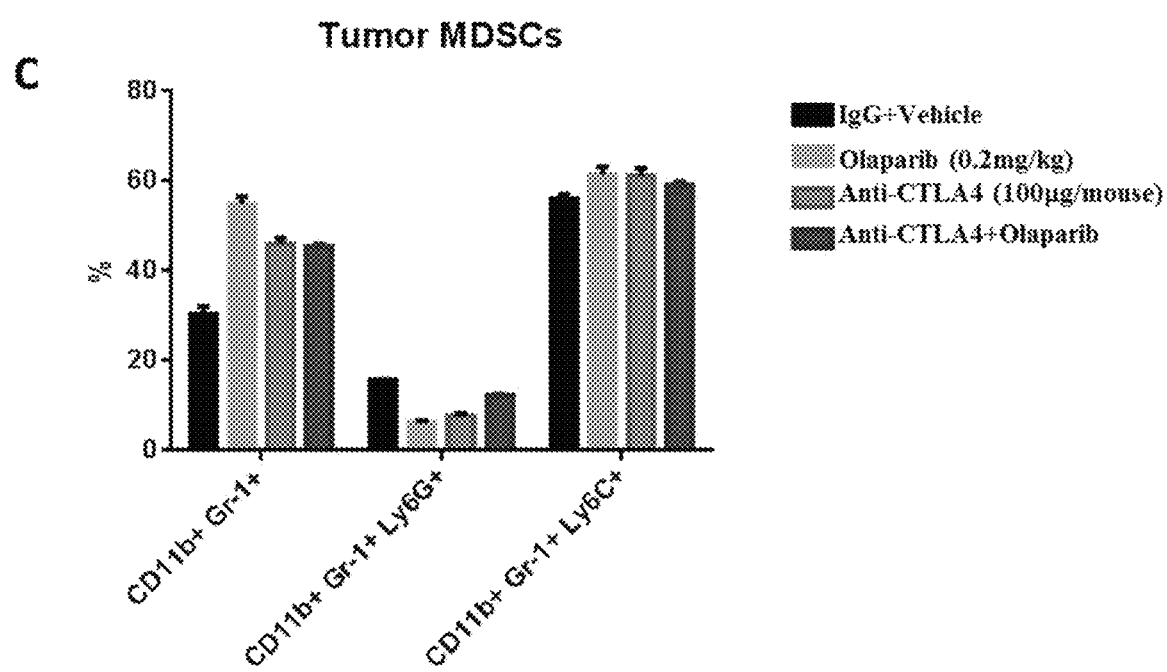
FIG. 46 CON'T

SEQUENCE LISTING

<160> NUMBER OF SEQ ID NOS: 19

<210> SEQ ID NO 1
<211> LENGTH: 20
<212> TYPE: DNA
<213> ORGANISM: Artificial Sequence
<220> FEATURE:
<223> OTHER INFORMATION: Description of Artificial Sequence:
       Synthetic polynucleotide

<400> SEQUENCE: 1
tacagcttca ccaccacagc                                           20

<210> SEQ ID NO 2
<211> LENGTH: 20
<212> TYPE: DNA

```
<213> ORGANISM: Artificial Sequence
<220> FEATURE:
<223> OTHER INFORMATION: Description of Artificial Sequence:
      Synthetic polynucleotide

<400> SEQUENCE: 2
tctccaggga ggaagaggat                                              20

<210> SEQ ID NO 3
<211> LENGTH: 22
<212> TYPE: DNA
<213> ORGANISM: Artificial Sequence
<220> FEATURE:
<223> OTHER INFORMATION: Description of Artificial Sequence:
      Synthetic polynucleotide

<400> SEQUENCE: 3
gtgatgctca ggtatccatc ca                                           22

<210> SEQ ID NO 4
<211> LENGTH: 21
<212> TYPE: DNA
<213> ORGANISM: Artificial Sequence
<220> FEATURE:
<223> OTHER INFORMATION: Description of Artificial Sequence:
      Synthetic polynucleotide

<400> SEQUENCE: 4
cacagttctc aaagcacagc g                                            21

<210> SEQ ID NO 5
<211> LENGTH: 20
<212> TYPE: DNA
<213> ORGANISM: Artificial Sequence
<220> FEATURE:
<223> OTHER INFORMATION: Description of Artificial Sequence:
      Synthetic polynucleotide

<400> SEQUENCE: 5
tcttcgaaat cccacctgac                                              20

<210> SEQ ID NO 6
<211> LENGTH: 20
<212> TYPE: DNA
<213> ORGANISM: Artificial Sequence
<220> FEATURE:
<223> OTHER INFORMATION: Description of Artificial Sequence:
      Synthetic polynucleotide

<400> SEQUENCE: 6
ccatgatggt cacattctgc                                              20

<210> SEQ ID NO 7
<211> LENGTH: 21
<212> TYPE: DNA
<213> ORGANISM: Artificial Sequence
<220> FEATURE:
<223> OTHER INFORMATION: Description of Artificial Sequence:
      Synthetic polynucleotide

<400> SEQUENCE: 7
ctggaagaga cttccatcga g                                            21

<210> SEQ ID NO 8
<211> LENGTH: 23
<212> TYPE: DNA
<213> ORGANISM: Artificial Sequence
```

<220> FEATURE:
<223> OTHER INFORMATION: Description of Artificial Sequence:
      Synthetic polynucleotide

<400> SEQUENCE: 8
agtggtatag acaggtctgt tgg                                             23

<210> SEQ ID NO 9
<211> LENGTH: 25
<212> TYPE: DNA
<213> ORGANISM: Artificial Sequence
<220> FEATURE:
<223> OTHER INFORMATION: Description of Artificial Sequence:
      Synthetic polynucleotide

<400> SEQUENCE: 9
catcttctca aaattcgagt gacaa                                           25

<210> SEQ ID NO 10
<211> LENGTH: 23
<212> TYPE: DNA
<213> ORGANISM: Artificial Sequence
<220> FEATURE:
<223> OTHER INFORMATION: Description of Artificial Sequence:
      Synthetic polynucleotide

<400> SEQUENCE: 10
tgggagtaga caaggtacaa ccc                                             23

<210> SEQ ID NO 11
<211> LENGTH: 22
<212> TYPE: DNA
<213> ORGANISM: Artificial Sequence
<220> FEATURE:
<223> OTHER INFORMATION: Description of Artificial Sequence:
      Synthetic polynucleotide

<400> SEQUENCE: 11
tgccgagcta aattacacat tg                                              22

<210> SEQ ID NO 12
<211> LENGTH: 21
<212> TYPE: DNA
<213> ORGANISM: Artificial Sequence
<220> FEATURE:
<223> OTHER INFORMATION: Description of Artificial Sequence:
      Synthetic polynucleotide

<400> SEQUENCE: 12
ccttgtggag ggatgtacag a                                               21

<210> SEQ ID NO 13
<211> LENGTH: 21
<212> TYPE: DNA
<213> ORGANISM: Artificial Sequence
<220> FEATURE:
<223> OTHER INFORMATION: Description of Artificial Sequence:
      Synthetic polynucleotide

<400> SEQUENCE: 13
catgttcgat gggaaagtcc c                                               21

<210> SEQ ID NO 14
<211> LENGTH: 22
<212> TYPE: DNA
<213> ORGANISM: Artificial Sequence
<220> FEATURE:

```
<223> OTHER INFORMATION: Description of Artificial Sequence:
      Synthetic polynucleotide

<400> SEQUENCE: 14
ccagcgcagc tcagagaagc ca                                               22

<210> SEQ ID NO 15
<211> LENGTH: 20
<212> TYPE: DNA
<213> ORGANISM: Artificial Sequence
<220> FEATURE:
<223> OTHER INFORMATION: Description of Artificial Sequence:
      Synthetic polynucleotide

<400> SEQUENCE: 15
aggtgagatg acaggagatc                                                  20

<210> SEQ ID NO 16
<211> LENGTH: 18
<212> TYPE: DNA
<213> ORGANISM: Artificial Sequence
<220> FEATURE:
<223> OTHER INFORMATION: Description of Artificial Sequence:
      Synthetic polynucleotide

<400> SEQUENCE: 16
gccatccctt cacgttag                                                    18

<210> SEQ ID NO 17
<211> LENGTH: 19
<212> TYPE: DNA
<213> ORGANISM: Artificial Sequence
<220> FEATURE:
<223> OTHER INFORMATION: Description of Artificial Sequence:
      Synthetic polynucleotide

<400> SEQUENCE: 17
ttccactttg gcataaggc                                                   19

<210> SEQ ID NO 18
<211> LENGTH: 21
<212> TYPE: DNA
<213> ORGANISM: Artificial Sequence
<220> FEATURE:
<223> OTHER INFORMATION: Description of Artificial Sequence:
      Synthetic polynucleotide

<400> SEQUENCE: 18
ttctgagaaa gacagaagtt a                                                21

<210> SEQ ID NO 19
<211> LENGTH: 39
<212> TYPE: PRT
<213> ORGANISM: Unknown
<220> FEATURE:
<223> OTHER INFORMATION: Description of Unknown:
      PARP-1 NLS sequence

<400> SEQUENCE: 19

Val Lys Ser Glu Gly Lys Arg Lys Gly Asp Glu Val Asp Gly Val Asp
1               5                   10                  15

Glu Val Ala Lys Lys Lys Ser Lys Lys Glu Lys Asp Lys Asp Ser Lys
            20                  25                  30

Leu Glu Lys Ala Leu Lys Ala
        35
```

PARP-1 AND METHODS OF USE THEREOF

This application is a Continuation-in-Part of International Application No. PCT/US2018/021855, filed on Mar. 9, 2018, which claims priority from U.S. Provisional Application No. 62/469,436 filed on Mar. 9, 2017, the entire contents of which are each incorporated herein by reference.

GOVERNMENT INTERESTS

This invention was made with government support under Grant Nos. R01HL072889, P3OGM114732, P20GM103501 and P20CA233374 awarded by the National Institutes of Health. The government has certain rights in the invention.

REFERENCE TO A SEQUENCE LISTING

This application contains a Sequence Listing in computer readable form. The computer readable form is incorporated herein by reference. Said ASCII copy, created on Apr. 12, 2023, is named 2932719-010-US2 SL.txt and is 5,073 bytes in size.

All patents, patent applications and publications cited herein are hereby incorporated by reference in their entirety. The disclosures of these publications in their entireties are hereby incorporated by reference into this application in order to more fully describe the state of the art as known to those skilled therein as of the date of the invention described and claimed herein.

This patent disclosure contains material that is subject to copyright protection. The copyright owner has no objection to the facsimile reproduction by anyone of the patent document or the patent disclosure as it appears in the U.S. Patent and Trademark Office patent file or records, but otherwise reserves any and all copyright rights.

FIELD OF THE INVENTION

This invention is directed to roles for PARP-1 in disease.

BACKGROUND OF THE INVENTION

Colon cancer is complex and involves a large number of genetic and environmental factors such as mutations in specific genes and chronic inflammation. In familial adenomatous polyposis (FAP) syndrome, mutations in both alleles of the APC gene that result in its inactivation are considered one of the initial events in colorectal carcinogenesis. It is not clear whether this type of cancer is driven by chronic inflammation although inflammation manifests itself during the course of the disease. Several studies showed conflicting results on the effect of anti-inflammatory conditions on $APC^{Min/+}$-driven tumor burden. In carcinogen/chronic inflammation (AOM/DSS)-driven colon cancer, most of the anti-inflammatory factors prevent or reduce tumor burden in mice.

SUMMARY OF THE INVENTION

Immunotherapy is increasingly regarded as a critical approach to treat many forms of cancers. Its efficacy is sometimes a limitation. Given the role of PARP-1 in the function of MDSCs and the ability of partial PARP inhibition to reduce the suppressive activity of these cells, it is conceivable to use PARP inhibitors at a dose that can be gaged according to the type of cancer and affected patient to achieve a better clinical outcome with immunotherapy approaches. It is also conceivable to use this approach (i.e. partial PARP inhibition) with therapies whose targets do not include DNA repair/damage.

Aspects of the invention are directed towards a method for treating a tumor in a subject.

Aspects of the invention are further directed towards a method of reducing progression or promoting regression of a tumor in a subject.

Still further, aspects of the invention are directed towards a method of reducing cellular proliferation of a tumor cell in a subject.

In embodiments, the tumor comprises a solid tumor or a liquid tumor. A tumor can be benign, premalignant, or malignant. In embodiments, the tumor does not comprise a mutation in a BRCA gene, nor is the tumor considered a "triple negative" cancer based on negative oestrogen receptor (ER), progesterone receptor (PR) and human epidermal growth factor receptor-type 2 (HER2) expression A tumor can be one that is influenced by the immune system. A tumor can be a primary tumor, or a metastatic lesion. Non-limiting examples of cancers that are associated with tumor formation comprise brain cancer, head & neck cancer, esophageal cancer, tracheal cancer, lung cancer, liver cancer stomach cancer, colon cancer, pancreatic cancer, breast cancer, cervical cancer, uterine cancer, bladder cancer, prostate cancer, testicular cancer, skin cancer, rectal cancer, and lymphomas. Non-limiting examples of liquid tumors comprise neoplasia of the reticuloendothelial or haematopoetic system, such as lymphomas, myelomas and leukemias. Non-limiting examples of leukemias include acute and chronic lymphoblastic, myeolblastic and multiple myeloma. Typically, such diseases arise from poorly differentiated acute leukemias, e.g., erythroblastic leukemia and acute megakaryoblastic leukemia. Specific myeloid disorders include, but are not limited to, acute promyeloid leukemia (APML), acute myelogenous leukemia (AML) and chronic myelogenous leukemia (CML). Lymphoid malignancies include, but are not limited to, acute lymphoblastic leukemia (ALL), which includes B-lineage ALL and T-lineage ALL, chronic lymphocytic leukemia (CLL), prolymphocytic leukemia (PLL), hairy cell leukemia (HLL) and Waldenstrom's macroglobulinemia (WM). Specific malignant lymphomas include, non-Hodgkin lymphoma and variants, peripheral T cell lymphomas, adult T cell leukemia/lymphoma (ATL), cutaneous T-cell lymphoma (CTCL), large granular lymphocytic leukemia (LGF), Hodgkin's disease and Reed-Sternberg disease.

In embodiments, the formation and/or growth of the tumor is exacerbated by chronic inflammation, the amount of which is dependent upon tumor type.

In embodiments, the method comprises administering to the subject afflicted with the tumor a low-dose, therapeutically effective amount of a PARP inhibitor compound.

In embodiments, the PARP inhibitor compound inhibits the enzymatic activity of one or more proteins in the PARP family of proteins. For example, the PARP inhibitor compound inhibits the enzymation activity of PARP-1, PARP-2, PARP-3, PARP-4, PARP-5a, PARP-5b, PARP-6, PARP-7, PARP-8, PARP-9, PARP-10, PARP-11, PARP-12, PARP-13, PARP-14, PARP-15, PARP-16, or any combination thereof. In specific embodiments, the PARP inhibitor compound inhibits the enzymatic activity of PARP-1, PARP-2, PARP-3, or any combination thereof.

In embodiments, the enzymatic activity inhibited by a PARP inhibitor compound comprises poly(ADP-ribosylation).

In embodiments, the PARP inhibitor compound comprises a compound of Formula (I):

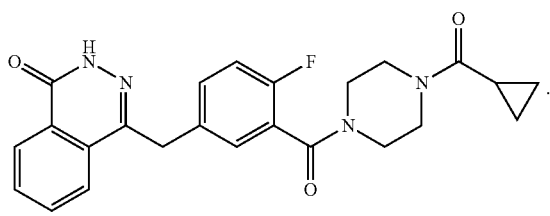 [SMILES: O=C(c1cc(Cc2n[nH]c(=O)c3ccccc23)ccc1F)N1CCN(C(=O)C2CC2)CC1]

In embodiments, the PARP inhibitor compound is a compound of Formula (I):

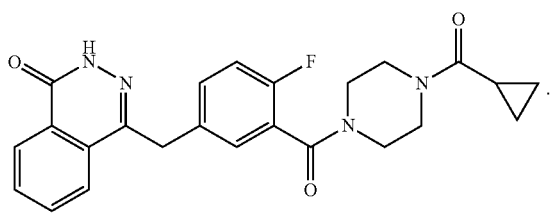 [SMILES: O=C(c1cc(Cc2n[nH]c(=O)c3ccccc23)ccc1F)N1CCN(C(=O)C2CC2)CC1]

In embodiments, a subject is administered a PARP inhibitor compound at a low dose, therapeutically effective amount. For example, the low dose of a PARP inhibitor comprises a dose that is about 10×, 20×, 30×, 40×, 50×, 60×, 70×, 80×, 90×, 100×, 110×, 120×, 130×, 140×, or 150× lower than what is currently prescribed.

Embodiments of the invention comprise a dose of about 1 mg per day, about 5 mg per day, about 10 mg per day, about 15 mg per day, about 20 mg per day, about 25 mg per day, about 30 mg per day, about 35 mg per day, about 40 mg per day or about 50 mg per day.

In embodiments, a subject is administered a PARP inhibitor compound at a low dose, therapeutically effective amount that reduces the enzymatic activity of a PARP between about 10% reduction in activity and about 50% reduction in activity, but nevertheless does not abolish enzymatic activity. Specifically, the method as described herein pertains to administering to a subject a low dose, therapeutically effective amount of a PARP inhibitor compound that reduces the poly(ADP-ribosyl)ation activity of PARP-1 by about 10%, about 20%, about 30%, about 40%, or about 50%. In other embodiments, the PARP inhibitor compound reduces the enzymatic activity by about 60%, about 70%, about 80%, about 90%, or about 100%, but does not abolish the enzymatic activity of the PARP. In embodiments, the reduction of the enzymatic activity of PARP is compared to the activity level of PARP when activated by DNA damage (such as by DNA damaging chemotherapeutic agents like cisplatin, etoposide, or gamma radiation).

In embodiments, the PARP inhibitor compound modulates the tumor microenvironment. For example the PARP inhibitor compound reduces the activity of myeloid derived suppressor cells (MDSCs). In embodiments, the PARP inhibitor compound reduces the tumor suppressive activity of MDSCs. Modulation of the tumor microenvironment can be measured by, for example, assessment of immune cells within a biopsy (such as by FACS using markers specific to MDSC, CD8, NK, DC).

In embodiments, the PARP inhibitor compound is administered as a pharmaceutical composition. In some embodiments, the pharmaceutical composition further comprises at least one additional anti-cancer agent and/or an anti-inflammatory agent. For example, the anti-cancer agent can be an anti-cancer immunotherapy, such as an anti-PD1 antibody, an anti-CTLA4 antibody, an anti-PDL1 antibody, or other such checkpoint blockade antibodies known in the art (e.g., Aris et al., (2017) Front Immunol., 8: 1024; and Diesendruck et al., (2017) Drug Resist Updat. January; 30:39-47, each of which are incorporated by reference in their entireties). In other embodiments, the anti-cancer agent can be an inhibitor of indoleamine 2,3-dioxygenase-1 (i.e., IDO inhibitor). For example, the IDO inhibitor can be a small molecule inhibitor, such as Epacadostat, Indoximod, or Navoximod.

In embodiments, the PARP inhibitor compound is administered in a single dose.

In embodiments, the PARP inhibitor compound is administered at intervals of about 4 hours, 12 hours, or 24 hours. In some embodiments, the PARP inhibitor compound is administered to the subject on a regular basis, for example three times a day, two times a day, once a day, every other day or every 3 days. In other embodiments, the PARP inhibitor compound is administered to the subject on an intermittent basis, for example twice a day followed by once a day followed by three times a day; or the first two days of every week; or the first, second and third day of a week. In some embodiments, intermittent dosing is as effective as regular dosing.

In embodiments, the PARP inhibitor compound is administered orally, intraperitoneally, subcutaneously, intravenously, or intramuscularly.

Aspects of the invention are also drawn towards a dosing regime for the treatment of cancer in a subject. For example, the dosing regimen comprises administering to a subject a metronomic dose of a PARP inhibitor compound. In other embodiments, the dosing regime further comprises administering therapeutically effective amount of at least one additional anti-cancer agent. For example, the metronomic dose of the PARP inhibitor compound comprises a dose that is below the established maximum tolerated dose of the PARP inhibitor.

In embodiments, the PARP inhibitor compound is administered every other day.

In embodiments, the at least one additional anti-cancer agent is administered to the subject every four (4) days, every seven (7) days, every fourteen (14) days, every twenty-one (21) days, or every twenty-eight (28) days. For example, the at least one additional anti-cancer agent comprises a checkpoint blockade inhibitor, such as anti-PD1 or anti-CTLA4 antibody. In other embodiments, the anti-cancer agent comprises an IDO inhibitor, such as Epacadostat, Indoximod, or Navoximod.

Other objects and advantages of this invention will become readily apparent from the ensuing description.

BRIEF DESCRIPTION OF THE FIGURES

The patent or patent application file contains at least one drawing executed in color. Copies of this patent or patent application publication with color drawings will be provided by the office upon request and payment of the necessary fee.

Figure 2:
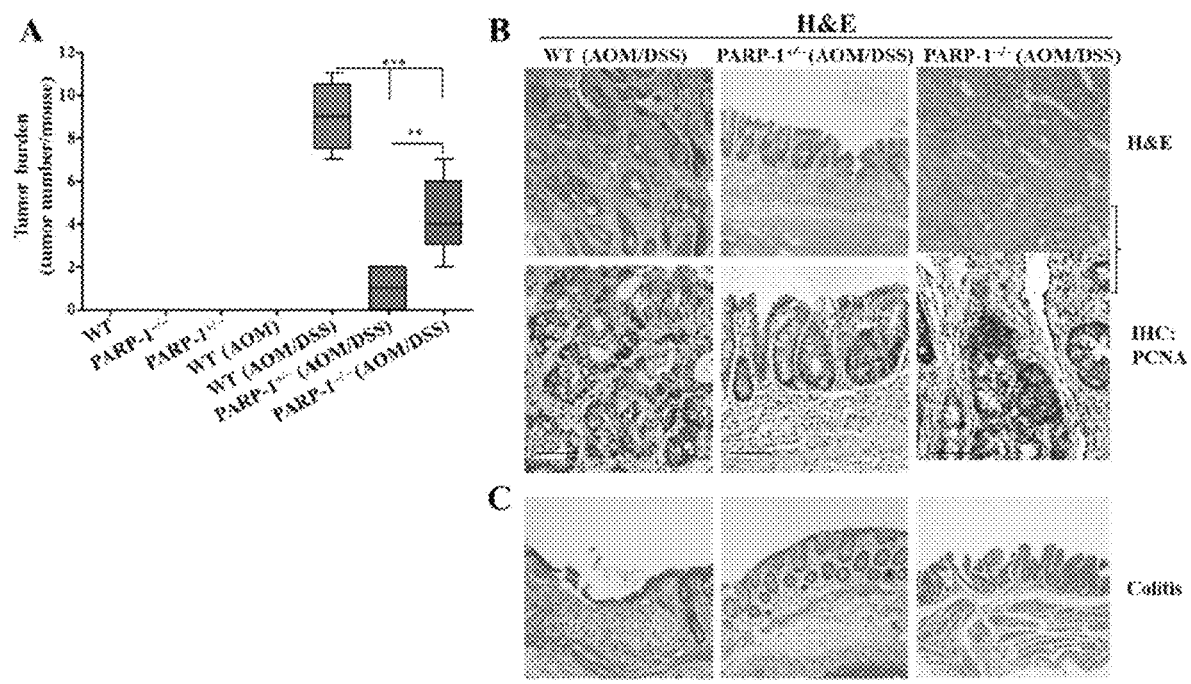

FIG. 2 shows partial PARP-1 inhibition by gene heterozygosity is more efficient than complete inhibition by gene knockout at reducing chronic inflammation-driven colon tumorigenesis in an AOM/DSS mouse model of colon cancer. WT, PARP-1+/− or PARP-1−/− mice received a single injection of the carcinogen azoxymethane (AOM) followed by 4 bi-weekly cycles of DSS (inducer of chronic inflammation) and sacrificed at 16 wks of age. (A) Tumor numbers along the colon were assessed. (B) H&E staining of tumors and immunohistochemical analysis with antibodies to PCNA, a marker of cell proliferation. (C) H&E staining showing the protective effect of PARP-1 gene heterozygosity or knockout against AOM/DSS-induced colitis.

Figure 3:
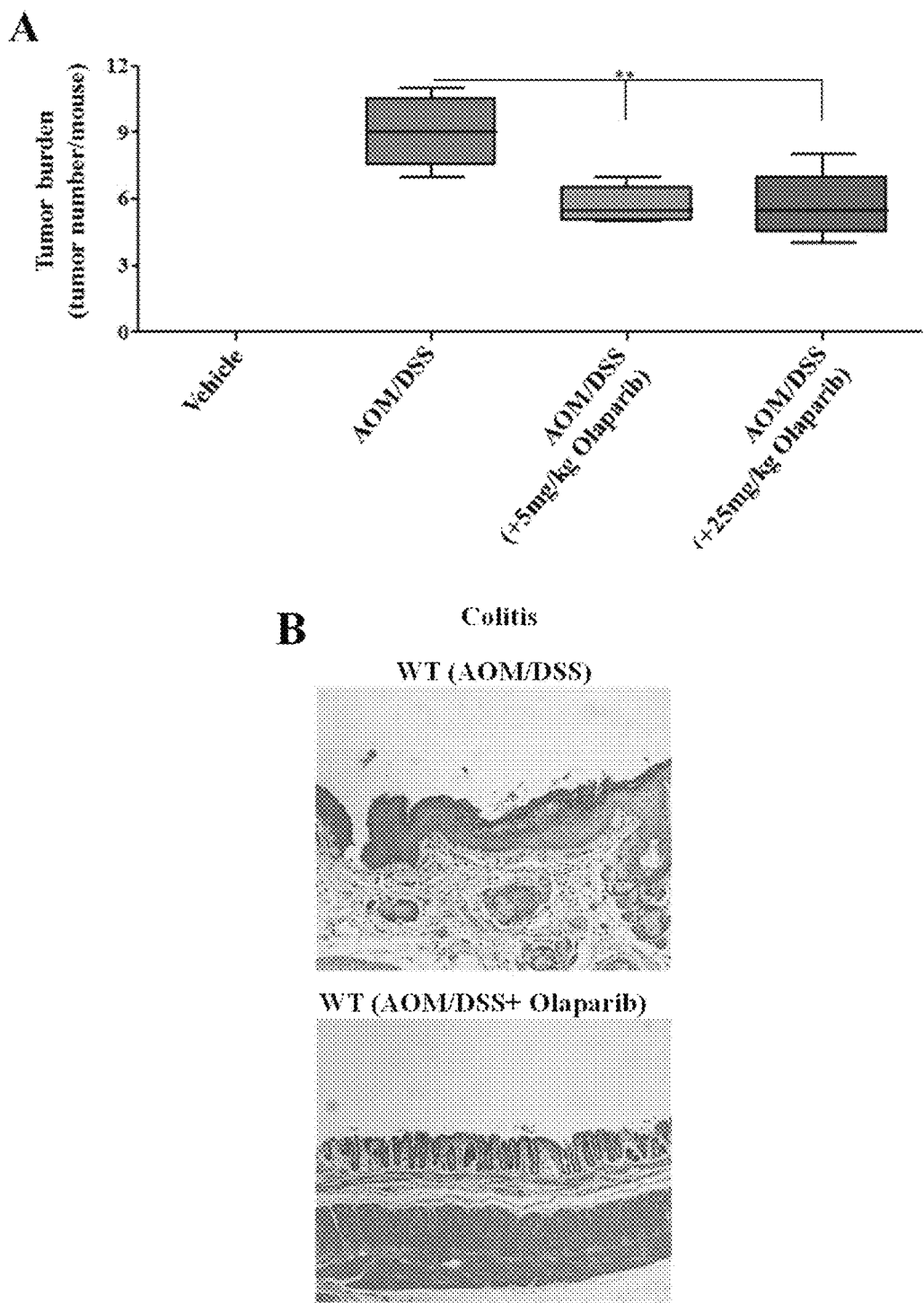

FIG. 3 shows pharmacological inhibition of PARP by olaparib is very effective at reducing COX-2 partially reduces the tumor burden in AOM/DSS-treated WT mice. WT were treated with AOM and DSS as described above. Groups of mice were administered 5 mg/kg or 25 mg/kg olaparib twice a week. Mice were sacrificed at 16 wks of age. (A) Tumor numbers were counted. (B) H&E staining showing the protective effect of PARP-1 inhibition by olaparib against AOM/DSS-induced colitis.

Figure 4:
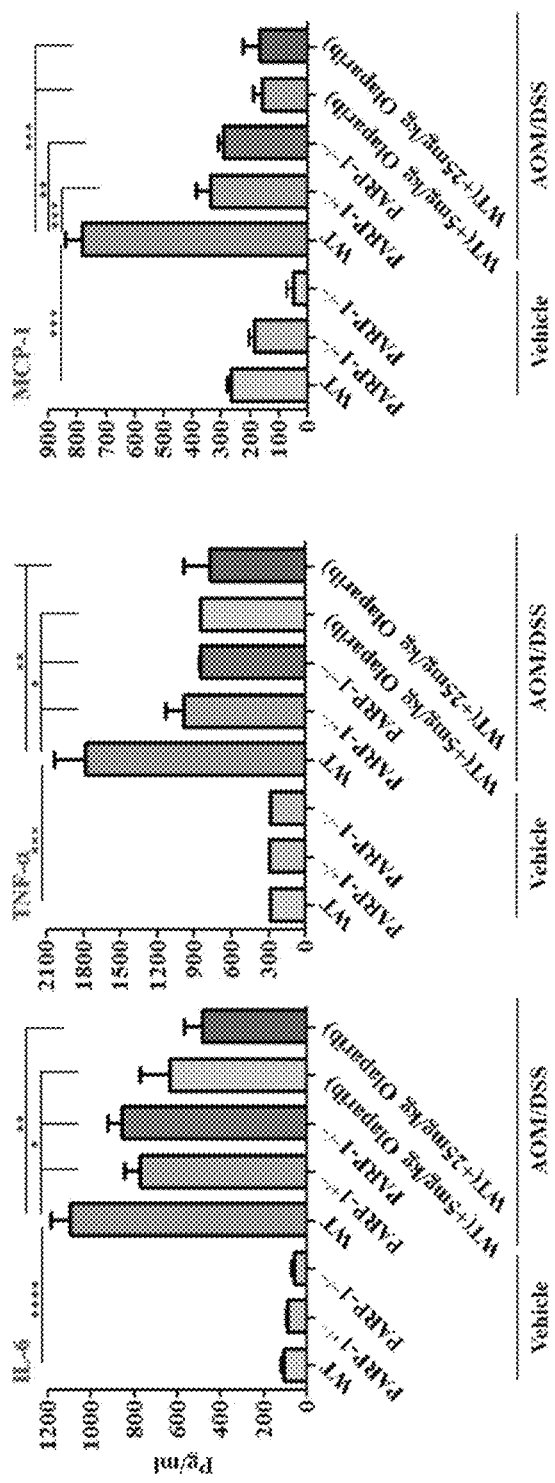

FIG. 4 shows PARP-1 inhibition reduces systemic inflammation in AOM/DSS-treated mice. Sera from the different experimental groups and controls were assessed for IL-6, TNF-a, and MCP-1 by ELISA.

Figure 5:
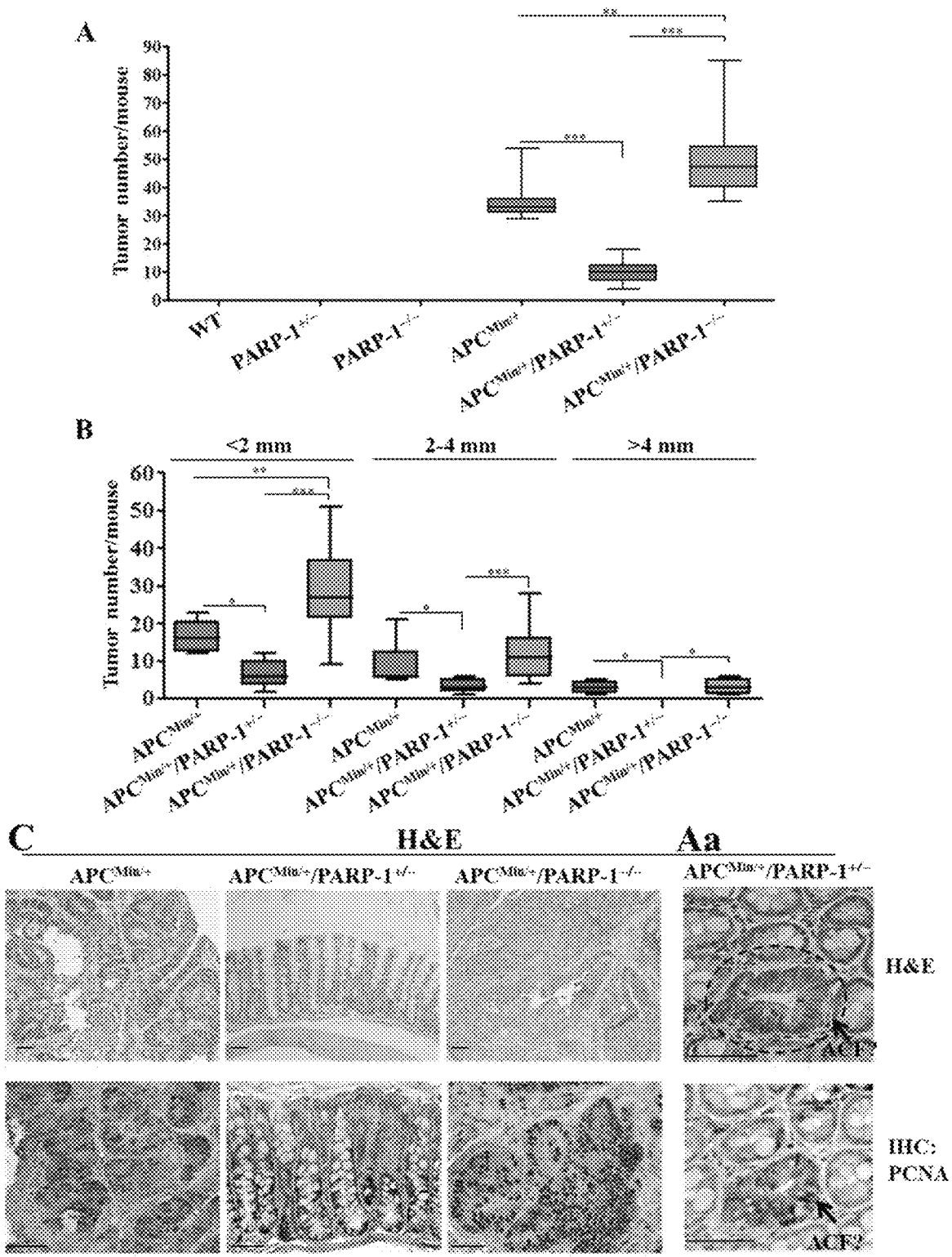

FIG. 5 shows partial inhibition of PARP-1 (by gene heterozygosity or olaparib) protects against, while complete inhibition (by gene knockout) aggravates, APC$^{Min}$-induced tumor burden in mice: No major connection with systemic inflammation. WT, PARP-1+/− or PARP-1−/− mice were bred into an ApcMin background and sacrificed at 16 weeks of age. (A) Tumor numbers along the intestinal track were assessed. Note the opposing effects of PARP-1 gene heterozygosity and knockout (B) Size of tumors was assessed and classified as small (<2 mm), medium (2-4 mm), or large (>4 mm). (C) H&E staining of tumors and immunohistochemical analysis with antibodies to PCNA, a marker of cell proliferation. (D) Five wk old ApcMin/+ mice were administered 5 mg/kg olaparib twice a week. Mice were sacrificed at 16 wks of age. Note the protective effect of olaparib. (E) Sera from the different experimental groups and controls were assessed for IL-6, TNF-a, and MCP-1 by ELISA. Note that all forms of PARP inhibition reduced TNF-a and MCP-1 but not IL-6.

Figure 6:
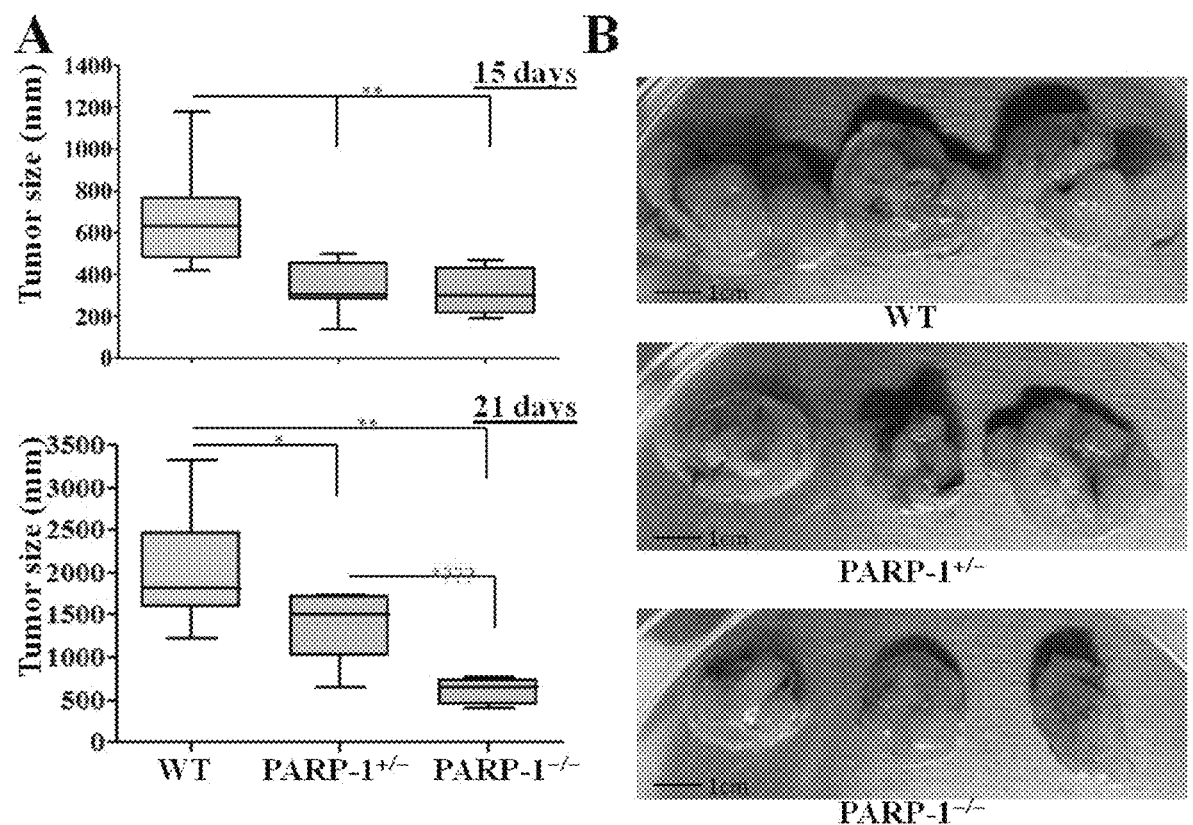

FIG. 6 shows PARP-1 inhibition provides a tumor-suppressive environment and reduces splenomegaly in MCA-38 cell-based allograft (immunocompetent) model of colon cancer. The colon adenocarcinoma cell line derived from a C57BL/6 mouse were engrafted subcutaneously into WT, PARP-1+/− or PARP-1−/− mice. (A) Tumor sizes were measured at different days (15 and 21 days are shown). (B) actual tumors isolated from the different mouse strains. Note that tumors developed in PARP-1+/− or PARP-1−/− mice were significantly smaller than those of WT mice.

Figure 7:
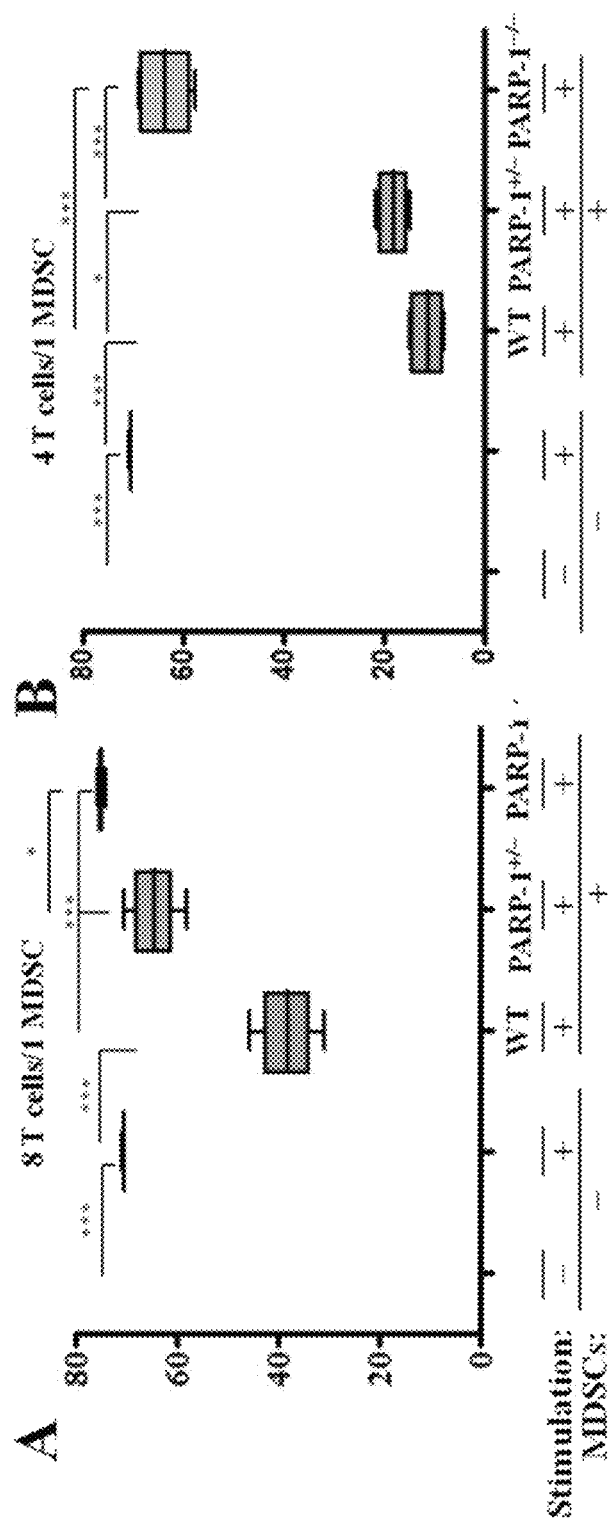

FIG. 7 shows PARP-1 inhibition by gene heterozygosity or knockout blocks the suppressive activity of MDSCs. Myeloid-derived suppressor cells (MDSCs) were isolated from tumors developed on WT, PARP-1+/− or PARP-1−/− mice. The MDSCs were then tested for their ability to suppress proliferation of CFSC-labeled WT T cells at a MDSC/T cell ratio of 8/1 or 4/1. Note that both PARP-1+/− and PARP-1−/− MDSCs failed to suppress T cell proliferation albeit PARP-1−/− cells showed the least suppression.

Figure 8:
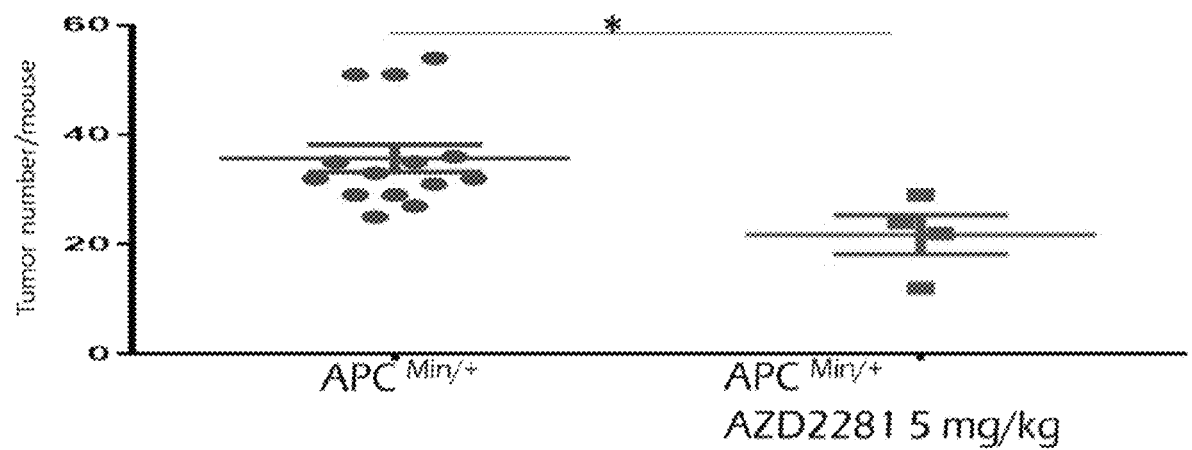

FIG. 8 shows Olaparib (5 mg/kg) reduces the tumor burden of the APCMin/+ mice. Mice received i.p. injections of AZD2281 twice a week for 11 weeks. The treatment was started at 5 weeks of age. Tumor burden was assessed at 16 weeks of age.

Figure 9:
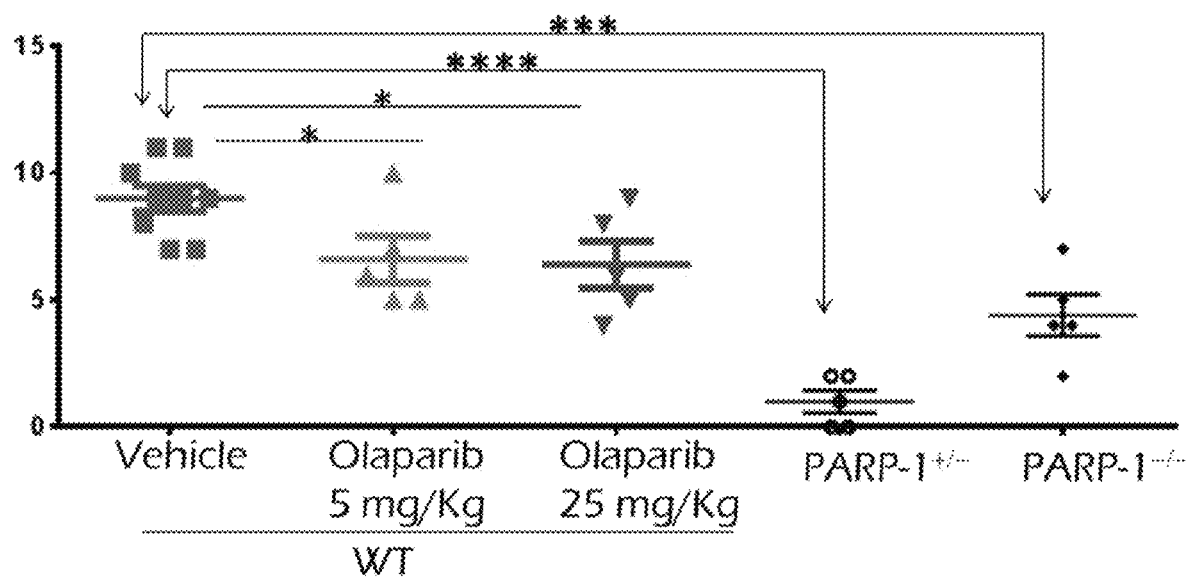

FIG. 9 shows tumor burden in mice treated with Olaparib. Mice received an i.p. injection of 10 mg/kg of AOM at 8 weeks of age. A week later, they were given 1.25% of DSS in drinking water for a week followed by two weeks of regular water. This DSS regimen was repeated 4 times. Two groups of WT received i.p. injections of AZD2281 twice a week at either low dose of 5 mg/kg or high dose at 25 mg/kg. All mice were sacrificed at the end of 21 weeks and were subjected to colon tumor burden count. Note that the most effective protection against the tumor burden was achieved by PARP-1 gene heterozygosity.

Figure 10:
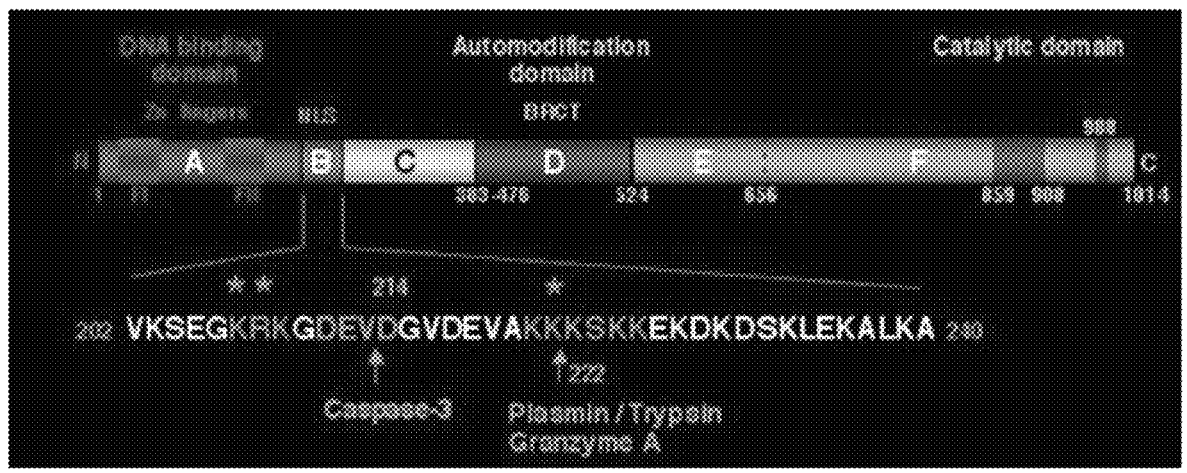
Figure 10:
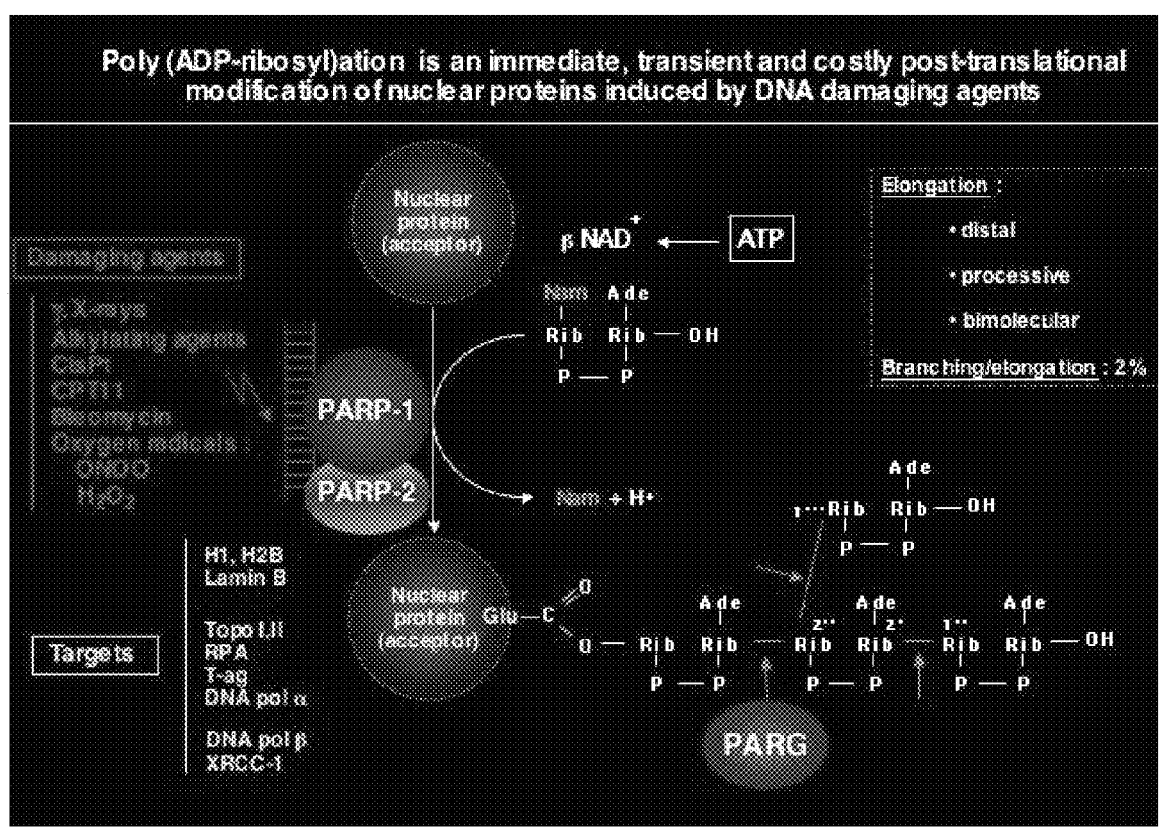

FIG. 10 shows Poly(ADP-ribose) polymerase-1 (PARP-1). FIG. 10 discloses SEQ ID NO: 19.

Figure 11:
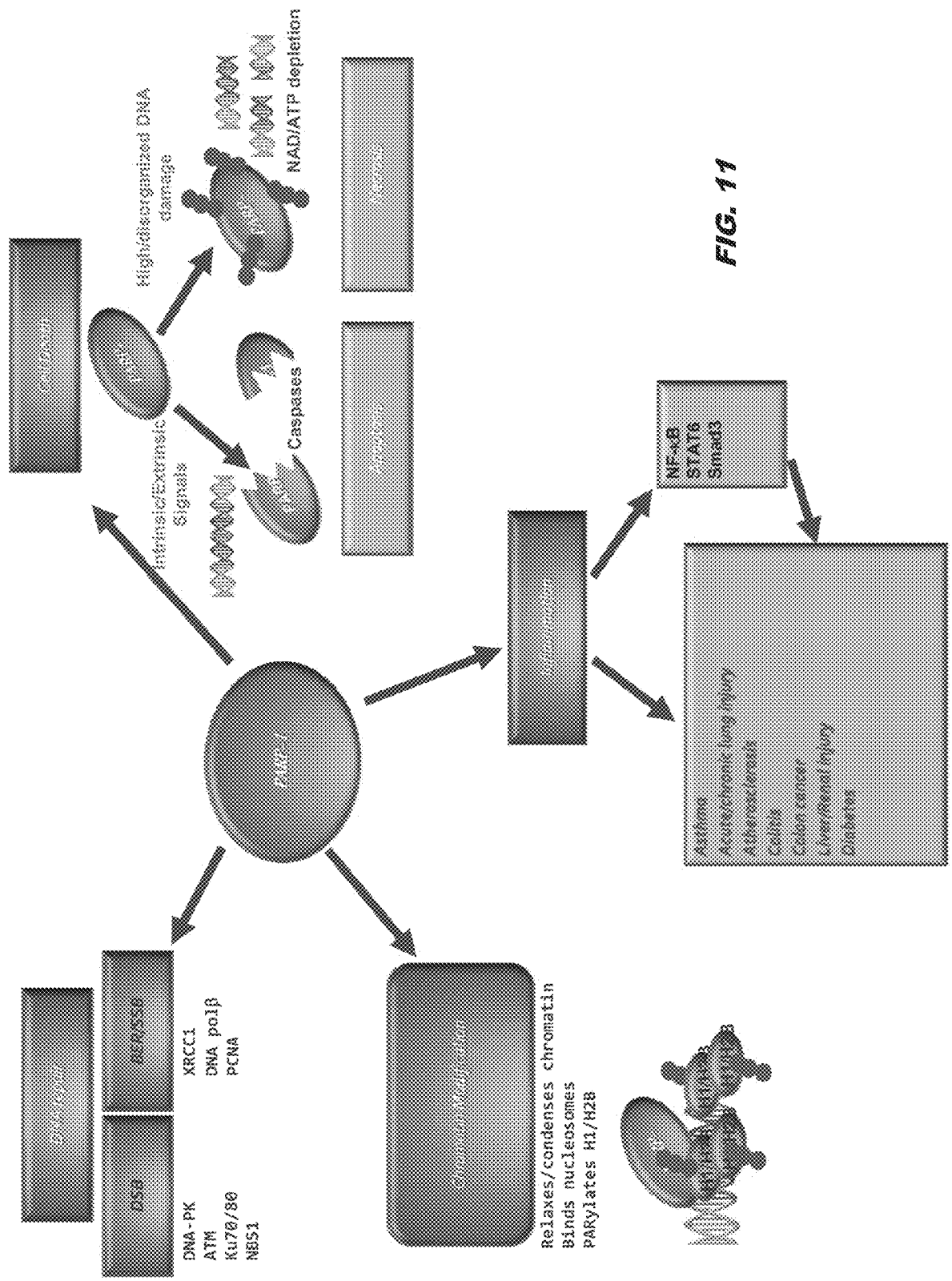

FIG. 11 shows exemplary processes in which PARP-1 is involved in. See *Cancers* 2013, 5(3), 943-958.

Figure 12:
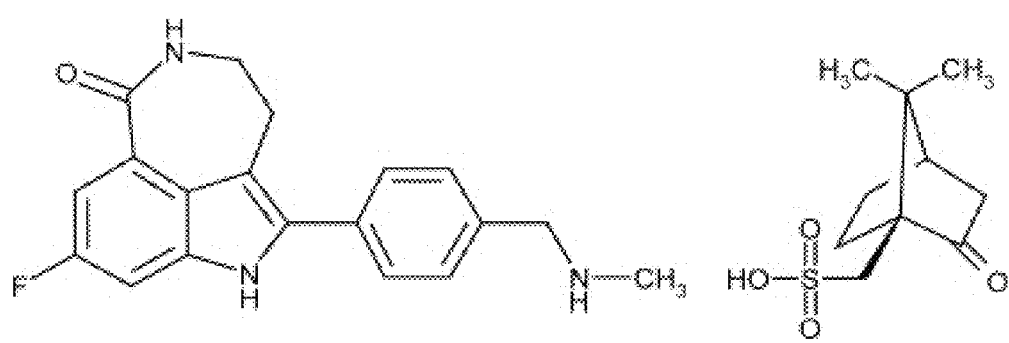
Figure 12:
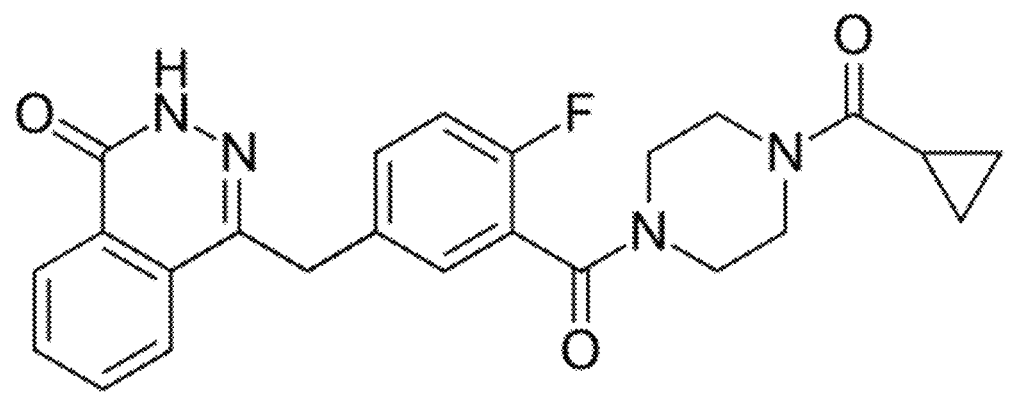

FIG. 12 shows chemical structure of (A) Rubraca and (B) Olaparib. Rubraca comes in tablet form—the starting dose is two 300-mg tablets, taken orally twice a day, with or without food.

Figure 13:
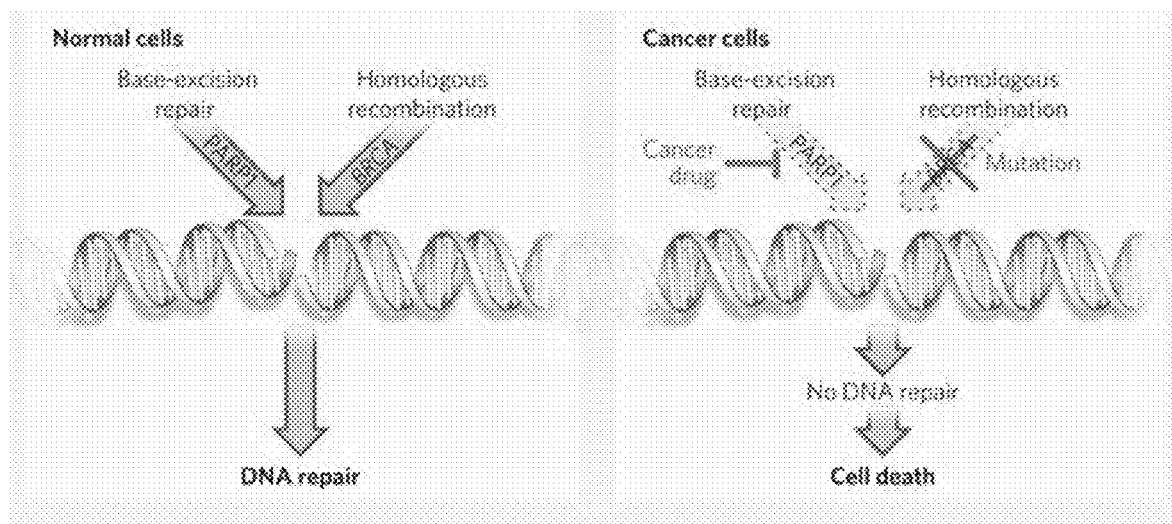

FIG. 13 shows the concept of synthetic lethality. Major issues with the strategy include continuous use of high doses of the drug (such as a minimum of 600 mg/day), and development of resistance.

Figure 14:
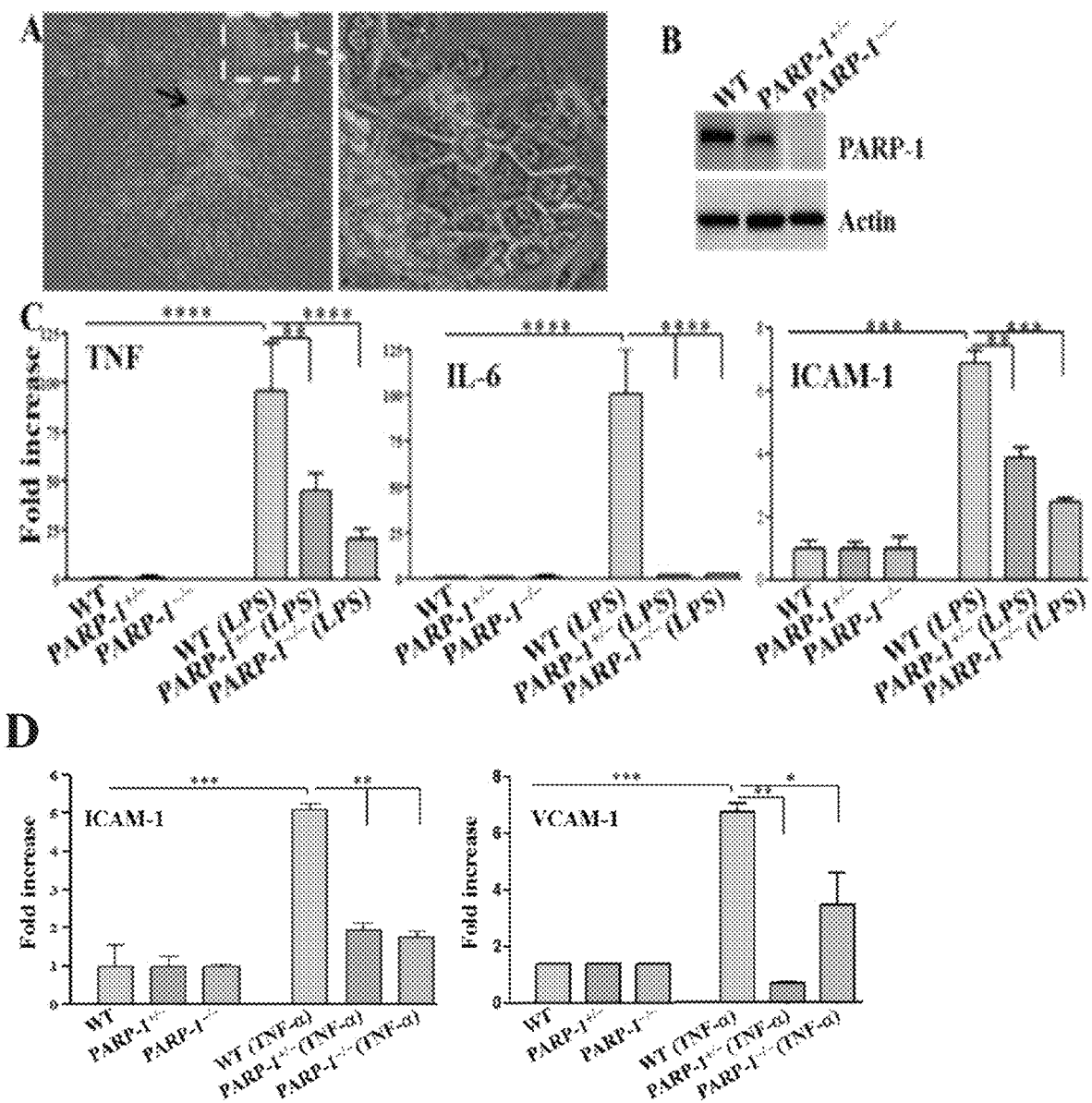

FIG. 14 shows partial PARP-1 inhibition is sufficient to block expression of inflammatory genes in primary colon epithelial cells. (A) Phase-contrast microscopy of a typical CEC colony emerging from a pure crypt (black arrow); the right panel is a higher magnification, demonstrating isolation of primary colon epithelial cells. (B) CECs were isolated from WT, PARP-1$^{+/-}$ or PARP-1$^{-/-}$ mice. Protein extracted were subjected to immunoblot analysis, demonstrating that gene heterozygosity reduces (only partially) expression of PARP-1, while knockout eliminates the protein completely. (C and D) CECs were treated with LPS (2 μg/ml) for 6 h or TNF after which RNA was extracted; cDNAs were subjected to real-time PCR using set of primers for mouse TNF, IL-6, ICAM-1, VCAM-1 or β-actin. Fold changes (ΔΔCT values) were then calculated using β-actin as a normalization control. *, $p \leq 0.05$; , $p \leq 0.01$; *, $p \leq 0.001$; ****, $p \leq 0.0001$, demonstrating that partial inhibition of PARP-1 by heterozygosity is sufficient to inhibit inflammation as shown by markers of inflammation such as TNF, and others.

Figure 15:
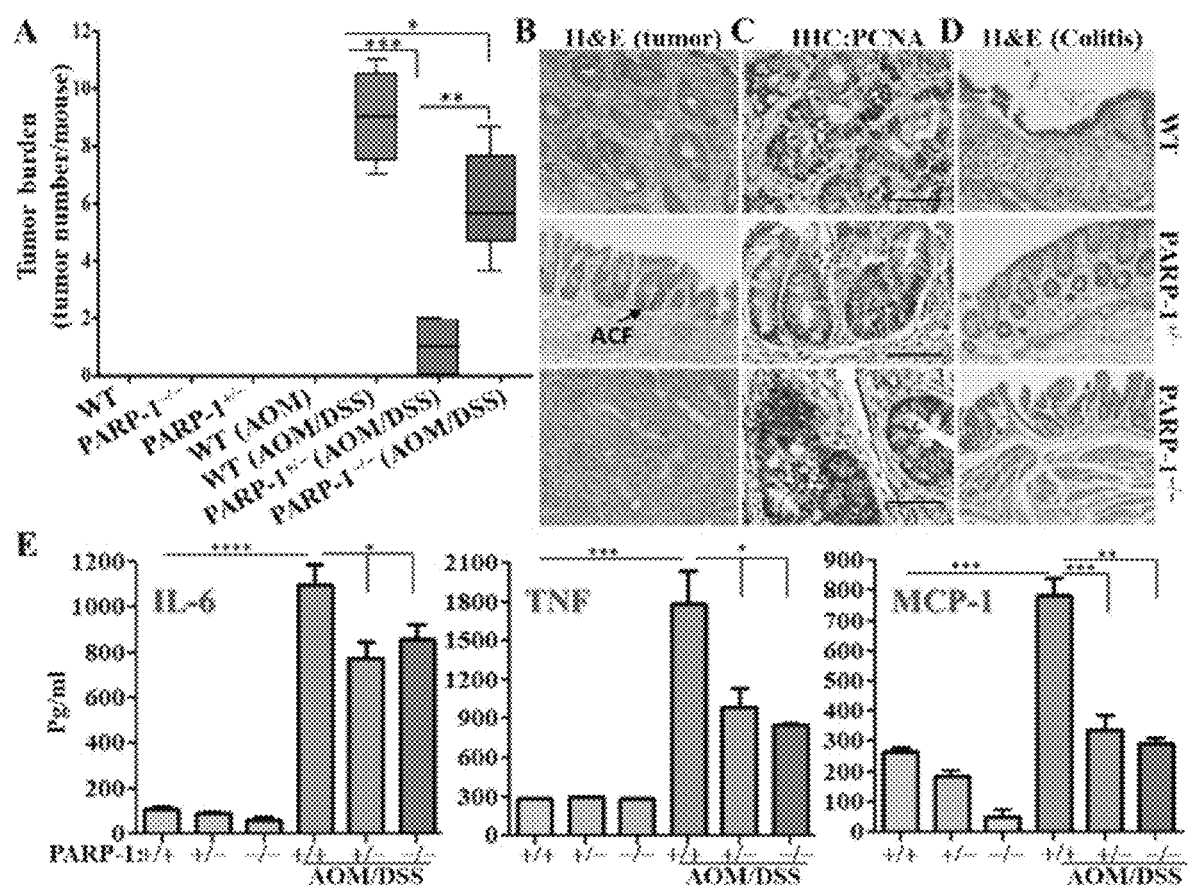

FIG. 15 shows partial inhibition of PARP-1 is more effective at reducing inflammation-driven colon tumorigenesis. WT, PARP-1$^{+/-}$ or PARP-1$^{-/-}$ mice received 10 mg/kg of AOM, i.p. once followed by 4 cycles of 2.5% DSS in drinking water. (A) At 21 weeks of age, mice were sacrificed and colon tumor burden was counted. (B) H&E staining of colon tumor sections. (C) IHC with an anti-PCNA antibody. (D) H&E staining showing the protective effective of PARP-1$^{+/-}$ and PARP-1$^{-/-}$ against AOM/DSS-induced colitis. (E) Sera were assessed for IL-6, TNF or MCP-1 using sandwich ELISA. *, $p \leq 0.05$; , $p \leq 0.01$; *, $p \leq 0.001$; ****, $p \leq 0.0001$.

Figure 16:
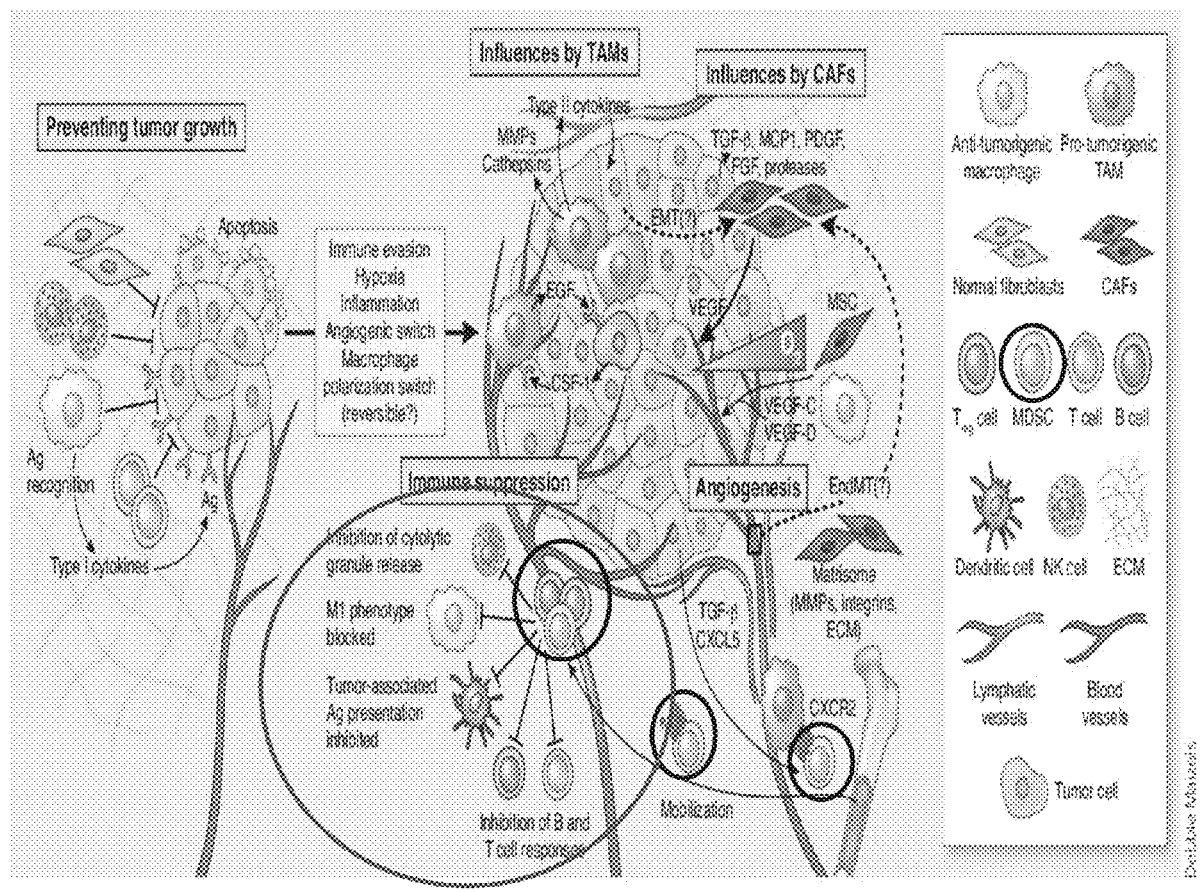

FIG. 16 shows involvement of immune cells in tumor microenvironment and tumorigenesis.

Figure 17:
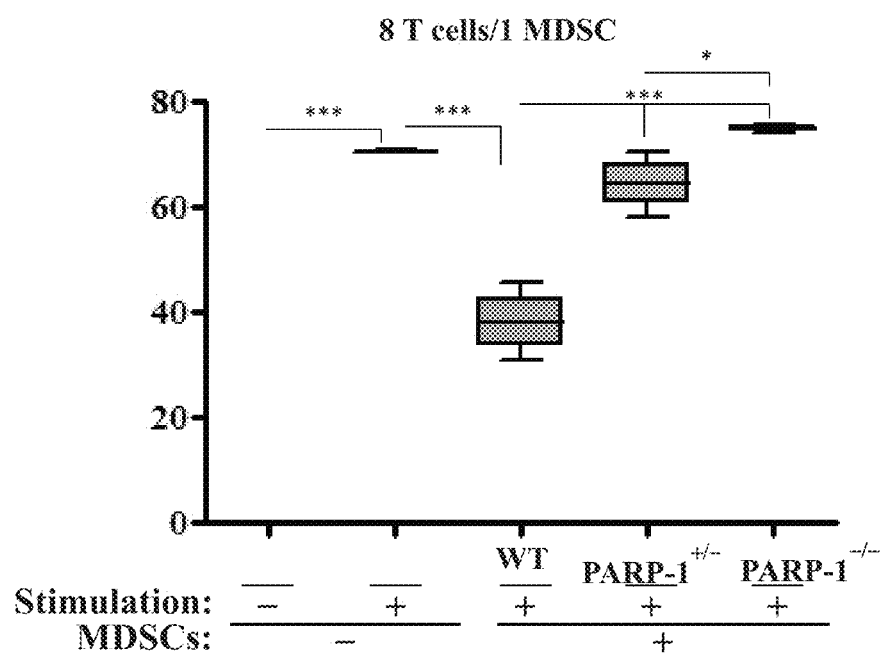
Figure 18:
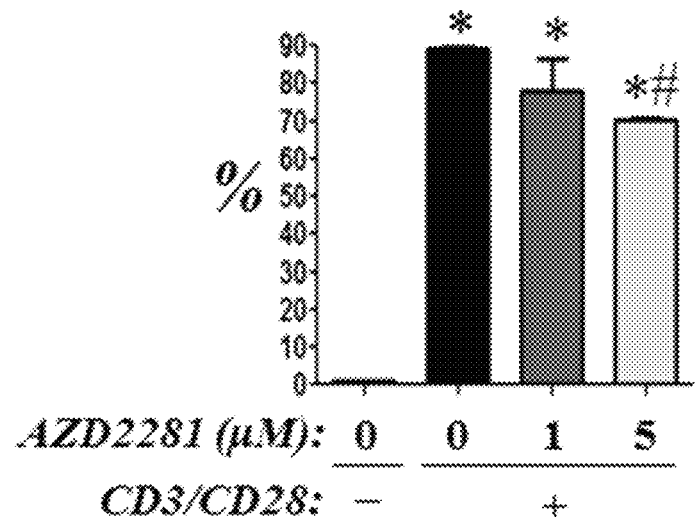
Figure 18:
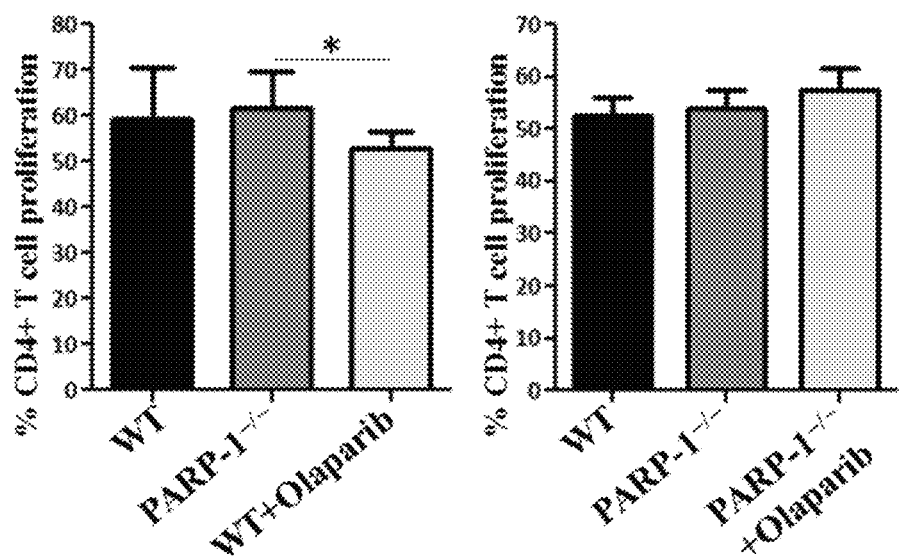

FIG. 17 shows PARP-1 inhibition by gene heterozygosity or knockout blocks the suppressive activity of MDSCs FIG. 18 shows PARP-1 inhibition does not interfere with T or dendritic cell function. Further, see J Immunol Jun. 15, 2006, 176 (12) 7301-7307.

Figure 19:
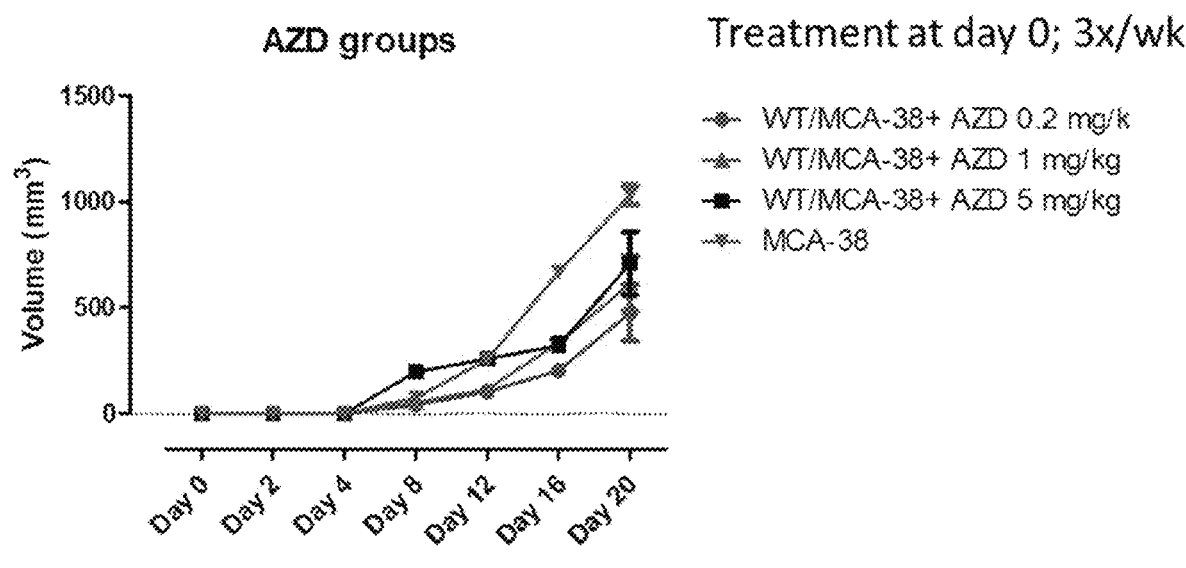
Figure 20:
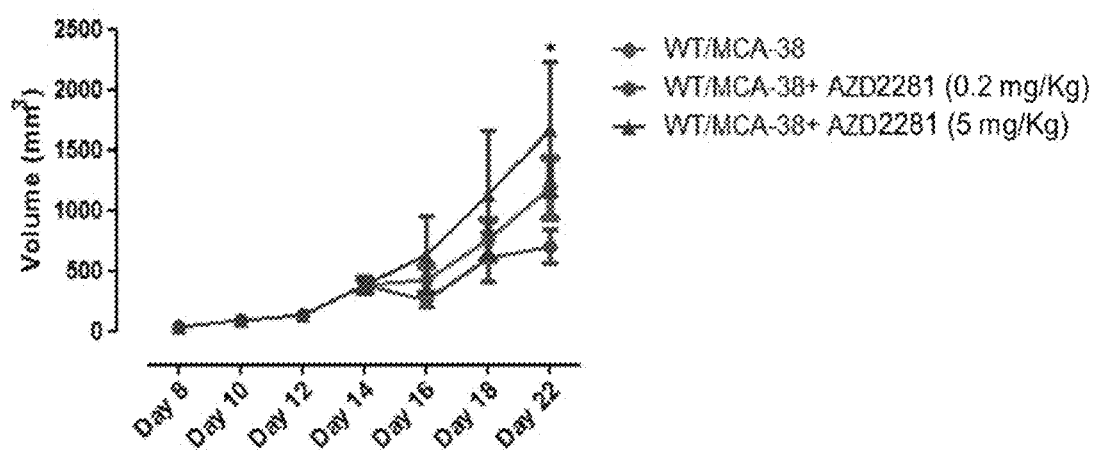
Figure 21:
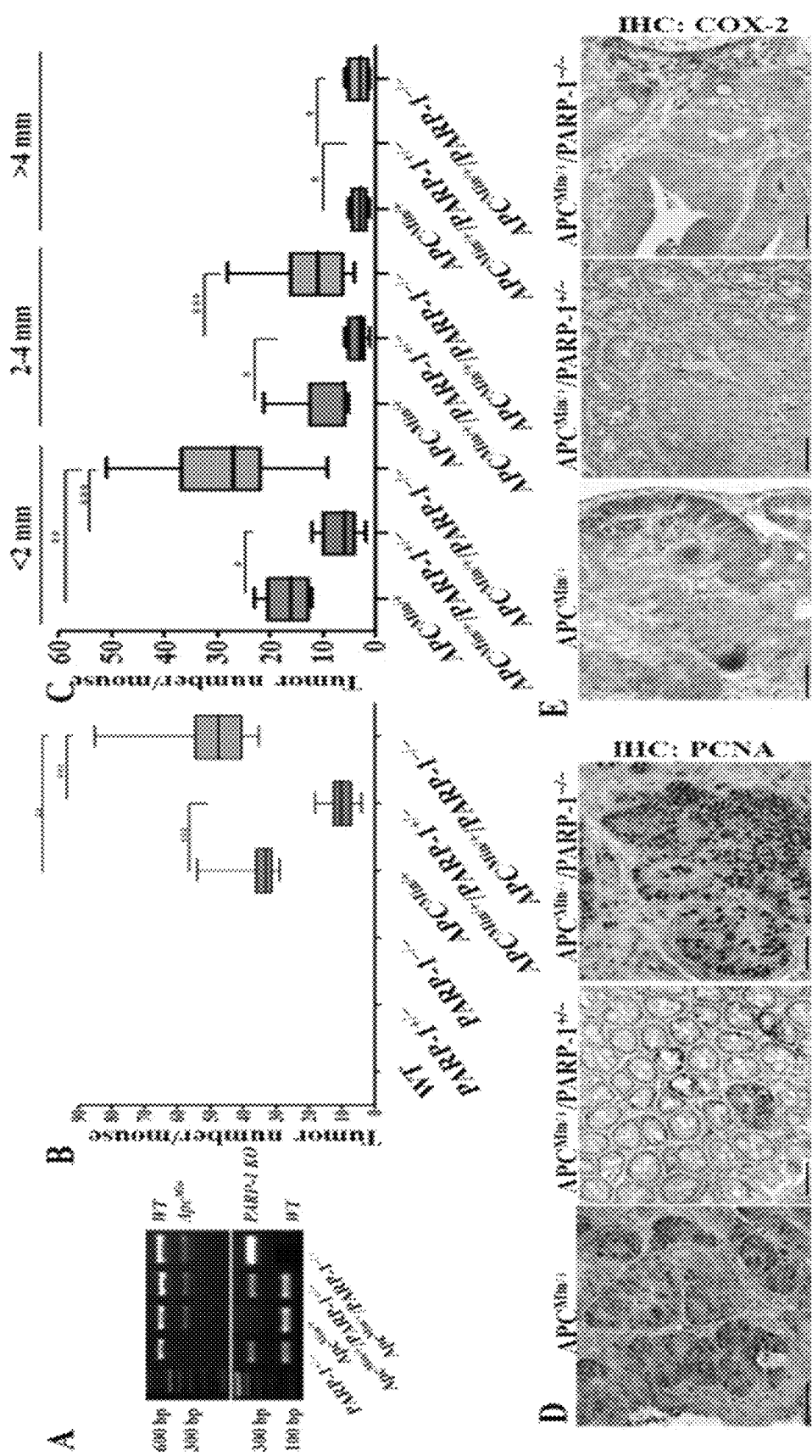

FIG. 19 shows Low dose of a PARP inhibitor is as effective as a high dose in blocking colon cancer when administered at a very early stage FIG. 20 shows Low dose of a PARP inhibitor is much more effective than the high dose in blocking colon cancer when administered after a clear development of tumors FIG. 21 shows (A) A sample of genotyping: Bands representing WT APC or APC$^{Min}$(top panel) or WT PARP-1 or KO (bottom panel). Genotype of the mice is displayed below the panels. (B) Tumor numbers were counted at 16-week-old of age in APC$^{Min/+}$, APC$^{Min/+}$/PARP$^{+/-}$, and APC$^{Min/+}$/PARP$^{-/-}$ mice (per group>10 mice). (C) Tumor burden was analyzed based on size and divided in groups lower than 2 mm, 2-4 mm, and tumors bigger than 4 mm. Colon tumor sections from were subjected to immunohistochemistry (IHC) with antibodies specific to PCNA (D) or COX-2 (E). *, p≤0.05; , p≤0.01; *, p≤0.001; ****, p≤0.0001.

Figure 22:
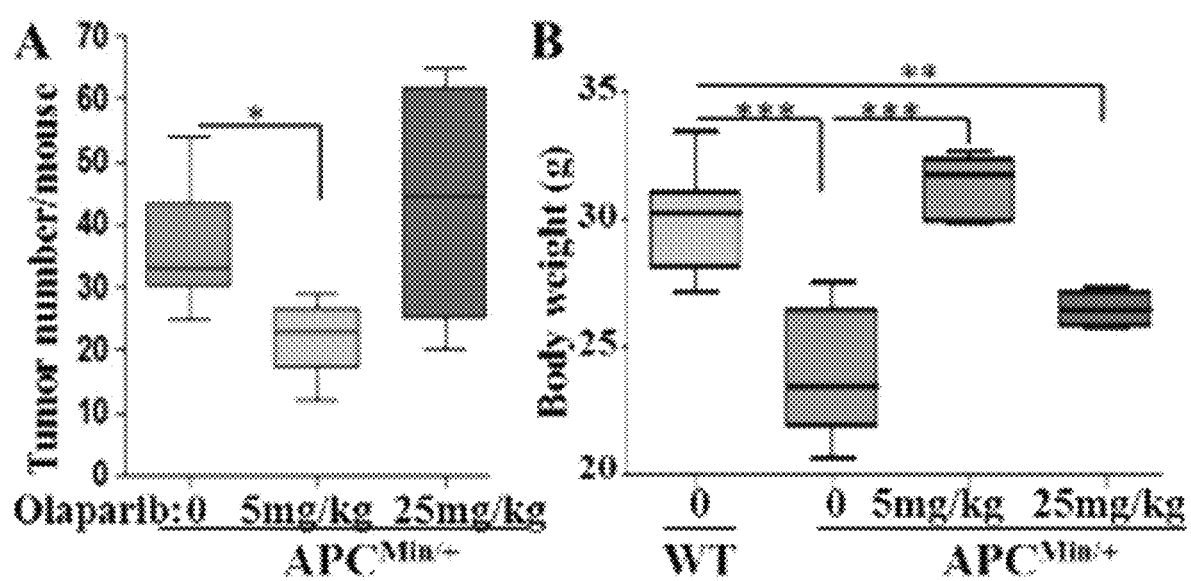

FIG. 22 shows APC$^{Min/+}$ mice were randomized into 3 groups and received, i.p., 5 mg/kg of olaparib (0.005% DMSO in saline), 25 mg/kg of the drug twice a week, or vehicle from 5 weeks up to 16 weeks of age. Mice were then sacrificed and tumor burden was quantified. (B) Weight of mice from the different groups at 16 weeks of age. *, p≤0.05; , p≤0.01; *, p≤0.001.

Figure 23:
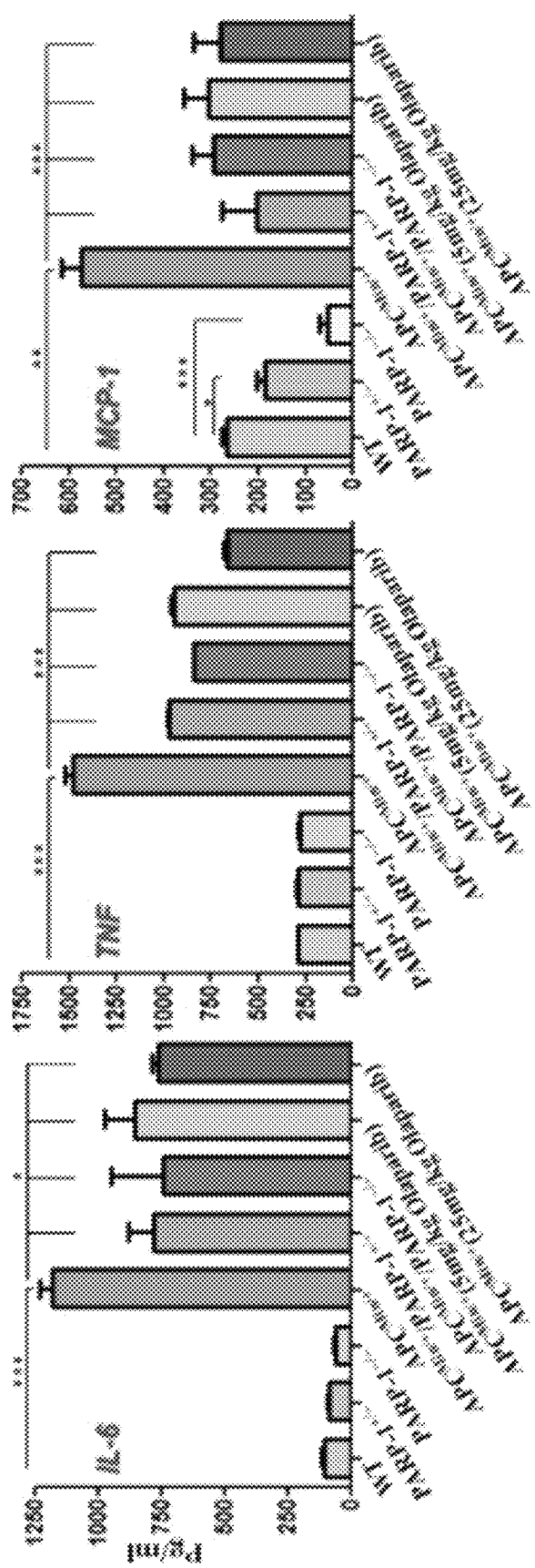

FIG. 23 shows sera from the different mouse groups were assessed for IL-6, TNF or MCP-1 using sandwich ELISA according to manufacturer's instructions.

Figure 24:
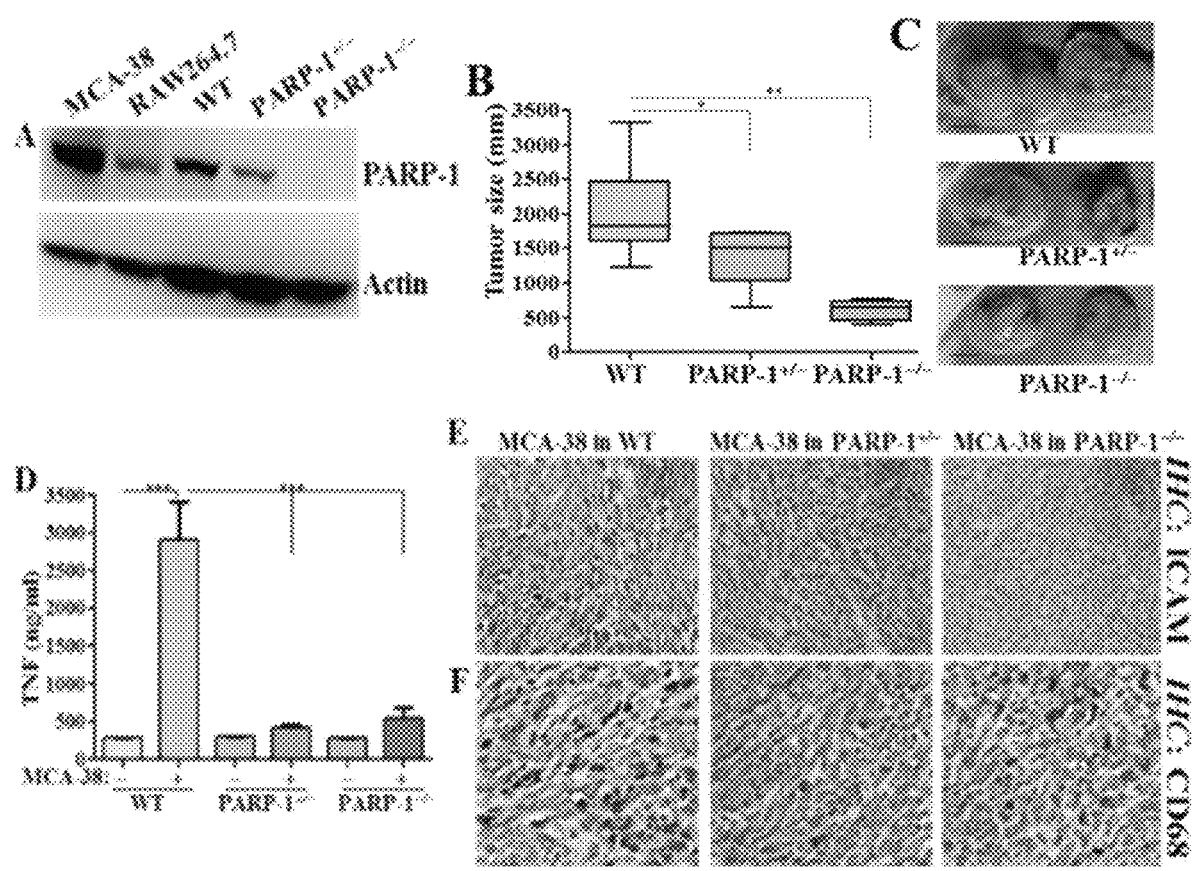

FIG. 24 shows (A) Protein extracts from MCA-38 cells, RAW264.7 cells, or colon epithelial cells derived from WT, PARP-1$^{+/-}$, or PARP-1$^{-/-}$ mice were subjected to immunoblot analysis. MCA-38 cells (2.5×10$^5$) were injected subcutaneously into the left flank of WT, PARP-1$^{+/-}$, or PARP-1$^{-/-}$ mice. (B) Tumor sizes were measured at day 15. (C) Images of two representative tumors isolated from the different groups. Bar=1 cm. (D) Sera from the different mouse groups were assessed for TNF by ELISA as above. Tissue sections from MCA-38-generated tumors were subject to IHC with antibodies to ICAM-1(E) or CD68, a macrophage marker (F). For (B) and (D): *, p≤0.05; , p≤0.01; *, p≤0.001.

Figure 25:
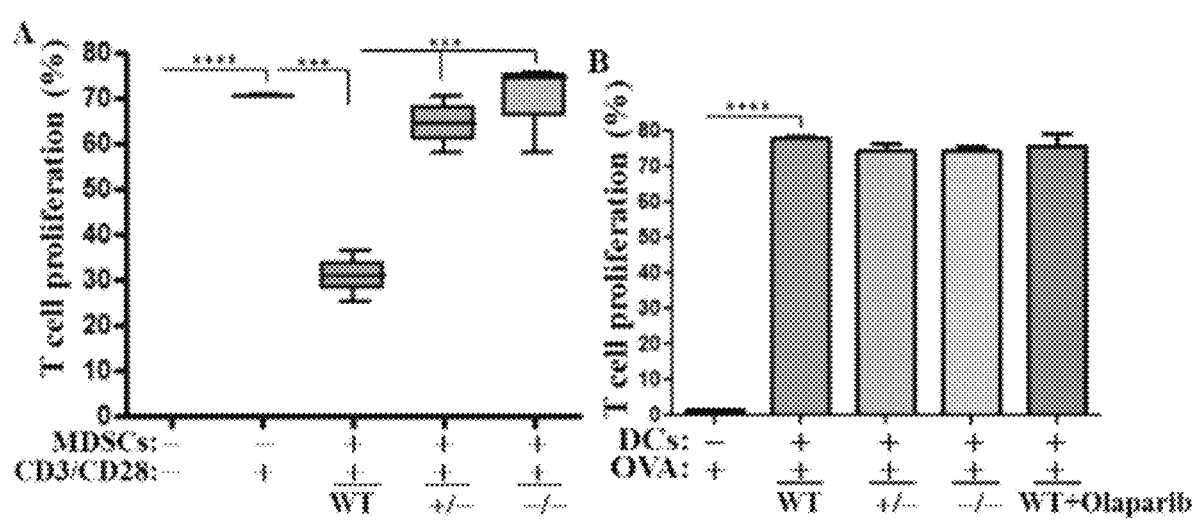

FIG. 25 shows (A) MDSCs derived from tumors of WT, PARP-1$^{+/-}$ or PARP-1$^{-/-}$ mice (n=4 for each group) were assessed for their ability to suppress proliferation of CFSC-labeled WT T cells at a MDSC/T cell ratio of 1:8. (B) Bone marrow (BM)-derived DCs were incubated with 10 ng/ml GM-CSF for 8 days; some WT DCs were cultured in the presence of 1 μM olaparib (spiked every 2 days). CD11c$^+$ cells were co-cultured with CFSE-labeled CD4$^+$ T cells from OTII mice. T cell proliferation was assessed by FACS. *, p≤0.05; , p≤0.01; *, p≤0.001.

Figure 26:
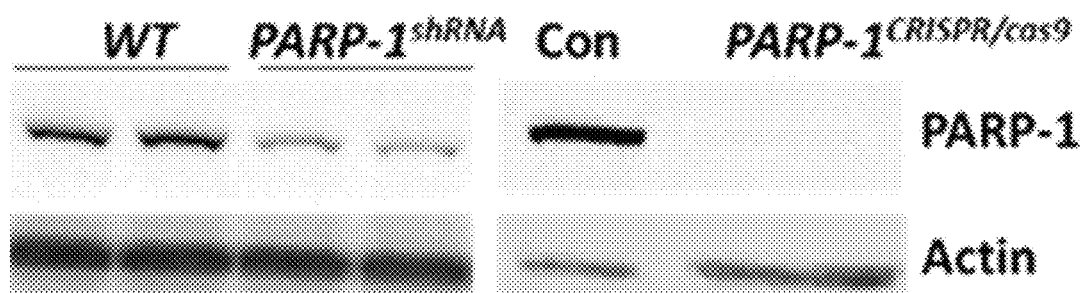

FIG. 26 shows A549 cells were subjected to knockdown using a lentiviral vector encoding a shRNA or to a CRISPR/Cas9 plasmid system (Santa Cruz) targeting PARP-1 and their respective controls. After selection, protein extracts were subjected to immunoblot analysis with antibodies to PARP-1 or actin.

Figure 27:
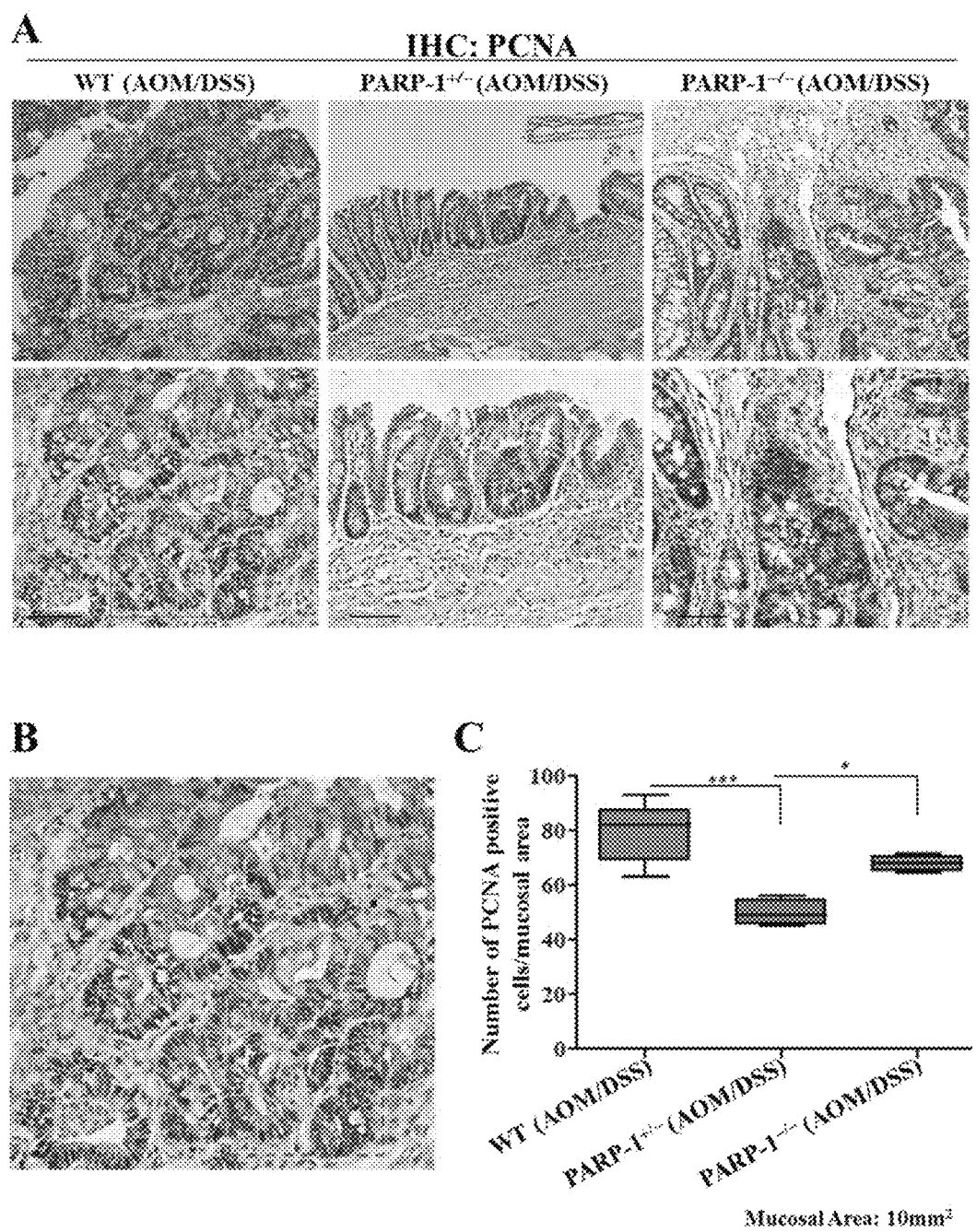

FIG. 27 shows high PCNA immunoreactivity (a marker of cell proliferation) was detected in tumors of AOM/DSS-treated WT and PARP-1$^{-/-}$ mice, which was much lower in tumors of treated PARP-1$^{+/-}$ mice (p<0.001).

Figure 28:
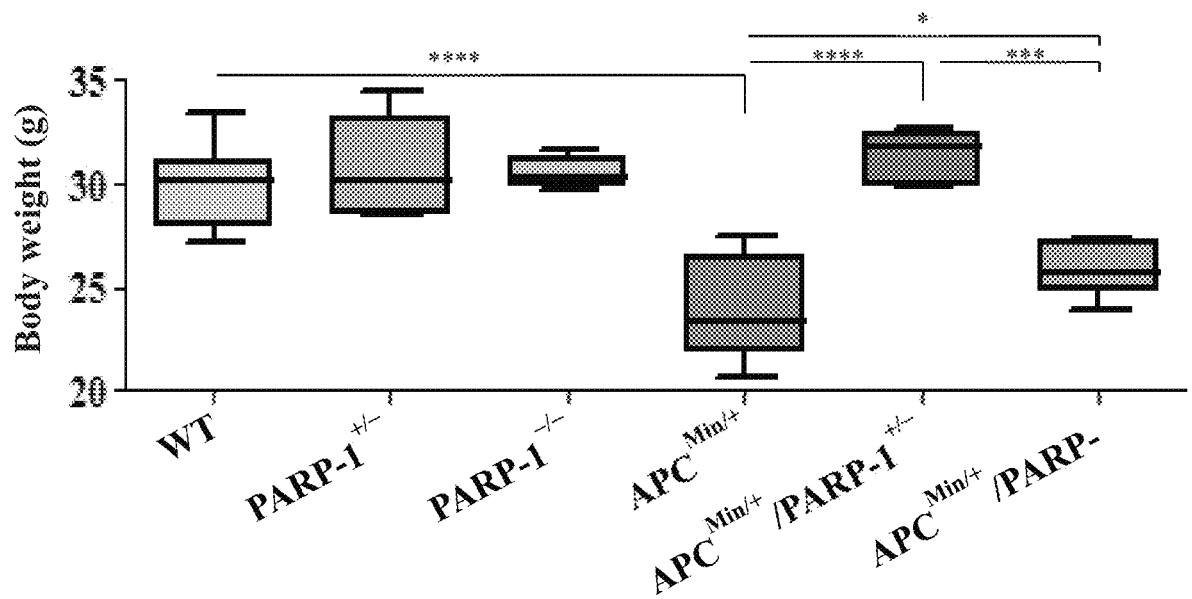

FIG. 28 shows weight loss observed in the APC$^{Min/+}$ mice was prevented by PARP-1 heterozygosity but not KO (FIG. 28).

Figure 29:
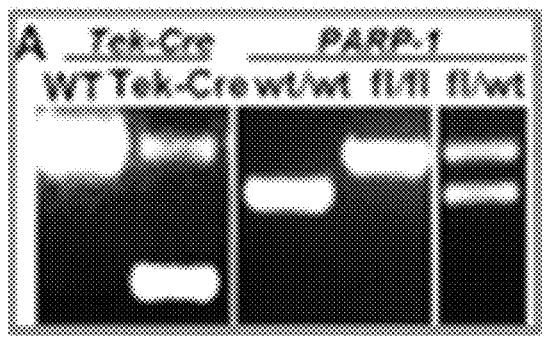

FIG. 29 shows representative PCR products showing the genotype of the different mouse strains.

Figure 30:
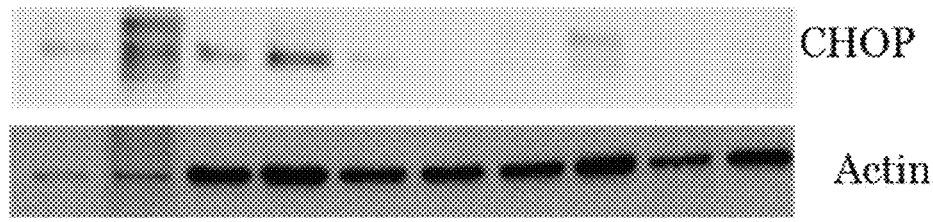
Figure 30:
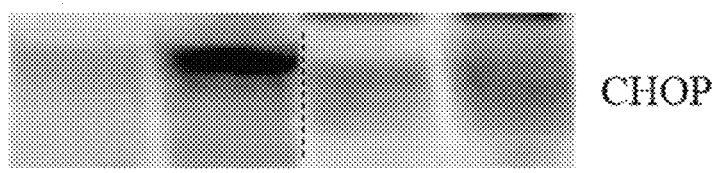

FIG. 30 shows (A) primary macrophages were isolated from WT or PARP-1$^{-/-}$ mice. Cells were then incubated either for 12 or 24 h in the presence or absence of the indicated concentration of oxLDL. Protein extracts were prepared from then collected cells the subjected to immunoblot analysis with antibodies to CHOP or Actin. (B) RAW cells (mouse macrophage cell line) were treated with 10 mg/ml oxLDL for 6 h in the presence or absence of 1 mM of the PARP inhibitor TIQ-A. Protein extracts were prepared from the collected cells then subjected to immunoblot analysis with antibodies to CHOP.

Figure 31:
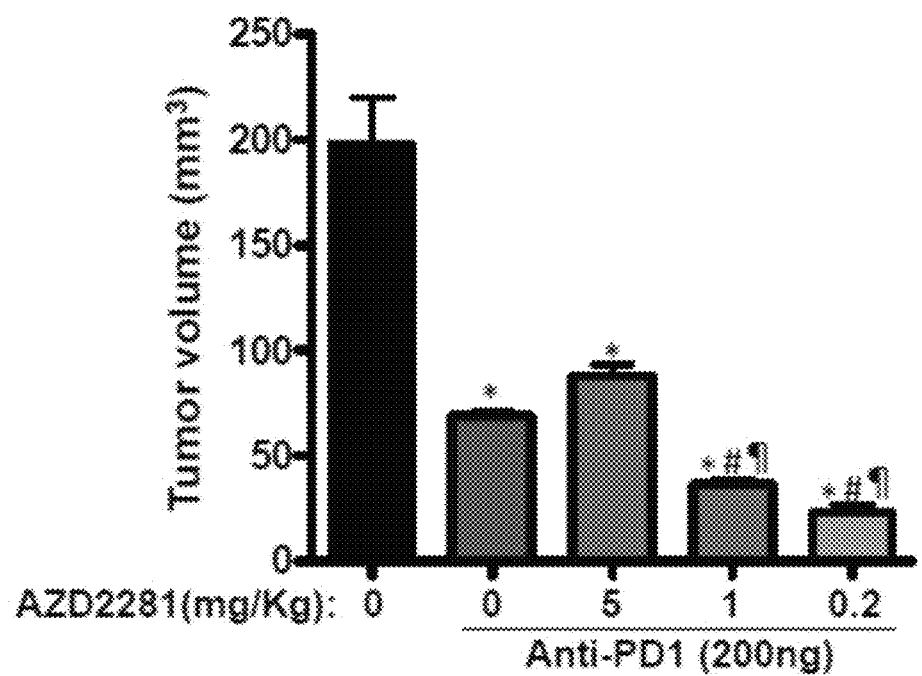

FIG. 31 shows that (A) PARP inhibition my also enhance the antitumor effects of low dose of PARP inhibitor compared to higher dose, and that (B) this effect may be due to increased infiltration of cytotoxic CD8+ T-cells in the tumor microenvironment.

Figure 32:
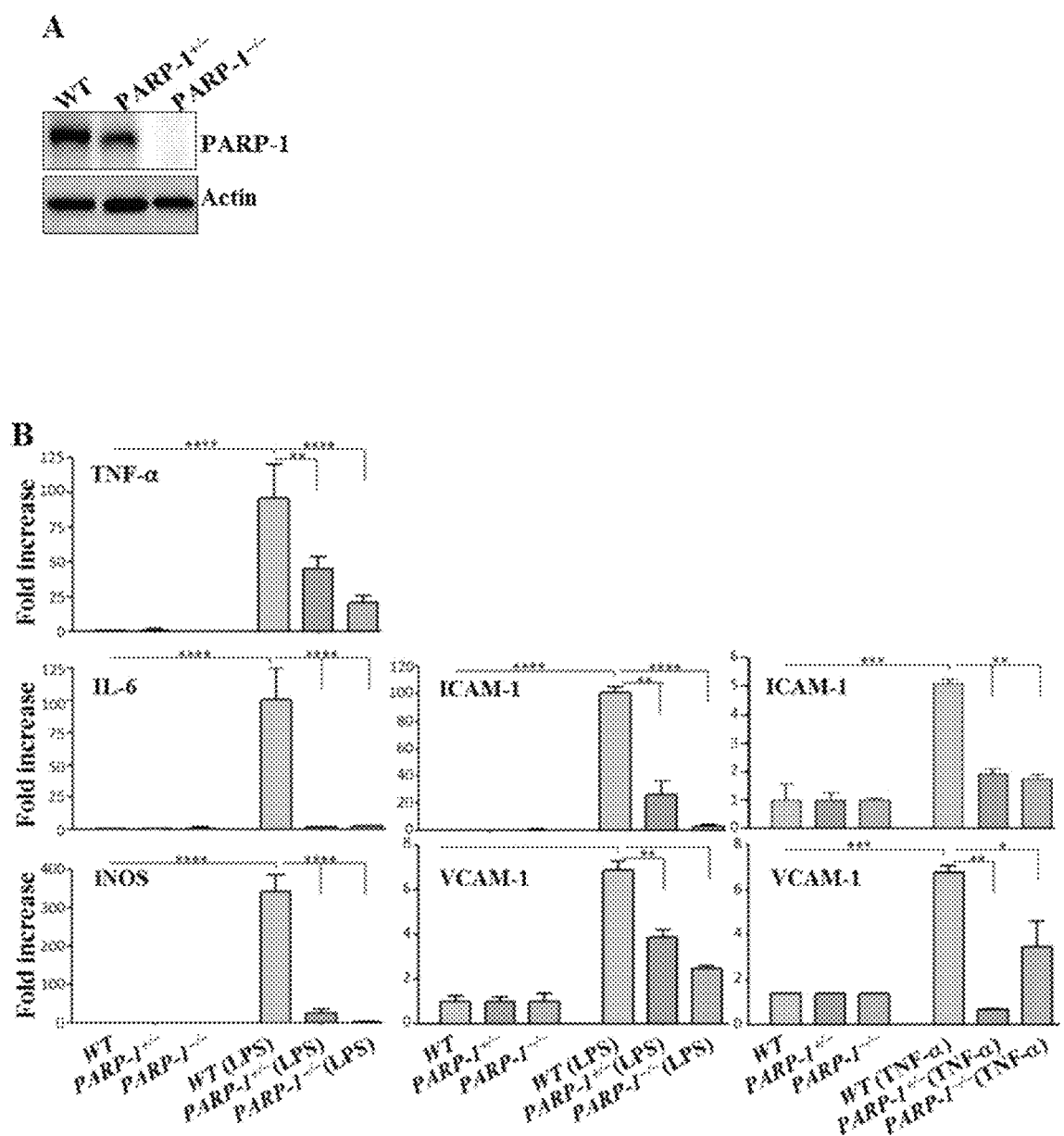

FIG. 32 shows partial PARP-1 inhibition is sufficient to block chronic inflammation and associated colon tumorigenesis. (A) CECs were isolated from WT, PARP-1$^{+/-}$ or PARP-1$^{-/-}$ mice. Total protein extracts were subjected to immunoblot analysis with antibodies to PARP-1 or actin. (B) CECs were treated with 2 μg/ml LPS or 10 ng/ml TNF-α for 6 h after which RNA was extracted; cDNAs were subjected to real-time PCR using sets of primers for mouse TNF-α, IL-6, ICAM-1 or β-actin. Fold changes (ΔΔCT values) were then calculated using β-actin as a normalization control. (C) WT, PARP-1$^{+/-}$ and PARP-1$^{-/-}$ mice received 10 mg/kg of AOM, i.p. once followed by 4 cycles of 1.25% DSS in drinking water. At 21 weeks of age, mice were sacrificed and colon tumor burden was assessed. (D) H&E staining of colon tumor sections from the different experimental groups. (E) IHC with antibodies to PCNA. (F) H&E staining showing the protective effect of PARP-1 gene heterozygosity and knockout against AOM/DSS-induced colitis. (G) WT mice were subjected to AOM/DSS protocol as described above. Mice from all experimental groups received i.p injections of 5 or 25 mg/kg olaparib or a vehicle twice a week immediately after AOM administration and until a day prior to sacrifice (21 weeks). Colon tumor numbers were counted. (H) H&E staining showing the protective effect of PARP-1 inhibition by olaparib against AOM/DSS-induced colitis. (I) Sera from the different experimental groups were assessed for IL-6, TNF-α or MCP-1 using sandwich ELISA. For (B), (C), (G), and (I), *, p≤0.05; , p≤0.01; *, p≤0.001; ****, p≤0.0001. Bar=50 μm.

Figure 33:
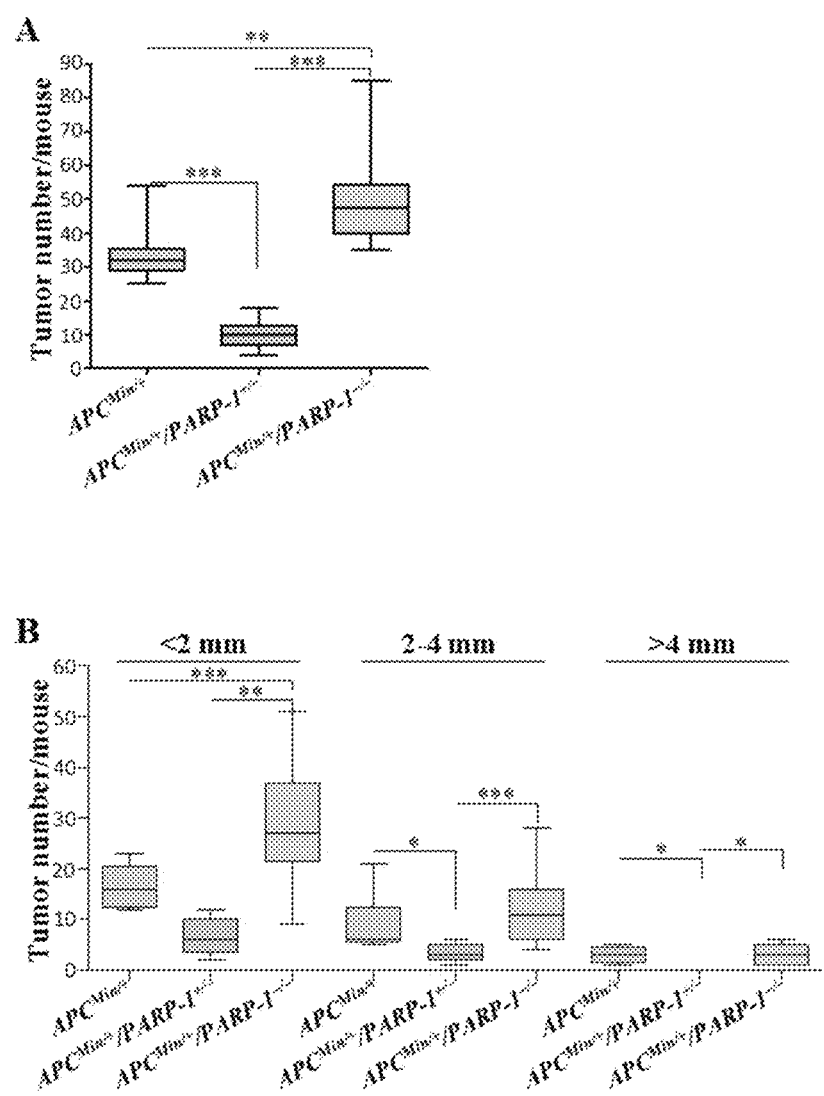

FIG. 33 shows partial inhibition of PARP-1 protects, while complete inhibition is ineffective, against APC$^{Min}$-induced tumor burden in mice. (A) APC$^{Min/+}$, APC$^{Min/+}$ PARP-1$^{+/-}$, and APC$^{Min/+}$ PARP-1$^{-/-}$ mice (per group>10 mice) were sacrificed at 16 weeks of age. Tumor numbers were then counted. (B) Tumor burden was analyzed based on size and divided in groups lower than 2 mm, 2-4 mm, and tumors bigger than 4 mm. Colon tumor sections from the 3 different groups were subjected to immunohistochemistry (IHC) with antibodies specific to PCNA (C) or COX-2 (D). (E) APC$^{Min/+}$ mice were randomized into 3 groups and received, i.p., 5 or 25 mg/kg olaparib twice a week, or vehicle (0.005% DMSO in saline) from 5 weeks up to 16 weeks of age. Mice were then sacrificed and tumor burden was quantified. Total body (F) or spleen (G) weight of mice from the different groups at 16 weeks of age. (F) Sera from the different mouse groups were assessed for TNF-α, IL-6, or MCP-1 using sandwich ELISA. For (A), (B), (E-H), *, p≤0.05; , p≤0.01; *, p≤0.001; ****, p≤0.0001. *, p≤0.05; , p≤0.01; *, p≤0.001. Bar=50 μm.

Figure 34:
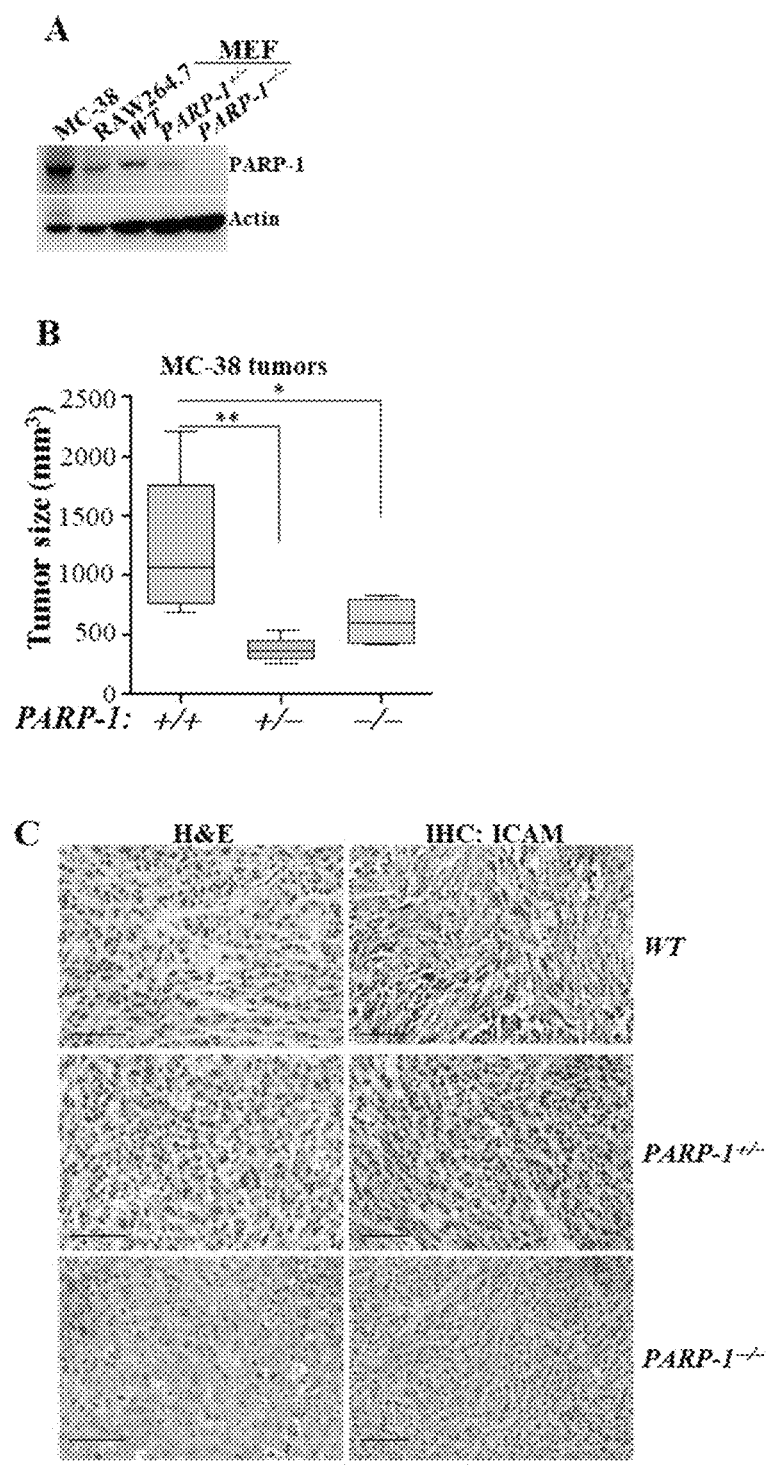

FIG. 34 shows a metronomic dose of olaparib or PARP-1 heterozygosity are sufficient to promote a tumor-suppressive environment in a syngeneic colon cancer mouse model. (A) Protein extracts from MC-38 cells, RAW264.7 cells, or mouse embryonic fibroblasts derived from WT, PARP-1$^{+/-}$, or PARP-1$^{-/-}$ mice were subjected to immunoblot analysis. (B) MC-38 cells ($2.5 \times 10^5$) were injected s. c. into the left flanks of WT, PARP-1$^{+/-}$ or PARP-1$^{-/-}$ mice. Tumor sizes were measured at day 21. (C) Mice were sacrificed and tumor sections were subjected to H&E (left panels) or IHC straining (right panels) with antibodies to ICAM-1. (D) Spleen weight of mice from the different groups. (E) MC-38 cells were engrafted onto WT mice. When tumors became palpable (day 4-6), mice received different doses of olaparib or vehicle. Tumor volume was measured at the indicated days. (F) Mice were sacrificed at day 24 and tumor sections were subjected to IHC straining with antibodies to ICAM-1. (G) Sera from the different mouse groups were assessed for TNF-a, IL-6 or MCP-1 by ELISA. (H) Protein extracts from tumors derived from the different experimental groups were subjected to immunoblot analysis with antibodies to cleaved (active) caspase-3, caspase-7 or H3 as a loading control. For (B), (D-E), and (G): *, $p \le 0.05$; , $p \le 0.01$; *, $p \le 0.001$. Bar=50 µm.

Figure 35:
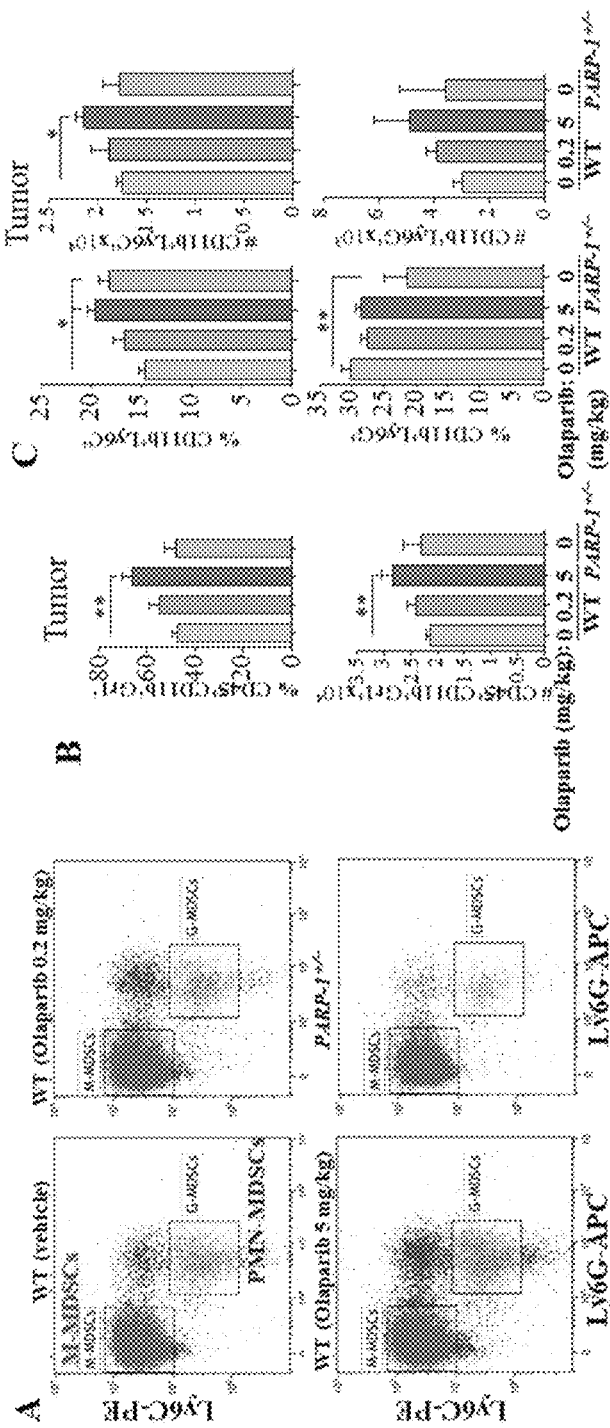

FIG. 35 shows the suppressive function of MDSCs is highly sensitive to PARP inhibition. Tumors from the different experimental groups were either processed to generate single-cell suspensions or fixed with formalin. Single cell suspensions were stained with a combination of antibodies to CD45, CD11b, Gr1, Ly6C, and Ly6G. CD11b$^+$ cell population was gated from the live CD45$^+$ population. (A) Representative FACS dot plot of the experimental groups. (B) Absolute numbers and percentages of CD11b$^+$Gr1$^+$ cell populations in tumors of the different groups. (C) Absolute numbers and percentages of CD11b$^+$Ly6C$^+$ and CD11b$^+$Ly6G$^+$ populations in tumors of the different groups. (D) Absolute numbers and percentages of CD45$^+$CD3$^+$ and CD3$^+$CD8$^+$ cell populations in tumors of the different groups. (E) Serial sections of tumors from WT mice that were treated with 0.2 or 5 mg/kg olaparib or vehicle or PARP-1$^{+/-}$ mice were subjected to IHC (left panels) or immunofluorescence (right panels) with antibodies to mouse Gr1 or CD8. (F) Percentages of CD45$^+$CD3$^+$ and CD3$^+$CD8$^+$ cell populations in spleens of the different groups. (G) CD11b$^+$-enriched MDSCs isolated from tumors of WT mice that were treated with 0.2 or 5 mg/kg olaparib or vehicle or PARP-1$^{+/-}$ mice were assessed for their ability to suppress proliferation of CD3/CD28-stimulated and CFSC-labeled WT CD3$^+$ T cells at a MDSC/T cell ratio of 1:8. T cell proliferation was assessed by FACS. *, $p \le 0.05$; , $p \le 0.01$; *, $p \le 0.001$.

Figure 36:
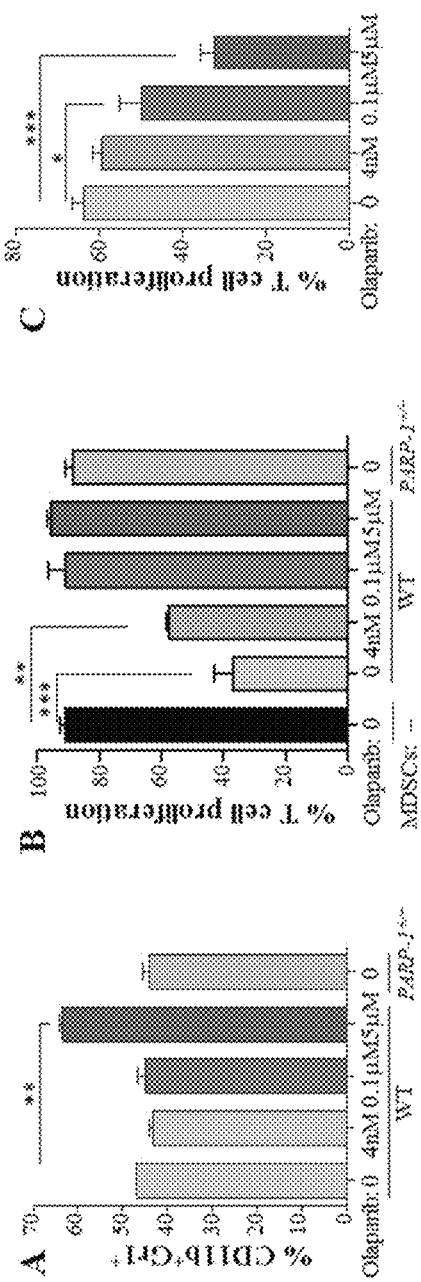

FIG. 36 shows a sub-IC50 concentration of olaparib is sufficient to interfere with MDSC suppressive function by blocking expression of ARG-1, iNOS, and COX2 and adoptive transfer of WT MDSCs abrogates the protective effects of PARP-1 heterozygosity against the tumor burden Bone marrow progenitors derived from WT or PARP-1$^{+/+}$ mice were incubated with a cocktail of GM-CSF, G-CSF, and IL-6 at day 0. After 24 h, WT cells were treated with different concentrations of olaparib or DMSO. After 96 h, cells were collected and stained with antibodies to CD11b or Gr1 and assessed by FACS (A) or co-cultured with CD3/CD28-stimulated and CFSC-labeled WT CD3$^+$ T cells for 72 h followed by an assessment of proliferation by FACS (B). (C) A portion of CD3/CD28-stimulated and CFSE-labeled WT T cells were incubated with different concentrations of olaparib in the absence of MDSCs for 72 h and assessed for proliferation by FACS. (D) An equal number of MCA-38 cells were engrafted onto the left flanks of WT or PARP-1$^{+/-}$ mice. At days 8 and 16, mice received, intratumorally, $3 \times 10^6$ WT BM-MDSCs or vehicle. Tumor sizes were measured at the indicated days. (E) Bone marrow cells were stimulated and treated with 4 nM or 5 µM olaparib as in (A). Cells were collected at days 2, 3 or 4. Total protein extracts were prepared and subjected to immunoblot analysis with antibodies to ARG-1, iNOS, COX-2, PARP-1, p53, phospho (S15)-p53, phospho(S37)-p53, STAT3, phospho(Y705)-STAT3, GAPDH, or Actin. (F) Bone marrow cells were stimulated with the cytokine cocktail in the presence of 4 nM or 1 µM olaparib as in (A). At day 4 of MDSC differentiation (70% Gr1$^+$), wells received 0.5 ml of fresh medium or medium containing MC-38 cells at a ratio of 2:1 (MC-38/MDSC). The cells received a second treatment with olaparib but with no additional cytokines. Some MC-38 cells were incubated without MDSCs and in the presence or absence of olaparib. Cells were collected after 2 days of treatment and protein extracts were subjected to immunoblot analysis with antibodies to ARG-1, iNOS, PARP-1, tubulin or actin. (G) WT or PARP-1$^{+/-}$ MDSCs were treated as in (F) except that 3LL cells were used instead of MC-38 cells. Protein extracts were subjected to immunoblot analysis with antibodies to iNOS or GAPDH. The modulatory effect of low-dose olaparib on MDSC function is independent of PARP-1 trapping to chromatin (H) Bone marrow-derived MDSCs were treated with different concentrations of olaparib for 12 h. Nuclear and chromatin fractions were prepared and subjected to immunoblot analysis with antibodies to PARP-1 or H3. (I) Positive control for PARP-1 trapping. Jurkat T cells were treated with 20 µM VP-16 in the presence or absence of 4 nM or 1 µM olaparib for 1 h. Chromatin fractions were subjected to immunoblot analysis with antibodies to PARP-1, γH2AX, or H3.

Figure 37:
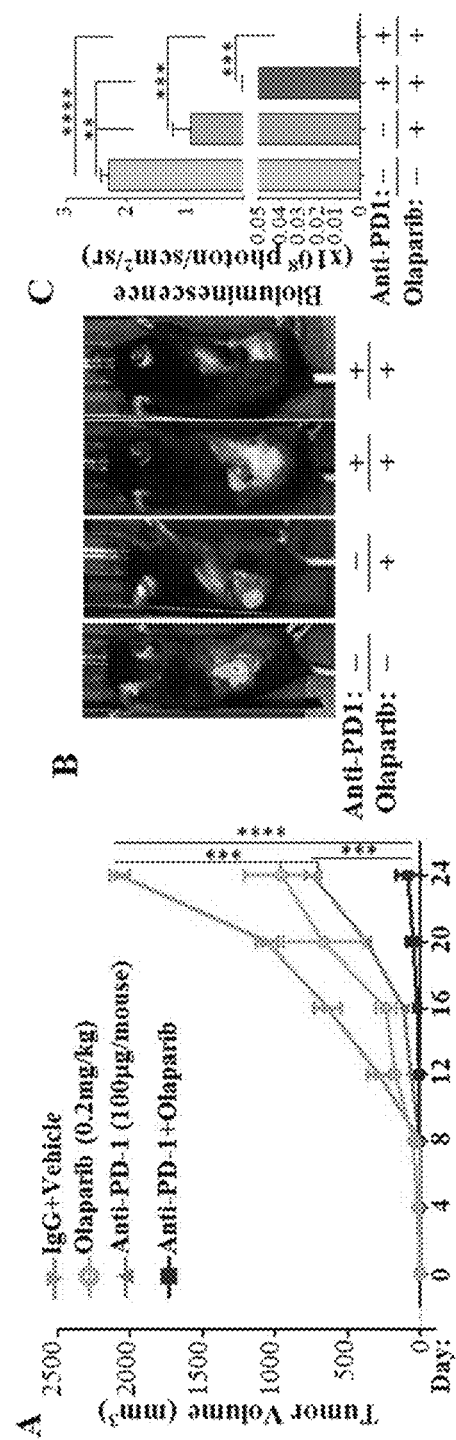

FIG. 37 shows synergy between a metronomic dose of olaparib and anti-PD1 therapy to eradicate MC-38 cell-based tumors in mice. (A) MC-38 cells were engrafted onto flanks of WT mice. When tumors became palpable (day 4-6) mice were treated with 0.2 mg/kg olaparib, 100 µg anti-PD1, or a combination of the two agents; mice treated with only olaparib also received equal amount of IgG isotype (for example, clone 2A3 (cat #: BE0089 from bioxcell). Tumor volumes were then measured every 4 days. (B-C) GFP-Luciferase-expressing MC-38 cells were engrafted onto WT mice as in (A). At day 16, tumors were imaged by the whole body IVIS optical imaging system (B) Representative images of the different experimental groups. (C) Bioluminescence in the region of interest (ROI) was quantified in photons/sec/cm$^2$/sr. (D) MC-38 cells were engrafted onto flanks of WT or PARP-1$^{+/-}$ mice. At day 6, mice were then administered either anti-PD1 or IgG isotype. Tumor volume was assessed at day 24. (E) Spleen weight of mice from the different groups. (F) Sera from the different mouse groups were assessed for TNF-α, IL-6, or MCP-1 by ELISA. (G) Protein extracts from tumors derived from the different experimental groups were subjected to immunoblot analysis with antibodies to PD-L1, cleaved (active) caspase-3, -7, -8, or -9, γH2AX, GAPDH, p21/Waf1/Cip1, poly(ADP-ribose) (PAR), cleaved PARP-1 (p85), or Grb2. Two left braces represent two different gels using the same samples. (H) CT-26 cells were engrafted onto flanks of WT mice and then treated with olaparib with anti-PD1 or IgG isotype as described in (A). Tumor volumes were then measured every 4 days. (I) Spleen weight of mice from the different groups. For (A), (C-F), and (H-I), *, $p \le 0.05$;  $p \le 0.01$; *, $p \le 0.001$.

Figure 38:
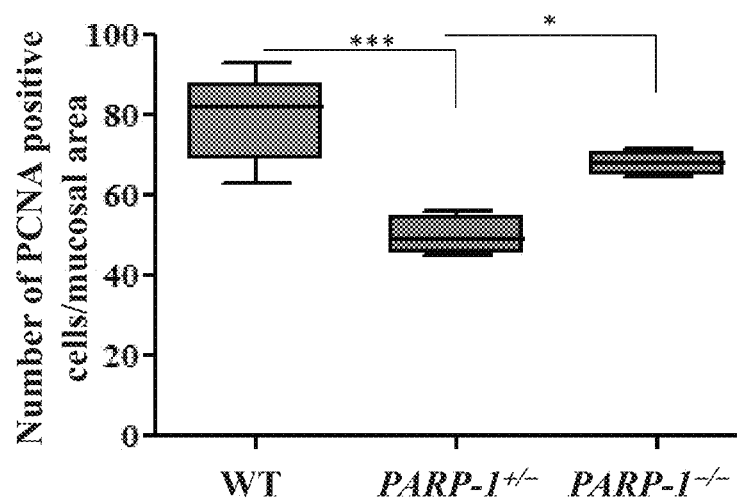

FIG. 38 shows quantification of PCNA positive cells in the colonic mucosa of AOM/DSS-treated mice. Data is expressed as percent of total cells per 10 mm2 area within colonic mucosa. *, p≤0.05; ***, p≤0.001.

Figure 39:
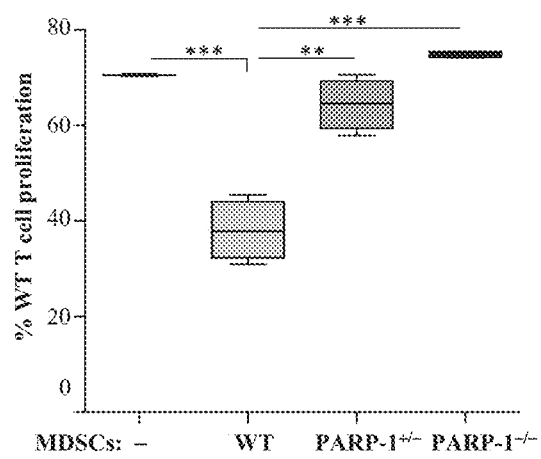

FIG. 39 shows genotyping of $APC^{Min/+}$, $APC^{Min/+}$ PARP-$1^{+/-}$, and $APC^{Min/+}$ PARP-$1^{-/-}$ mice. Experimental groups of APCMin/+ mice are showing in the top panel, while the Bottom panel represents the genotyping of PARP-1 in each experimental group. (B) Tumor numbers along intestinal tract were counted in.

Figure 40:
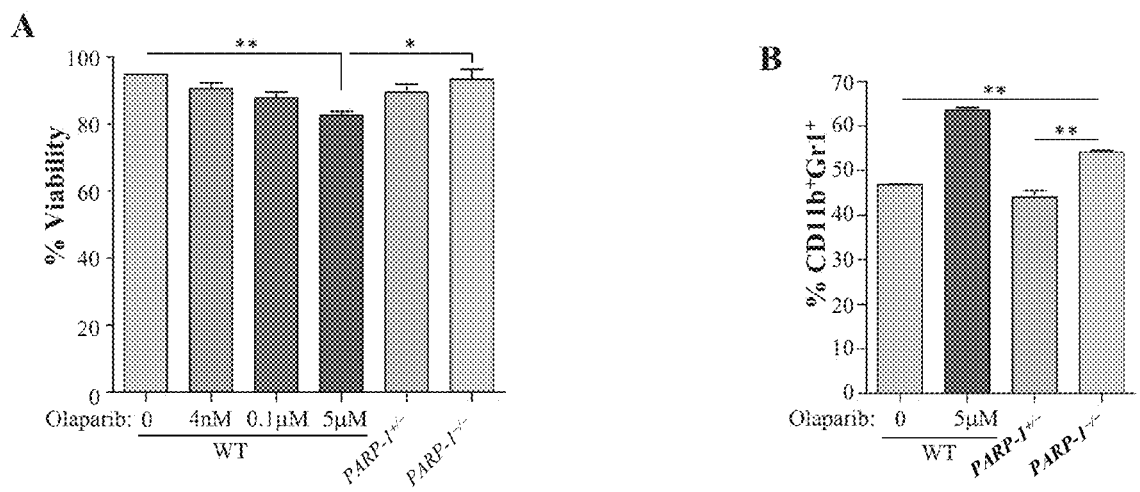

FIG. 40 shows PARP-1 gene knockout blocks the suppressive activity of MDSCs. CD11b-enriched MDSCs isolated from tumors of WT, PARP-1+/- or PARP-1-/- mice were assessed for their ability to suppress proliferation of CD3/CD28-stimulated and CFSC-labeled WT CD3+ T cells at a MDSC/T cell ratio of 1:8. T cell proliferation was assessed by FACS. *, p≤0.05; , p≤0.01; *, p≤0.001.

Figure 41:
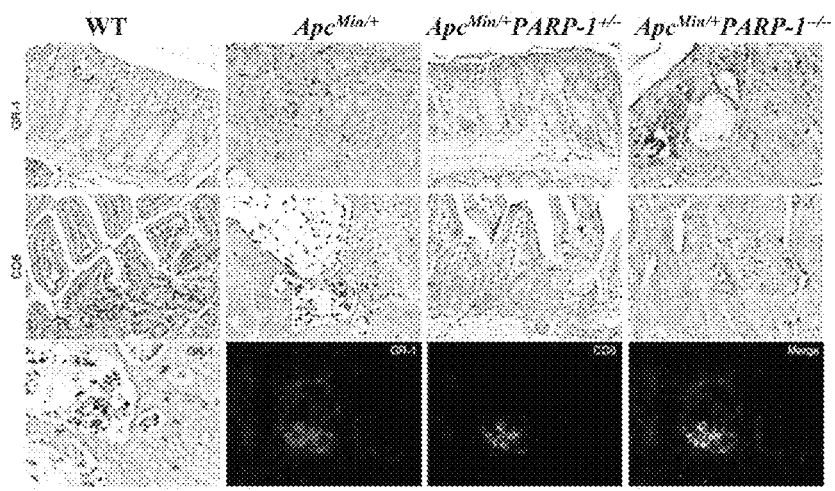

FIG. 41 shows effects of PARP inhibition on viability and differentiation of bone marrow-derived MDSCs in vitro. WT, treated with different concentrations of olaparib, PARP-1+/- or PARP-1-/- mice were stimulated with GM-CSF, G-CSF, and IL-6 as described for FIG. 5A. (A) Viability of differentiated cells was assessed by FACS. Only the 5 µM olaparib caused a slight but statistically significant decrease in percentage of viable cells. (B) PARP inhibition by 5 µM olaparib in WT cells or PARP-1 knockout increased percentage of Gr1+ MDSCs. *, p≤0.05; **, p≤0.01

Figure 42:
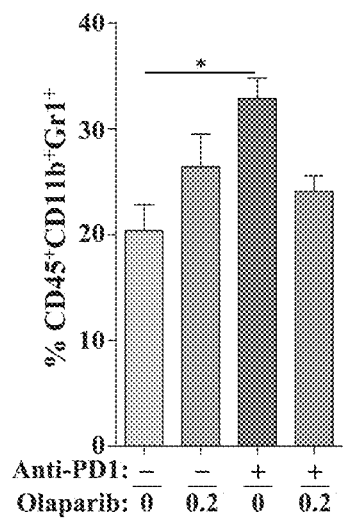

FIG. 42 shows PARP-1 gene knockout increases prevalence of $Gr^+$-MDSCs in $APC^{Min/+}$ mice. Tissue sections from the different experimental groups were subjected to IHC or immunofluorescence with antibodies to mouse Gr1 or CD8. The assessment of Gr1+ cells was conducted, in a blinded manner, by Dr L. DelValle.

Figure 43:
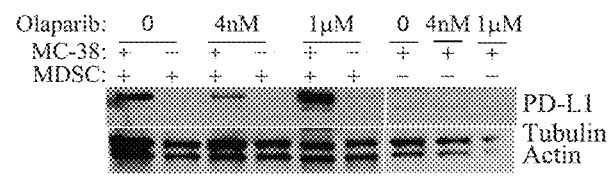

FIG. 43 shows differential effects of low and high concentrations of olaparib on PD-L1 expression in MDSCs co-cultured with MC-38 cells. Bone marrow-derived MDSCs were co-cultured with MC-38 cells and treated with olaparib as described for FIG. 36E. The same blot was assessed for PD-L1 using antibodies to mouse PD-L1. Note that the blot for tubulin and actin is the same as the one displayed in FIG. 36E.

Figure 44:
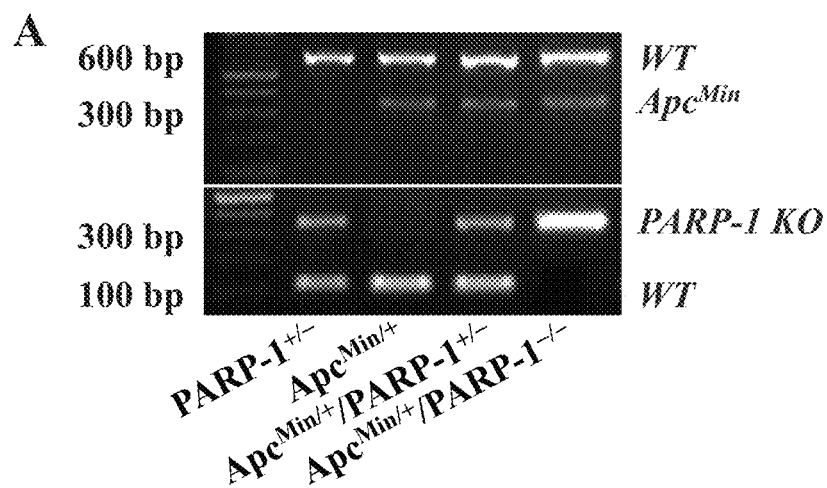

FIG. 44 shows effect of olaparib, anti-PD1, or combination treatment on prevalence of MDSCs in CT-26 cell-based tumors in mice.

Figure 45:
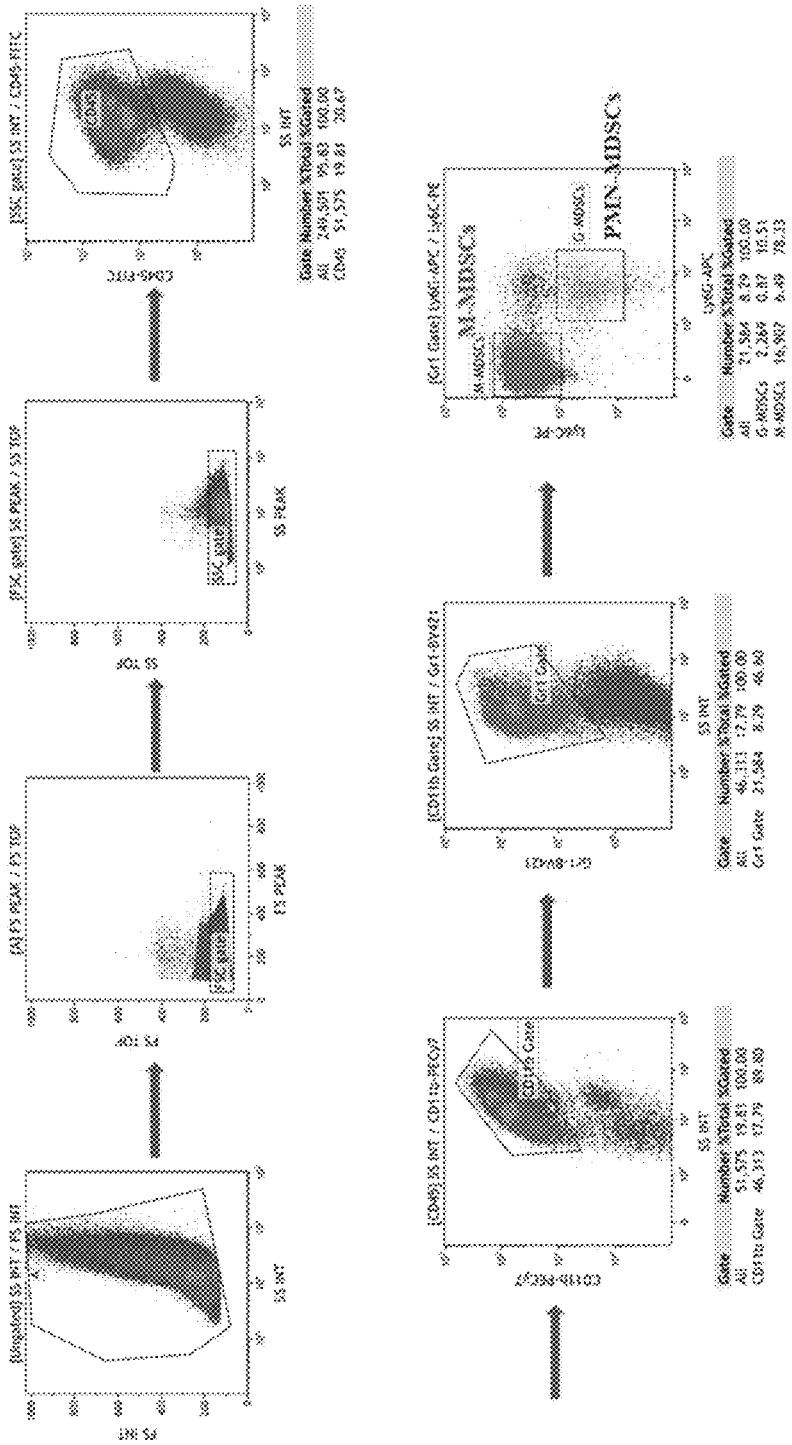

FIG. 45 shows detailed description of the gating strategy used to assess MDSCs in the different experimental groups.

Figure 46:
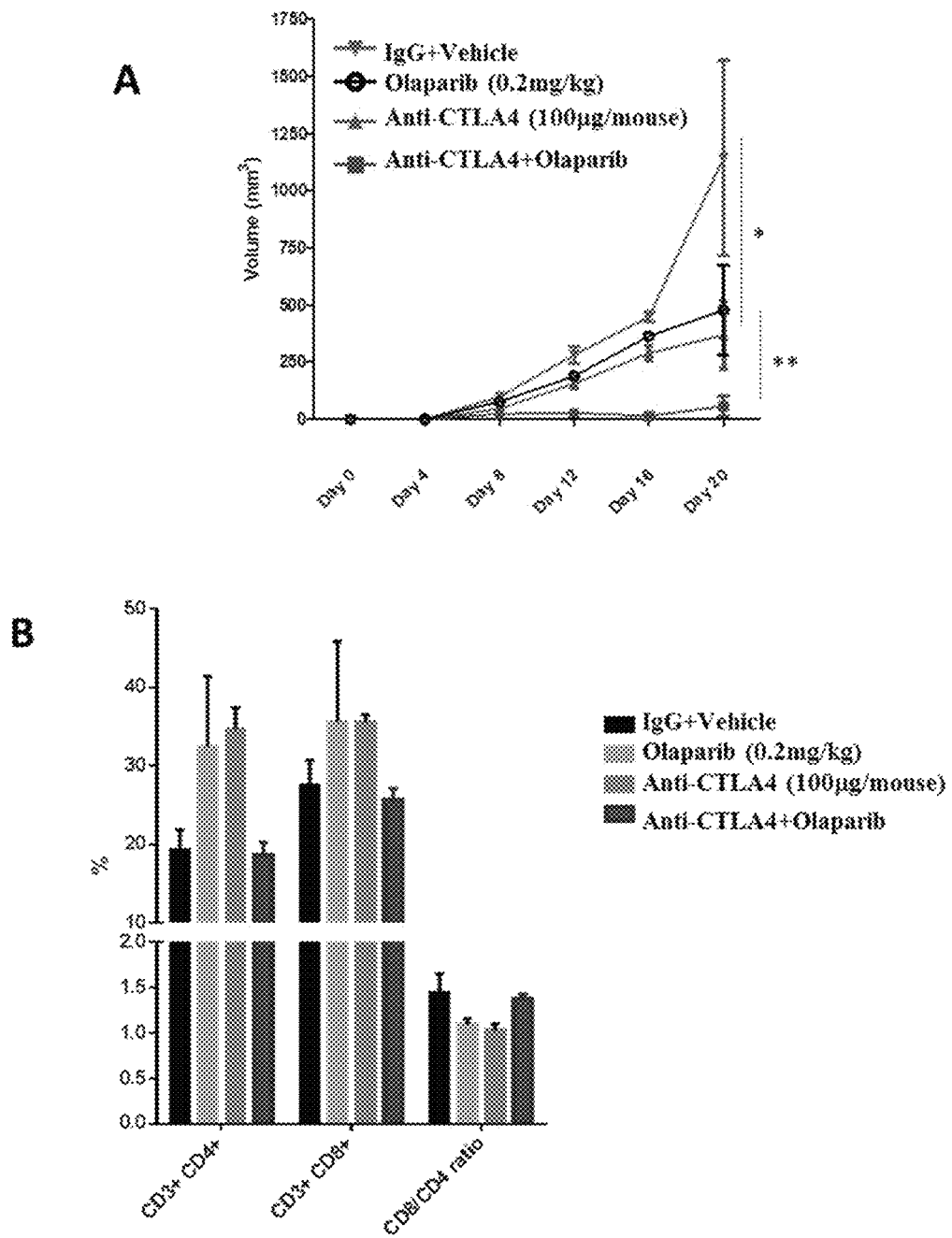

FIG. 46 shows synergy between a metronomic dose of olaparib and anti-CTLA4 therapy to eradicate MC-38 cell-based tumors in mice. (A) MC-38 cells were engrafted onto flanks of WT mice. When tumors became palpable, mice were treated with 0.2 mg/kg olaparib, 100 mg anti-CTLA4, or a combination of the two agents; mice treated with only olaparib also received equal amount of IgG isotype. Tumor volumes were then measured. Tumors from the different experimental groups were processed to generate single-cell suspensions, which were stained with a combination of antibodies to CD45, CD11b, Gr1, Ly6C, Ly6G, CD3, CD4, or CD8. CD11b$^+$ cell population was gated from the live CD45$^+$ population. (B) Percentages of CD45$^+$ CD3$^+$ and CD3$^+$CD8$^+$ cell populations in tumors of the different groups. (C) Percentages of CD11b$^+$Gr1$^+$ and those of CD11b$^+$Ly6C$^+$ and CD11b$^+$Ly6G$^+$ populations in tumors of the different groups. *, p≤0.05; , p≤0.01; *, p≤0.001.

Figure 47:
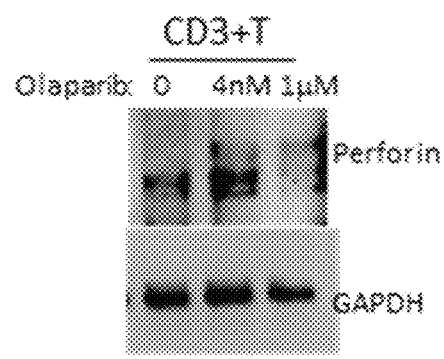

FIG. 47 shows a low of olaparib enhances while a high concentration decreases T cell function in vitro. CD3+ T cells were isolated from spleen then stimulated with antibodies to CD3 and CD28 for 3 days. Protein extracts were analyzed by immunoblotting with antibodies to perforin (a marker of T cell function) or GAPDH. Note that the 4 nM concentration increased, while the 1 mM decreased, perforin levels.

Figure 48:
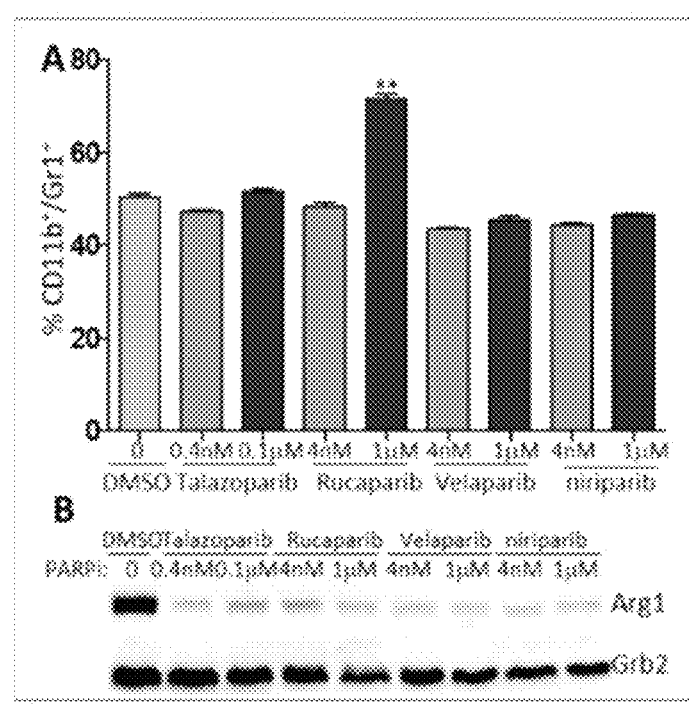

FIG. 48 shows different PARP inhibitors reduce MDSC function (A) Bone marrow-derived MDSCs were incubated at day 2 of differentiation with DMSO or the different PARP inhibitors at the indicated concentrations. At day 4, a portion of the cells was assessed for CD11b and Gr1 by FACS. **, p≤0.01. (B) Proteins from the remaining cells were subjected to immunoblot analysis with antibodies to Arg1 or Grb2 (as a loading control). This figure shows that none of the PARP inhibitors affected MDSC phenotype (CD1 b$^+$/Gr1$^+$) at day 4 of differentiation except rucaparib at 1 µM, which appears to increase MDSC population. Consistently with our results, a low concentration of 4 nM of rucaparib, niraparib, or velaparib or 0.4 nM talazoparib blocked expression of Arg1 in BM-MDSCs in a manner similar to olaparib.

Figure 49:
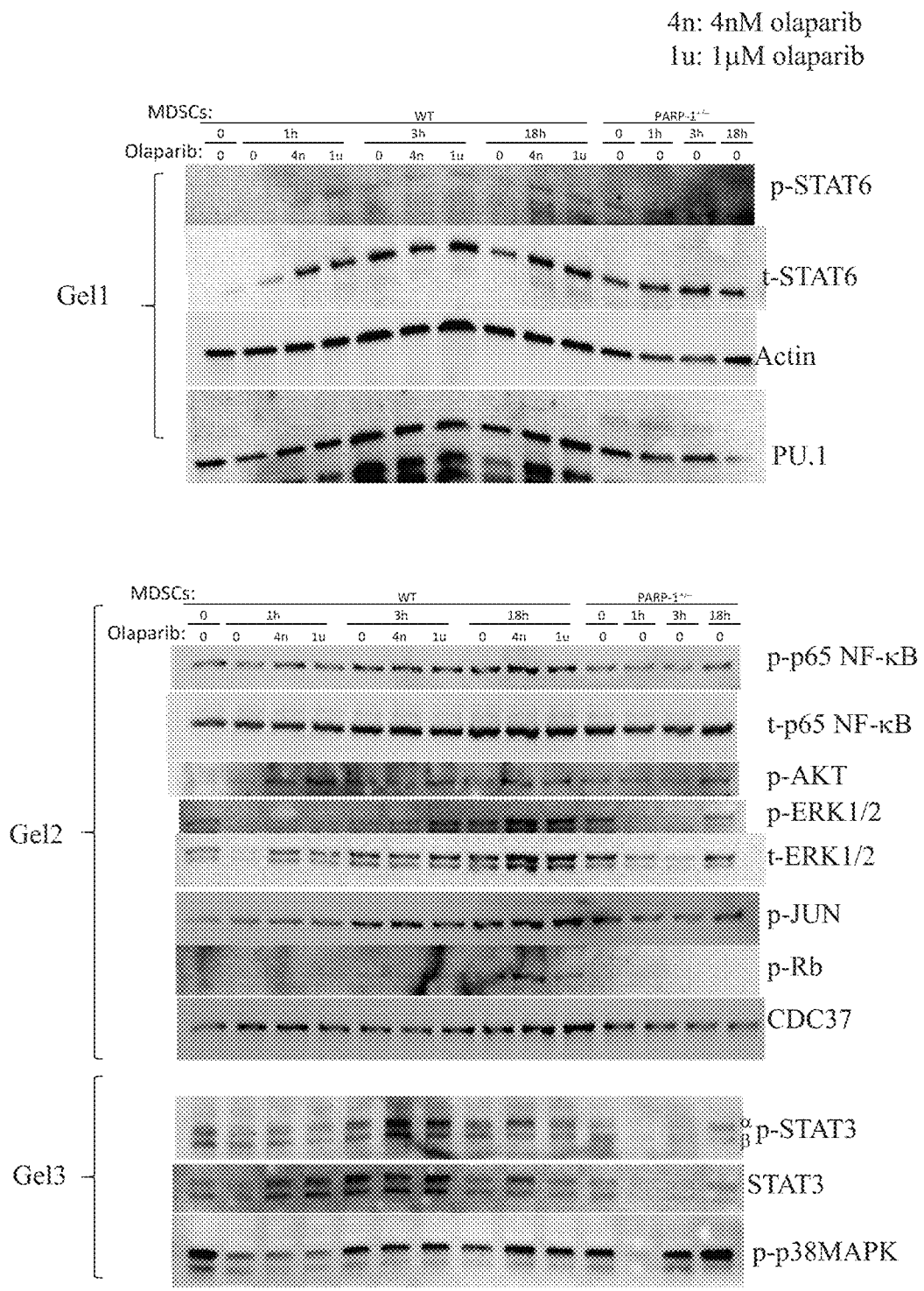

FIG. 49 shows bone marrow cells isolated from Wild type or PARP-1+/-(heterozygous) mice were induced for differentiation into MDSCs with 40 ng/ml GM-CSF, G-CSF, and IL-6. Wild type cells were treated with either 4 nM (4n) or 1 mM (1u) olaparib. Cells were collected at the indicated time intervals. Protein extracts were prepared and subjected to immunoblot analysis with antibodies to the factors mentioned in the side of each gel. Gel 1, 2, and 3 were generated using the same samples.

DETAILED DESCRIPTION OF THE INVENTION

Detailed descriptions of one or more preferred embodiments of compositions and methods for treating tumors comprising administering PARP inhibitor compounds are provided herein.

It is to be understood, however, that the present invention may be embodied in various forms. Therefore, specific details disclosed herein are not to be interpreted as limiting, but rather as a basis for the claims and as a representative basis for teaching one skilled in the art to employ the present invention in any appropriate manner.

The singular forms "a", "an" and "the" include plural reference unless the context clearly dictates otherwise. The use of the word "a" or "an" when used in conjunction with the term "comprising" in the claims and/or the specification may mean "one," but it is also consistent with the meaning of "one or more," "at least one," and "one or more than one."

Wherever any of the phrases "for example," "such as," "including" and the like are used herein, the phrase "and without limitation" is understood to follow unless explicitly stated otherwise. Similarly "an example," "exemplary" and the like are understood to be nonlimiting.

The term "substantially" allows for deviations from the descriptor that do not negatively impact the intended purpose. Descriptive terms are understood to be modified by the term "substantially" even if the word "substantially" is not explicitly recited.

The terms "comprising" and "including" and "having" and "involving" (and similarly "comprises", "includes," "has," and "involves") and the like are used interchangeably and have the same meaning. Specifically, each of the terms is defined consistent with the common United States patent law definition of "comprising" and is therefore interpreted to be an open term meaning "at least the following," and is also interpreted not to exclude additional features, limitations, aspects, etc. Thus, for example, "a process involving steps a, b, and c" means that the process includes at least steps a, b and c. Wherever the terms "a" or "an" are used, "one or more" is understood, unless such interpretation is nonsensical in context.

As used herein, the term "about" can refer to approximately, roughly, around, or in the region of. When the term "about" is used in conjunction with a numerical range, it modifies that range by extending the boundaries above and below the numerical values set forth. The term "about" is used herein to modify a numerical value above and below the stated value by a variance of 20 percent up or down (higher or lower).

"Amelioration" can refer to any lessening of severity, delay in onset, slowing of growth, slowing of metastasis, or shortening of duration of a tumor or cancer, whether permanent or temporary, lasting or transient that can be attributed to or associated with administration of a PARP inhibitor compound or composition.

The terms "individual", "patient" and "subject" can be used interchangeably. They refer to a mammal (e.g., a human) which is the object of treatment, or observation. Typical subjects to which PARP inhibitor compounds can be administered will be mammals, particularly primates, especially humans. For veterinary applications, a wide variety of subjects will be suitable, e.g., livestock such as cattle, sheep, goats, cows, swine, and the like; poultry such as chickens, ducks, geese, turkeys, and the like; and domesticated animals particularly pets such as dogs and cats. For diagnostic or research applications, a wide variety of mammals will be suitable subjects, including rodents (e.g., mice, rats, hamsters), rabbits, primates, and swine such as inbred pigs and the like.

Partial Inhibition of Poly(ADP-Ribose) Polymerase) for the Treatment of Disease

Poly(ADP-ribose)polymerases (PARPs) is a family of proteins that play a role not only in DNA repair, but also in fundamental cellular processes such as chromatin remodeling, transcription, and regulation of the cell cycle. PARPs interact with various cellular proteins and transcription factors, including those that aid inflammation. Various studies have shown that DNA damage occurs during inflammatory conditions, and that PARPS (for example, PARP-1) participate in inflammation through the response to DNA damage. In fact, DNA damage that occurs during inflammation leads to an over activation of PARPs (Deslee G, et al. *Chest* (2009) 135:965-74; Althaus F R, et al. *Mol Cell Biochem* (1999) 193:5-11; Pereira C, et al. *Inflamm Bowel Dis* (2015) 21:2403-17; Palmai-Pallag T, et al. *Microbes Infect* (2014) 16:822-32) which can result in an energy crisis due to depletion of their substrate, i.e., nicotinamide adenine dinucleotide (NAD+), thus leading to non-specific cell death (i.e., necrosis) (Ha H C, Snyder S H. *Proc Natl Acad Sci USA* (1999) 96:13978-82.).

Mammalian PARP-1 is a 116-kDa protein which comprises of an N-terminal DNA-binding domain, a nuclear localization sequence (NLS), a central automodification domain, and a C-terminal catalytic domain (Luo X, et al. *Genes Dev* (2012) 26:417-32). The C-terminal region is the most conserved part of the PARP family of proteins, and executes its catalytic function. Specifically, the C-terminal region synthesizes poly(ADP)ribose (PAR) using NAD+ as a substrate (35, 36) and transfers the PAR moieties to several proteins, including histones, DNA repair proteins, and transcription factors (Ame J C, et al. *Bioessays* (2004) 26:882-93; Schreiber V, et al. *Nat Rev Mol Cell Biol* (2006) 7:517-28), ultimately altering the structure and functions of the acceptor proteins. Target proteins comprise, for example, a PARP protein itself (for example automodification of PARP-1's BRCT (Breast Cancer Carboxy-Terminal) domain), or modification of other proteins (i.e., heteromodification) such as Histone H1, H2B, DNA pol a, topoisomerase I, II, lamin B, XRCC1, SV40 T-Ag, DNAS1L3; DFF40; p65 NF-kB, and/or STAT6. Under genotoxic stress conditions, PARP-1 binds itself to the nucleosomes containing intact (Kim M Y, et al. *Cell* (2004) 119:803-14) as well as damaged DNA structures (e.g., nicks and double-strand breaks) which leads to the activation of DNA repair enzymes (D'Amours D, et al. *Biochem J* (1999) 342(Pt 2): 249-68).

The covalently attached PAR can be hydrolyzed to free PAR or mono(ADP-ribose) by PAR glycohydrolase (PARG) (Min W, et al. *Front Biosci (Landmark Ed)* (2009) 14:1619-26). Synthesis and degradation of PAR chains is tightly controlled in vivo and PAR residues have a very short half-life in the cell (few minutes) (Luo X, et al. *Genes Dev* (2012) 26:417-32). Free or protein-bound PAR polymers also work as signal transducers by binding other proteins.

PARP-1 gets activated in response to DNA damage induced by ROS/RNS under inflammatory conditions (Ba X, et al. *Am J Pathol* (2011) 178:946-55, Pacher P, et al. *Am J Pathol* (2008) 173:2-13.). Although, the primary aim of PARP-1 is to maintain the genome integrity, its over activation under extensive and persistent DNA damaging environment promote inflammatory conditions. Over activation of PARP-1 depletes its substrate, i.e., NAD+, bringing the cell to an energy deficient state, thus leading to necrosis (Islam B U, et al. *Indian J Clin Biochem* (2015) 30:368-85). Recently, PARP-1 has been reported to cause cell death by suppressing the activity of hexokinase-1 (an essential enzyme of glycolysis) by adding PAR chains (Fouquerel E, et al. *Cell Rep* (2014) 8:1819-31). Apart from inducing cellular death, PARP-1 promotes inflammation by influencing chromatin remodeling and expression of several pro-inflammatory factors. Since the DNA is negatively charged, poly(ADP)ribosylation (also negatively charged) of histones results in relaxing of nucleosomal structures and, hence, aids the transcription of pro-inflammatory genes (Martinez-Zamudio R, et al. *Mol Cell Biol* (2012) 32:2490-502, Martinez-Zamudio R I, et al. *Brain Behav* (2014) 4:552-65). PARP-1 regulates the expression of several NF-κB-dependent cytokines, chemokines, adhesion molecules, inducible nitric-oxide synthase (iNOS), required for the manifestation of inflammatory cycle (Naura A S, et al. *Eur Respir J* (2009) 33:252-62; Chiang J, et al. *Eur J Pharmacol* (2009) 610: 119-27; von Lukowicz T, et al. *Cardiovasc Res* (2008) 78:158-66; Park E M, et al. *Stroke* (2004) 35:2896-901; Zingarelli B, et al. *Circ Res* (1998) 83:85-94; Sharp C, et al. *Inflammation* (2001) 25:157-63; Ullrich O, et al. *Nat Cell Biol* (2001) 3:1035-42). PARP-1 gene deletion or its pharmacological inhibition results in suppressed migration of leukocytes to the inflammatory sites (Rosado M M, et al. *Immunology* (2013) 139:428-37). Overall, studies demonstrate that PARP-1 plays a pro-inflammatory role by inducing cellular death and upregulating the expression of various inflammatory genes, via interaction with NF-κB (Zerfaoui M, et al. *J Immunol* (2010) 185:1894-902; Hassa P O, *Cell Mol Life Sci* (2002) 59:1534-53). Further, see Sethi G S et al. *Front. Immunol.* (2017) 8:1172).

Poly(ADP-ribose) polymerase (PARP-1) is a nuclear enzyme that polymerize adenosine diphosphate ribose on substrate proteins to regulate various processes. See FIG. 11, for example. The function of PARP-1 in cancers may be intimately related to its role in providing alternative and efficient pathways to cancer cells to survive especially for those associated with defects in DNA repair (e.g. triple negative breast and ovarian cancers). The role of PARP-1 in DNA repair requires full activity of the enzyme as partial inhibition of PARP-1 has not been associated with obvious defects in DNA repair. Achieving maximum inhibition of PARP-1 to treat cancers with DNA repair deficiency (e.g. breast or ovarian cancers with mutations in BRCA1 gene) is critical to induce synthetic lethality of cancer cells. As discussed herein, the focus on achieving maximal or about maximal inhibition of PARP may contribute to the failure of two recent clinical trials using the PARP-1-inhibitor, olaparib (Lynparza™), on patients with advanced colon cancer as a monotherapy or in combination with irinotecan (Camptosar™), a topoisomerase I inhibitor. Achieving maximum inhibition of PARP to treat cancers with DNA repair deficiency (e.g. breast or ovarian cancers with mutations in BRCA1 gene) is critical to induce synthetic lethality of such cancer cells. However, partial inhibition may be the best approach to blocking inflammation-driven cancer or certain mutation driven cancers, such as APC mutation-driven (e.g. FAP) colon cancer.

Without wishing to be bound by theory, DNA repair enzymes such as PARP-1 play important roles in not only cancer-related processes but also in the pathogenesis of many inflammatory diseases. However, it's role in inflammation may be very different than that in cancer. PARP-1 has a critical role during inflammation, in part, through its relationship with NF-kB, and embodiments as described herein demonstrate the roles of PARP-1 in colon inflammation and cancer and their relationship. Examples described herein demonstrate the clinically relevant role of partial inhibition of a PARP enzyme, such as PARP-1, by using chemical inhibitors of PARP, while also taking advantage of the fact that PARP-1 gene heterozygosity reduces expression and activity of PARP-1 by about 50%. As an example of a clinically relevant PARP inhibitor, examples described herein utilize olaparib (AZD2281)), a potent inhibitor of PARP-1, PARP-2, and PARP-3 that is used in the clinic as a monotherapy for triple-negative ovarian cancer. Triple negative ovarian cancer is defined based on negative oestrogen receptor (ER), progesterone receptor (PR) and human epidermal growth factor receptor-type 2 (HER2) expression. Experiments described herein also use the extensively studied APC$^{min/+}$ mouse model of intestinal cancer, which is a standard model for spontaneous tumorigenesis. In this model, aberrant Wnt/β-catenin signaling following loss of the tumor suppressor gene, adenomatous polyposis coli (APC), is thought to initiate colon adenoma formation. Still further, experiments described herein also use the carcinogen/inflammation colon cancer model (azoxymethane+DSS–driven). In this model, DSS regimen is given to induce chronic relapsing inflammation after the potentiation by the carcinogen, azoxymethane (AOM), in colon. Finally, a MCA-38 colon carcinoma cell-based allograft model was used in examples described herein, which allows for the investigation of the host environment response to tumor growth.

Referring to the Examples, partial PARP-1 inhibition (50%) was very effective at reducing or even blocking expression of inflammatory genes in response to LPS or TNF-α treatment and that complete inhibition of the enzyme was not necessary to achieve maximal effects. See FIG. 14, for example. This appears to be due, in part, to a reduction in NF-κB-signal transduction. The remarkable anti-inflammatory effects of PARP-1 inhibition (partial or total) can be protective against chronic inflammation-driven colon carcinogenesis. Surprisingly, partial PARP-1 inhibition by gene heterozygosity was more efficient than complete inhibition by gene knockout at reducing chronic inflammation-driven colon tumorigenesis using an azoxymethane (AOM) followed by dextran sulfate sodium (DSS) exposure-based model of the condition although both genotypes provided similar reduction in the levels of systemic and colonic inflammation. See FIG. 15, for example. When a mutation in the (β-catenin pathway (Apc$^{MIN}$) was the main driver for intestinal tumorigenesis, partial PARP-1 inhibition by gene heterozygosity or olaparib protected against the tumor burden in Apc$^{Min/+}$ mice while complete inhibition by gene knockout aggravated the burden. See FIG. 5 and FIG. 22, for example. These differential effects were not mirrored with respective effects on systemic or intestinal inflammation, splenomegaly, or cachexia as all conditions lowered the aforementioned traits. Using a MCA-38 colon carcinoma cell-allograft mouse model, the opposing effects of PARP-1 gene dosages on intestinal tumorigenesis occurred despite that they both provide a tumor suppressive microenvironment through a regulation of the function of Myeloid-Derived Suppressor Cells (MDSCs). These results exemplify the complexity of the role of PARPs in colon tumorigenesis, inflammation, and immunity that could be harnessed to effectively treat not only colon cancer but also other cancers that exist within a tumor microenvironment, such as breast, liver and prostate.

The results of the inventors' studies exemplify the complexity and the potentially paradoxical roles of PARPs in cancer by using colon carcinogenesis as a model. Achieving maximum inhibition of PARP to treat cancers with DNA repair deficiency (e.g. breast or ovarian cancers with mutations in BRCA1 gene) is critical to induce synthetic lethality of cancer cells. However, partial inhibition may be the best approach to blocking inflammation-driven or APC mutation-driven (e.g. FAP) colon cancer. The focus on achieving maximal inhibition of PARP may be the reason for the failure of two recent clinical trials using olaparib (Lynparza™) on patients with advanced colon cancer as a monotherapy or in combination with irinotecan (Camptosar™), a topoisomerase I inhibitor. In some instances, the patient may be developing resistance to the drug, in part due to the high doses administered (such as 600 mg/day).

In cancer, the normal intercellular interactions in tissues are disrupted, and the tumor microenvironment evolves to accommodate the growing tumor. The tumor microenvironment (TME) refers to the cellular environment in which a tumor exists, including components such as surrounding blood vessels, immune cells, fibroblasts, bone marrow-derived inflammatory cells, lymphocytes, signaling molecules and the extracellular matrix (ECM). Referring to FIG. 6 which utilizes a MA-38 cell-based allograft (immunocompetent) model of colon cancer, PARP inhibition provides a tumor-suppressive microenvironment. Specifically, this example demonstrates the effect of inhibiting PARP only in the immune cells of the subject (and not in the cancer cells), However, of clinical relevance, when PARP is inhibited in both immune cells and in cancer cells (as is the case when a PARP inhibitor is administered to a subject), low doses of PARP inhibitors selectively affect the tumor microenvironment (such as MDSCs) but not cancer cells. See FIG. 5, for example.

Tumor microenvironment is complex and is heavily influenced by immune system. Emerging immune cells that influence and/or drive tumorigenesis are known as Myeloid-derived suppressor cells (MDSCs). MDSCs are a heterogeneous population of cells that are defined by their myeloid origin, immature state and ability to potently suppress T cell responses. MDSCs migrate from the basement membrane (BM) and recruit to the site of tumor by tumor-associated macrophages (TAM). MDSCs are potent immune suppressors (i.e., immunosuppressive), which as a result contributes to tumor progression. Specifically, MDSCs can infiltrate a developing tumor and promote vascularization, inhibit major pathways of immunosurveillance, inhibit natural killer (NK) cell-dependent cytotoxicity, inhibit T and B cell proliferation, inhibit antigen presentation by dendritic cells (DC), and drive M1 macrophage polarization.

MDSCs are increasingly being viewed as important players in promoting progression or even resistance of most cancers. Referring to the Examples, PARP-1 plays a role in the function of MDSCs. Again, partial inhibition of PARP-1 is sufficient to interfere with the suppressive capacity of these cells (see FIG. 7 and FIG. 17, for example). The role of PARP-1 in the function of MDSCs may be harnessed as an added therapy to block many forms of cancers including colon cancer.

Importantly, PARP-1 inhibition interferes with the suppressive capacity of MDSCs, while having little to no effect on T cell or dendritic cell function (see FIG. 18, for example).

Therapeutic Methods

Described herein are methods of treating a subject afflicted with a tumor and/or cancer comprising administering to a subject a low dose of a PARP inhibitor compound. The term "low dose" refers to a very small quantity of the PARP inhibitor compound relative to the well-established/conventional larger quantities (such as 600 mg/day) that are known to produce an effect in certain cancers with DNA repair deficiency (e.g. breast or ovarian cancers with mutations in BRCA1 gene). As described herein, a low dose of a PARP inhibitor compound produces a different effect than the well-established higher dose. Referring to FIG. 20, for example, low dose of a PARP inhibitor compound is much more effective than the high dose in blocking colon cancer when administered to a subject after the clear development of tumors.

A low dose of a PARP inhibitor compound is a quantity that is effective for partial inhibition of PARP-1 enzymatic activity. In another embodiment, a low dose of a PARP inhibitor compound is a dose that is below that which represents the threshold for maximal and/or complete inhibition of enzymatic activity. "Partial inhibition" can refer to any measurable reduction in the enzymatic activity of a PARP that is less than maximal (i.e., complete) inhibition. For example, partial inhibition of a PARP can refer to reducing the enzymes activity to about 50%, enzymatic activity, about 40% enzymatic activity, about 30% enzymatic activity, about 10% enzymatic activity, or about 1% enzymatic activity. Referring to FIG. 5, for example, partial inhibition of PARP-1 enzymatic activity (such as by about 50%) protects against, while complete inhibition of PARP-1 activity aggravates, tumor burden. Referring to FIG. 15, for example, partial inhibition of PARP-1 activity (such as by about 50%) is more effective at reducing inflammation-driven colon tumorigenesis than complete inhibition of PARP-1 activity. Mechanistically, partial inhibition of PARP-1 activity is sufficient to block expression of inflammatory genes in primary colon epithelial cells (see FIG. 14, for example), indicating that it is not necessary to inhibit all enzymatic activity (as is the goal of large doses of PARP inhibitors) to reduce inflammation.

A low dose of a PARP inhibitor compound can refer to a dose that is about 10× to 150× lower than what is currently prescribed (e.g. see description herein). For example the low dose of a PARP inhibitor compound comprises a dose that is about 10×, 20×, 30×, 40×, 50×, 60×, 70×, 80×, 90×, 100×, 110×, 120×, 130×, 140×, or 150× lower than what is currently prescribed.

For example, certain studies currently administer to a subject 5 mg/kg per day of a PARP inhibitor compound to achieve an effect, wherein an embodiment of the invention can comprise a low dose of about 0.2 mg/kg per day of a PARP inhibitor compound. Thus, a 60 kg individual may be administered approximately 300 mg per day of a PARP inhibitor to achieve an effect, whereas embodiments of the invention may comprise administering to a subject about 12 mg per day of a PARP inhibitor compound. In other embodiments of the invention, a subject can be administered a PARP inhibitor at a dose of between about 1 mg per day to about 30 mg per day. For example, embodiments of the invention comprise a dose of about 1 mg per day, about 5 mg per day, about 10 mg per day, about 15 mg per day, about 20 mg per day, about 25 mg per day, about 30 mg per day, about 35 mg per day, about 40 mg per day or about 50 mg per day. Other embodiments comprise a dose of less than about 100 mg of olaparib. For example, less than about 75 mg of olaparib. For example, about 50 mg of olaparib. The terms "treat," "treating" or "treatment" can refer to the lessening of severity of a tumor or cancer, delay in onset of a tumor or cancer, slowing the growth of a tumor or cancer, slowing metastasis of cells of a tumor or cancer, shortening of duration of a tumor or cancer, arresting the development of a tumor or cancer, causing regression of a tumor or cancer, relieving a condition caused by a tumor or cancer, or stopping symptoms which result from a tumor or cancer. The terms "treat," "treating" or "treatment", can include, but are not limited to, prophylactic and/or therapeutic treatments. Referring to FIG. 5, for example, partial inhibition of PARP-1 activity protects against tumor burden in vivo (e.g., reduces tumor number/mouse and tumor size), while complete inhibition of PARP-1 activity aggravates tumor burden in vivo.

As used herein, the terms "tumor" and "cancer" can be used interchangeably, and generally refer to a physiological condition characterized by the abnormal and/or unregulated growth, proliferation or multiplication of cells.

In embodiments, a "tumor" or "solid tumor" can refer to a solid mass of tissue that is of sufficient size such that an immune response can be detected in the tissue. A tumor may be benign, premalignant, or malignant. A tumor may be a primary tumor, or a metastatic lesion. Examples of cancers that are associated with tumor formation include brain cancer, head & neck cancer, esophageal cancer, tracheal cancer, lung cancer, liver cancer stomach cancer, colon cancer, pancreatic cancer, breast cancer, ovarian cancer, cervical cancer, uterine cancer, bladder cancer, prostate cancer, testicular cancer, skin cancer, rectal cancer, melanoma, kidney cancer, and lymphomas. One of ordinary skill in the art would be familiar with the many disease entities that can be associated with tumor formation.

A "liquid tumor" can refer to neoplasia that is diffuse in nature as they do not typically form a solid mass. Examples include neoplasia of the reticuloendothelial or haematopoetic system, such as lymphomas, myelomas and leukemias. Non-limiting examples of leukemias include acute and chronic lymphoblastic, myeolblastic and multiple myeloma. Typically, such diseases arise from poorly differentiated acute leukemias, e.g., erythroblastic leukemia and acute megakaryoblastic leukemia. Specific myeloid disorders include, but are not limited to, acute promyeloid leukemia (APML), acute myelogenous leukemia (AML) and chronic myelogenous leukemia (CML). Lymphoid malignancies include, but are not limited to, acute lymphoblastic leukemia (ALL), which includes B-lineage ALL and T-lineage ALL, chronic lymphocytic leukemia (CLL), prolymphocytic leukemia (PLL), hairy cell leukemia (HLL) and Waldenstrom's macroglobulinemia (WM). Specific malignant lymphomas include, non-Hodgkin lymphoma and variants, peripheral T cell lymphomas, adult T cell leukemia/lymphoma (ATL), cutaneous T-cell lymphoma (CTCL), large granular lymphocytic leukemia (LGF), Hodgkin's disease and Reed-Sternberg disease.

In embodiments, the formation and/or growth of the tumor is exacerbated by chronic inflammation, the amount of which is dependent upon tumor type. Over time, chronic inflammation can cause DNA damage and lead to cancer. For example, people with chronic inflammatory bowel diseases, such as ulcerative colitis and Crohn disease, have an increased risk of colon cancer.

The approach as described herein (i.e., administration of a low dose of a PARP inhibitor and/or a therapeutically effective amount of a PARP inhibitor, optionally in combination with at least one additional anti-cancer immunotherapy, will provide clinical benefit, defined broadly as any of the following: inhibiting an increase in cell volume, slowing or inhibiting worsening or progression of cancer cell proliferation, inducing tumor regression, reducing primary tumor size, reducing occurrence or size of metastasis, reducing or stopping tumor growth, inhibiting tumor cell division, killing a tumor cell, inducing apoptosis in a tumor cell, reducing or eliminating tumor recurrence. Referring to FIG. 5 and FIG. 21, for example, partial inhibition of PARP-1 activity protects against (e.g., reduces tumor number/mouse and tumor size) tumor burden in vivo, while complete inhibition of PARP-1 activity aggravates tumor burden in vivo. Notably, all large tumors are absent in the subjects with partial inhibition of PARP-1.

In embodiments, the low dose of a PARP inhibitor will synergize with the at least one additional anti-cancer immunotherapy to provide clinical benefit. "Synergy" or "synergize" refers to an effect of a combination that is greater than additive of the effects of each component alone. For example, referring to FIG. 37, a metronomic dose of olaparib synergizes with anti-PD1 therapy to eradicate MC-38 cell-based tumors in mice. As another example, referring to FIG. 46, a metronomic dose of olaparib synergizes with anti-CTLA4 therapy to eradicate MC-38 cell-based tumors in mice.

"Tumor regression" can refer to a decrease in the overall size, diameter, cross section, mass or viability of a tumor; tumor marker reduction or a positive indication from other conventional indicia of cancer diagnosis and prognosis that indicates a reduction or growth slowing of cancer cells, as a result of the treatment of a cancer patient with compositions according to the present invention. For example, the administration of such compounds results in at least about a 30 percent to 50 percent tumor regression, at least about a 60 to 75 percent tumor regression, at least about an 80 to 90 percent tumor regression and at least about a 95 or a 99 percent tumor regression at one or more tumor sites in a cancer patient. Ideally, such administration results in the killing or eradication of viable tumor cells or completely eradicates the tumor cells at one or more tumor sites in a cancer patient, leading to a clinically observable remission or other enhancement in health of a patient.

The term "inhibition of tumor progression" can refer to the ability of a substance or compound to reduce or block the proliferation of, or to decrease growth and development of tumor cells. Further, inhibition of tumor progression can also refer to the ability of a compound or composition to decrease the likelihood that a cancer will progress to a more aggressive cancer, and/or will metastasize.

The term "cellular proliferation" can refer to a phenomenon by which the cell number, such as a tumor cell number, has changed as a result of cell division. This term can also encompass cell growth by which the cell morphology has changed (e.g., increased in size) consistent with a proliferative signal.

Also described herein are compositions and methods for modulating the tumor microenvironment. The term "modulate" can refer to the ability of a compound to change the tumor microenvironment in some measurable way as compared to an appropriate control. For example the PARP inhibitor compound reduces the activity of myeloid derived suppressor cells (MDSCs). In embodiments, the PARP inhibitor compound reduces the tumor suppressive activity of MDSCs. Modulation of the tumor microenvironment can be measured by, for example, assessment of immune cells within a biopsy (such as by FACS using markers specific to MDSC, CD8, NK, DC).

Aspects of the invention are also drawn towards compositions and methods for enhancing T cell function. Referring to FIG. 47, for example, low of olaparib enhances while a high concentration decreases T cell function in vitro.

Aspects of the invention can also be drawn towards compositions and methods of sensitizing resistant tumors to cytotoxic T cells. Without wishing to be bound by theory, resistance to T cells is multifactorial but the compositions and methods described herein can reverse the resistance (i.e., sensitize the cancer cells) to cytotoxic T cells. For example, embodiments can enhance the killing function of cytotoxic T cells and thus reverse the resistance.

Administration

Described herein are methods of treating a subject afflicted with a tumor and/or cancer comprising administering to a subject a low dose of a PARP inhibitor compound. The term "administration" can refer to introducing a PARP inhibitor compound or composition comprising the same into a subject. In general, any route of administration can be utilized. Non-limiting examples of routes of administration comprise parenteral (e.g., intravenous), intraperitoneal, oral, topical, subcutaneous, peritoneal, intraarterial, inhalation, vaginal, rectal, nasal, introduction into the cerebrospinal fluid, or instillation into body compartments. In some embodiments, administration is intraperitoneal. Additionally or alternatively, in some embodiments, administration is parenteral. In some embodiments, administration is intravenous. In other embodiments, administration is orally.

In embodiments, the PARP inhibitor compound can be administered to a subject before, during or after the development of a tumor or cancer. See, for example, FIGS. 19 and 20. In some embodiments, the PARP inhibitor compound is used as a prophylactic and is administered continuously to subjects with a propensity to develop a tumor. In some embodiments, the PARP inhibitor compound is administered to a subject during or as soon as possible after the development of a tumor. In some embodiments, the administration of the PARP inhibitor compound is initiated within the first 48 hours of the onset of the symptoms, within the first 6 hours of the onset of the symptoms, or within 3 hours of the onset of the symptoms. In some embodiments, the initial administration of the PARP inhibitor compound is via any route practical, such as, for example, an intravenous injection, a bolus injection, infusion over 5 minutes to about 5 hours, a pill, a capsule, transdermal patch, buccal delivery, intraperitoneally and the like, or combination thereof. The PARP inhibitor compound should be administered as soon as is practicable after the onset of a cancer is detected or suspected, and for a length of time necessary for the treatment of the cancer, such as, for example, from about 1 month to about 3 months. The length of treatment can vary for each subject, and the length can be determined using the known criteria. In some embodiments, the PARP inhibitor compound is administered for at least 2 weeks, between about 1 month to about 5 years, or from about 1 month to about 3 years.

The terms "co-administration" or the like, as used herein, can refer to the administration of a PARP inhibitor compound and at least one additional compound, such as a second PARP inhibitor compound or an anti-cancer agent, such as anti-PD1, to a single subject, and is intended to include treatment regimens in which the compounds and/or agents are administered by the same or different route of administration, in the same or a different dosage form, and at the same or different time.

An "anti-neoplastic agent", "anti-tumor agent", or "anti-cancer agent" can refer generally to any agent used in the treatment of cancer. Such agents can be used alone or in combination with other compounds and can alleviate, reduce, ameliorate, prevent, or place or maintain in a state of remission of clinical symptoms or diagnostic markers associated with neoplasm, tumor or cancer.

An "anti-inflammatory" agent can refer generally to any agent that is used to reduce inflammation.

In embodiments, the anti-cancer agent can be an anti-cancer immunotherapy. The skilled artisan will recognize that any anti-cancer immunotherapy may be useful in embodiments as described herein. One class of anti-cancer immunotherapies that can be used in embodiments of the invention include checkpoint blockade immunotherapies, such as anti-PD1 antibodies, anti-CTLA4 antibodies, or anti-PDL1 antibodies. Such antibodies can also be referred to as checkpoint blockade inhibitors. The term "immune checkpoint" refers to a molecule such as a protein in the immune system which provides inhibitory signals to its components in order to balance immune reactions. Known immune checkpoint proteins comprise CTLA-4, PD-1 and its ligands PD-L1 and PD-L2 and in addition LAG-3, BTLA, B7H3, B7H4, TIM3, KIR. The pathways involving LAGS, BTLA, B7H3, B7H4, TIM3, and KIR are recognized in the art to constitute immune checkpoint pathways similar to the CTLA-4 and PD-1 dependent pathways (see e.g. Pardoll, 2012. Nature Rev Cancer 12:252-264; Mellman et al., 2011. Nature 480:480-489).

In other embodiments, the anti-cancer agent can be an inhibitor of indoleamine 2,3-dioxygenase-1 (i.e., IDO inhibitor). The IDO1 enzyme is activated in many human cancers in tumor, stromal and innate immune cells where its expression tends to be associated with poor prognosis. Its role in immunosuppression is multifaceted, involving the suppression of CD8+T effector cells and natural killer cells as well as increased activity of CD4+ T regulatory cells (Treg) and myeloid-derived suppressor cells (MDSC). In tumor neovascularization, IDO1 acts as a key node at the regulatory interface between IFN-γ and IL-6 that shifts the inflammatory milieu towards promoting new blood vessel development. See, for example, Prendergast, George C., et al. "Discovery of IDO1 inhibitors: from bench to bedside." Cancer research 77.24 (2017): 6795-6811. Thus, embodiments herein can comprise a therapeutic combination of a PARP inhibitor compound and an IDO inhibitor. For example, the IDO inhibitor can be a small molecule inhibitor, such as Epacadostat, Indoximod, and Navoximod.

A therapeutically effective amount of a compound, an antibody, or a combination thereof, can relate generally to the amount needed to achieve a therapeutic objective. Referring to the examples herein, therapeutically effective amounts of a PARP-1 inhibitor and an immunotherapy are shown to achieve an objective of reducing tumor growth. Therapeutically effective amounts can depend on the severity and course of the cancer, previous therapy, the subject's health status, weight, and response to the drugs, and the judgment of the treating physician. Prophylactically effective amounts depend on the subjects state of health, weight, the severity and course of the disease, previous therapy, response to the drugs, and the judgment of the treating physician.

In some embodiments, the PARP inhibitor compound is administered to the subject on a regular basis, e.g., three times a day, two times a day, once a day, every other day or every 3 days. In other embodiments, the PARP inhibitor compound is administered to the subject on an intermittent basis, e.g., twice a day followed by once a day followed by three times a day; or the first two days of every week; or the first, second and third day of a week. In some embodiments, intermittent dosing is as effective as regular dosing. In further or alternative embodiments, the PARP inhibitor compound is administered only when the patient exhibits a particular symptom, e.g., the onset of pain, or the onset of a fever, or the onset of an inflammation, or the onset of a skin disorder. If two or more compounds are administered, dosing schedules of each compound can depend on the other or can be independent of the other.

In an embodiment, the administration of the PARP inhibitor compound can be administered chronically, that is, for an extended period of time, including throughout the duration of the subject's life in order to ameliorate or otherwise control or limit the symptoms of the subject's disorder.

In another embodiment, the administration of the PARP inhibitor compound can be given continuously; alternatively, the dose of drug being administered can be temporarily reduced or temporarily suspended for a certain length of time (i.e., a "drug holiday"). The length of the drug holiday can vary between 2 days and 1 year, including by way of example only, 2 days, 3 days, 4 days, 5 days, 6 days, 7 days, 10 days, 12 days, 15 days, 20 days, 28 days, 35 days, 50 days, 70 days, 100 days, 120 days, 150 days, 180 days, 200 days, 250 days, 280 days, 300 days, 320 days, 350 days, or 365 days. The dose reduction during a drug holiday may be from 10%-100%, including, by way of example only, 10%, 15%, 20%, 25%, 30%, 35%, 40%, 45%, 50%, 55%, 60%, 65%, 70%, 75%, 80%, 85%, 90%, 95%, or 100%.

In embodiments, a maintenance regimen can be administered if necessary, such as once a subject's condition has improved. Subsequently, the dosage or the frequency of administration of the PARP inhibitor compound can be reduced, for example as a function of the symptoms or tumor size, to a level at which the individual's improved condition is retained. Individuals can, however, require intermittent treatment on a long-term basis upon any recurrence of symptoms.

The amount of the PARP inhibitor compound administered to a subject can vary depending upon factors such as the particular compound, cancer and its severity, the identity (e.g., weight) of the subject or host in need of treatment, and is determined according to the particular circumstances surrounding the case, including, e.g., the specific agents being administered, the routes of administration, the tumor being treated, and the subject or host being treated. In general, however, doses employed for adult human treatment will typically be in the range of about 0.02 mg per day to about 50 mg/day, or from about 1 mg per day to about 30 mg per day. For example, embodiments of the invention comprise a dose of about 0.1 mg per day, about 1 mg per day, about 5 mg per day, about 10 mg per day, about 15 mg per day, about 20 mg per day, about 25 mg per day, about 30 mg per day, about 35 mg per day, about 40 mg per day or about 50 mg per day. The desired dose of each compound can be presented in a single dose or as divided doses administered simultaneously (or over a short period of time) or at appropriate intervals, for example as two, three, four or more sub-doses per day.

The PARP inhibitor compound can be provided in a unit dosage form suitable for single administration of precise dosages. The unit dosage may be in the form of a package containing discrete quantities of the compound. Non-limiting examples are packaged tablets or capsules, and powders in vials or ampoules. Aqueous suspension compositions can be packaged in single-dose non-reclosable containers. Alternatively, multiple-dose reclosable containers can be used, in which case it is typical to include a preservative in the composition. By way of example only, formulations for parenteral injection may be presented in unit dosage form, which include, but are not limited to ampoules, or in multi-dose containers, with an added preservative.

It is understood that a medical professional will typically determine the dosage regimen in accordance with a variety of factors. These factors include the cancer and/or tumor from which the subject suffers, the degree of metastasis, as well as the age, weight, sex, diet, and medical condition of the subject.

Aspects of the invention are further drawn to methods of administering a PARP inhibitor compound at a metronomic dose.

Metronomic Therapy

The invention also provides metronomic dosing regime. There is provided a method of administering to a subject a composition comprising a dose of a PARP inhibitor compound (such as olaparib) based on a metronomic dosing regime. The methods are applicable to methods of treatment that can provide clinical benefit, defined broadly as any of the following: inhibiting an increase in tumor volume, slowing or inhibiting worsening or progression of cancer cell proliferation, inducing tumor regression, reducing primary tumor size, reducing occurrence or size of metastasis, reducing or stopping tumor growth, inhibiting tumor cell division, killing a tumor cell, inducing apoptosis in a tumor cell, reducing or eliminating tumor recurrence.

"Metronomic dosing regime" can refer to frequent administration of a PARP inhibitor compound without prolonged breaks (or drug holidays) at a dose below the established maximum tolerated dose (MTD) via a traditional schedule with breaks (hereinafter also referred to as a "standard MTD schedule" or a "standard MTD regime"). In metronomic dosing, the same, lower, or higher cumulative dose over a certain time period as would be administered via a standard MTD schedule may ultimately be administered. In some cases, this is achieved by extending the time frame and/or frequency during which the dosing regime is conducted while decreasing the amount administered at each dose. Generally, the PARP inhibitor compound administered via the metronomic dosing regime of the present invention is better tolerated by the individual. Metronomic dosing can also be referred to as maintenance dosing or chronic dosing.

In some variations, there is provided a method of administering a composition comprising a PARP inhibitor compound, wherein the PARP inhibitor compound is administered over a period of time, such as at least one month, wherein the interval between each administration is no more than about 1 day, about 2 days, about 3 days, about 4 days, about 5 days, about 6 days, about 7 days, about 14 days, about 28 days, and wherein the dose of the PARP inhibitor compound at each administration is about 0.25% to about 50% of its maximum tolerated dose following a traditional dosing regime. In embodiments, the dose of the PARP inhibitor compound at each administration is about 0.25% to about 35% of its maximum tolerated dose following a traditional dosage regimen. In some variations, the dosing of the PARP inhibitor compound (such as olaparib) per administration is less than about any of 1%, 2%, 3%, 4%, 5%, 6%, 7%, 8%, 9%, 10%, 11%, 12%, 13%, 14%, 15%, 18%, 20%, 22%, 24%, 25%, 27%, 30%, 32%, 35%, 40%, 45%, or 50% of the MTD for the same PARP inhibitor compound in the same formulation following a given traditional dosing schedule. Traditional dosing schedule refers to the dosing schedule that is generally established in a clinical setting, and depends on the PARP inhibitor administered to the subject. For example, a traditional dosing schedule for PARP inhibitor compound can be 100 mg-300 mg compound (depending on the PARP inhibitor) twice a day. As another example, the maximum tolerated dose of Talazoparib is administered as 1 mg/day.

In some variations, the dosing of the PARP inhibitor compound per administration is between about 0.25% to about 25% of the corresponding MTD value, including for example any of about 0.25% to about 20%, about 0.25% to about 15%, about 0.25% to about 10%, of the corresponding MTD value. The MTD value for a PARP inhibitor compound following a traditional dosing schedule is known or can be easily determined by a person skilled in the art.

In some variations, there is provided a method of administering a composition comprising a PARP inhibitor compound, wherein the PARP inhibitor compound is administered over a period of at least one month, wherein the interval between each administration is no more than about a week. For example, the interval between each administration may be no more than about 1 day, no more than about 2 days, no more than about 3 days, no more than about 4 days, no more than about 5 days, no more than about 6 days, or no more than about 7 days.

Dosing frequency for the PARP inhibitor compound includes, but is not limited to, at least about any of once a week, twice a week, three times a week, four times a week, five times a week, six times a week, or daily. Typically, the interval between each administration is less than about a week, such as less than about any of 6, 5, 4, 3, 2, or 1 day. In some variations, the interval between each administration is constant. For example, the administration can be carried out daily, every two days, every three days, every four days, every five days, or weekly. In some variations, the administration can be carried out twice daily, three times daily, or more frequent.

The metronomic dosing regimes described herein can be extended over an extended period of time, such as from about a month, up to about three years, or longer than 3 years. For example, the dosing regime can be extended over a period of any of about 2, 3, 4, 5, 6, 7, 8, 9, 10, 11, 12, 18, 24, 30, and 36 months. Generally, there are no breaks in the dosing schedule.

The cumulative dose of the PARP inhibitor compound administered by the metronomic regime may be higher than that administered according to a standard MTD dosing schedule over the same time period. In some variations, the cumulative dose of the PARP inhibitor compound administered by the metronomic regime equals to or is lower than that of the PARP inhibitor compound administered according to a standard MTD dosing schedule over the same time period.

It is understood that the teaching provided herein is for examples only, and that metronomic dosing regime can be routinely designed in accordance with the teachings provided herein and based upon the individual standard MTD schedule, and that the metronomic dosing regime used in these experiments merely serves as one example of possible changes in dosing interval and duration which are made to a standard MTD schedule to arrive at an optimal metronomic dosing regime.

The metronomic dosing regime described herein may be used alone as a treatment of a proliferative disease, or carried out in a combination therapy context, such as the combination therapies described herein. For example, the metronomic dosing regime described herein may be carried out in a combination therapy with at least one additional anti-cancer therapy, such as an anti-PD1 immunotherapy (e.g., checkpoint blockade targets) or an IDO inhibitor.

In some variations, the metronomic therapy dosing regime may be used in combination or conjunction with other established therapies administered via standard MTD regimes. By "combination or in conjunction with" it is meant that the metronomic dosing regime of the present invention is conducted either at the same time as the standard MTD regime of established therapies, or between courses of induction therapy to sustain the benefit accrued to the individual by the induction therapy, the intent is to continue to inhibit tumor growth while not unduly compromising the individual's health or the individual's ability to withstand the next course of induction therapy. For example, a metronomic dosing regime may be adopted after an initial short course of MTD chemotherapy.

In some variations, the PARP inhibitor compound is administered at least about any of 1×, 2×, 3×, 4×, 5×, 6×, 7× (i.e., daily) a week. In some variations, the intervals between each administration are less than about any of 7 days, 6 days, 5 days, 4 days, 3 days, 2 days, and 1 day. In some variations, the PARP inhibitor compound is administered over a period of at least about any of 2, 3, 4, 5, 6, 7, 8, 9, 10, 11, 12, 18, 24, 30 and 36 months.

Compounds, Pharmaceutical Formulations, and Compositions

Described herein are methods of treating a subject afflicted with a tumor and/or cancer comprising administering to a subject a low dose of a PARP inhibitor compound.

As described herein, the term "PARP" is used herein to refer to a family of proteins of the enzyme poly(ADP-ribose) polymerase. For example, the PARP can be poly (ADP-ribose) polymerase-1 (PARP-1) or poly (ADP-ribose) polymerase-2 (PARP-2).

The phrase "inhibition of PARP" can refer to inhibiting or reducing the activity of one or more enzymes of the poly (ADP-ribose) polymerase (PARP) family. For example, a PARP-1 inhibitor will inhibit or reduce the activity of the PARP-1 protein. In embodiments, the activity of the PARP-1 protein is reduced by about 5%, about 10%, about 20%, about 30%, about 40%, about 50%, about 60%, about 70%, about 80%, about 90% or about 100%. In embodiments, the amount of PARP mRNA and/or PARP protein is reduced by the PARP inhibitor (such as by siRNA, for example). In other embodiments, the amount of PARP mRNA and/or PARP protein is not reduced, but the activity of the enzyme itself is reduced or inhibited.

Definition of standard chemistry terms are found in reference works, including Carey and Sundberg "ADVANCED ORGANIC CHEMISTRY 4$^{TH}$ ED." Vols. A (2000) and B (2001), Plenum Press, New York, the entire contents of which are incorporated herein by reference. Unless otherwise indicated, conventional methods of mass spectroscopy, NMR, HPLC, protein chemistry, biochemistry, recombinant DNA techniques and pharmacology, within the skill of the art can be employed. Unless specific definitions are provided, the nomenclature employed in connection with, and the laboratory procedures and techniques of, analytical chemistry, synthetic organic chemistry, and medicinal and pharmaceutical chemistry described herein are those known in the art. Standard techniques are optionally used for chemical syntheses, chemical analyses, pharmaceutical preparation, formulation, and delivery, and treatment of patients.

The PARP inhibitor compounds described herein can be selective for PARP-1, but can also be selective for PARP-2, PARP-3, or any combination of PARP-1, PARP-2, and/or PARP-3 (such as rucaparib). In embodiments, the PARP inhibitor compound is a PARP-1 inhibitor compound. In embodiments, the PARP inhibitor compound is a PARP-1/PARP-2 inhibitor compound. In still other embodiments, the PARP inhibitor compound is a PARP-1/PARP-2/PARP-3 inhibitor compound.

In an embodiment, the PARP inhibitor compound is a compound of Formula (I).

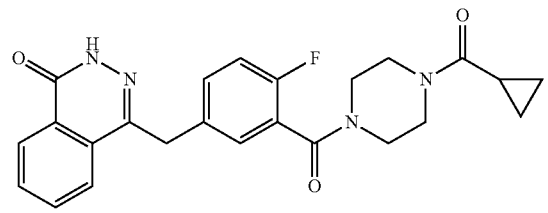 [SMILES: O=C(c1cc(Cc2n[nH]c(=O)c3ccccc23)ccc1F)N1CCN(C(=O)C2CC2)CC1]

In some embodiments, the PARP inhibitor is Olaparib (i.e., AZD, Lynparza). Non-limiting examples of other PARP inhibitors comprise nicotinamide analogues (such as 3-Aminobenzamide), TIQ-A, NU1025, PJ-34, AIQ, PD12873, ABT-888, AG014699, among others.

In an embodiment, the PARP inhibitor compound is a compound of Formula (II):

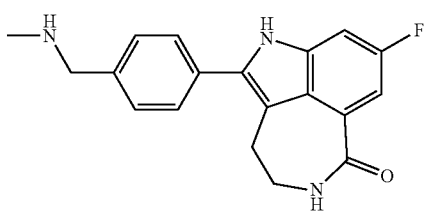 [SMILES: CNCc1ccc(-c2[nH]c3cc(F)cc4c3c2CCNC4=O)cc1]

In an embodiment, the PARP inhibitor is Rucaparib (i.e., Rubraca).

In an embodiment, the PARP inhibitor compound is a compound of Formula (III):

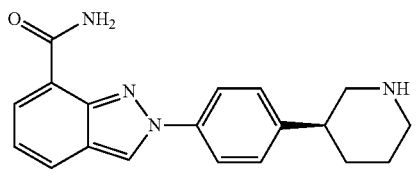 [SMILES: NC(=O)c1cccc2cn(-c3ccc([C@@H]4CCCNC4)cc3)nc12]

In an embodiment, the PARP inhibitor is Niraparib (i.e., Zejula).

In an embodiment, the PARP inhibitor compound is a compound of Formula (III):

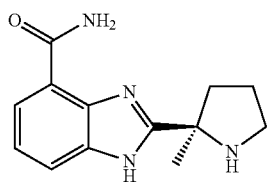 [SMILES: C[C@]1(c2nc3c(C(N)=O)cccc3[nH]2)CCCN1]

In an embodiment, the PARP inhibitor is Velaparib.

Pharmaceutical compositions comprising a PARP inhibitor compound can be formulated in a conventional manner using one or more physiologically acceptable carriers including excipients and auxiliaries which facilitate processing of the active compounds into preparations which can be used pharmaceutically. Proper formulation is dependent upon the route of administration chosen. A summary of pharmaceutical compositions described herein is found, for example, in Remington: The Science and Practice of Pharmacy, Nineteenth Ed (Easton, Pa.: Mack Publishing Company, 1995); Hoover, John E., Remington's Pharmaceutical Sciences, Mack Publishing Co., Easton, Pa. 1975; Liberman, H. A. and Lachman, L., Eds., Pharmaceutical Dosage Forms, Marcel Decker, New York, N.Y., 1980; and Pharmaceutical Dosage Forms and Drug Delivery Systems, Seventh Ed. (Lippincott Williams & Wilkins 1999), the entire contents of which are incorporated by reference herein in their entireties.

PARP inhibitor compounds can be incorporated into pharmaceutical compositions suitable for administration to a subject. A pharmaceutical composition can refer to a mixture of a PARP inhibitor compound with other chemical components, such as carriers, stabilizers, diluents, dispersing agents, suspending agents, thickening agents, and/or excipients. The use of such media and agents for pharmaceutically active substances is well known in the art. Any conventional media or agent that is compatible with the active compound can be used. Supplementary active compounds can also be incorporated into the compositions.

For example, such compositions can comprise a compound of formula (I) and a pharmaceutically acceptable carrier. In embodiments, the composition comprises a PARP inhibitor and a pharmaceutically acceptable carrier. For example, non-limiting examples of pharmaceutically acceptable carriers comprise solid or liquid fillers, diluents, and encapsulating substances, including but not limited to lactose, dextrose, sucrose, sorbitol, mannitol, xylitol, erythritol, maltitol, starches, gum acacia, alginate, gelatin, calcium phosphate, calcium silicate, cellulose, methyl cellulose, microcrystalline cellulose, polyvinylpyrrolidone, water, methyl benzoate, propyl benzoate, talc, magnesium stearate, and mineral oil.

Pharmaceutical compositions can be manufactured in a conventional manner, such as, by way of example only, by means of conventional mixing, dissolving, granulating, dragee-making, levigating, emulsifying, encapsulating, entrapping or compression processes.

The pharmaceutical compositions described herein can be administered by any suitable administration route, including but not limited to, oral, interparenteral, parenteral (e.g., intravenous, subcutaneous, intramuscular), intraperitoneal, intranasal, buccal, topical, rectal, or transdermal administration routes.

The pharmaceutical compositions described herein are formulated into any suitable dosage form, including but not limited to, aqueous oral dispersions, liquids, gels, syrups, elixirs, slurries, suspensions and the like, for oral ingestion by an individual to be treated, solid oral dosage forms, aerosols, controlled release formulations, fast melt formulations, effervescent formulations, lyophilized formulations, tablets, powders, pills, dragees, capsules, delayed release formulations, extended release formulations, pulsatile release formulations, multiparticulate formulations, and mixed immediate release and controlled release formulations. In some embodiments, the compositions are formulated into capsules. In some embodiments, the compositions are formulated into solutions (for example, for IV administration).

For example, pharmaceutical compositions suitable for injectable use include sterile aqueous solutions (where water soluble) or dispersions and sterile powders for the extemporaneous preparation of sterile injectable solutions or dispersions. For intravenous administration, for example, suitable carriers include physiological saline, bacteriostatic water, Cremophor EM™ (BASF, Parsippany, N.J.) or phosphate buffered saline (PBS). In all cases, the composition must be sterile and should be fluid to the extent that easy syringability exists. It must be stable under the conditions of manufacture and storage and must be preserved against the contaminating action of microorganisms such as bacteria and fungi. The carrier can be a solvent or dispersion medium containing, for example, water, ethanol, a pharmaceutically acceptable polyol like glycerol, propylene glycol, liquid polyetheylene glycol, and suitable mixtures thereof. The proper fluidity can be maintained, for example, by the use of a coating such as lecithin, by the maintenance of the required particle size in the case of dispersion and by the use of surfactants. Prevention of the action of microorganisms can be achieved by various antibacterial and antifungal agents, for example, parabens, chlorobutanol, phenol, ascorbic acid, and thimerosal. In many cases, it can be useful to include isotonic agents, for example, sugars, polyalcohols such as mannitol, sorbitol, sodium chloride in the composition. Prolonged absorption of the injectable compositions can be brought about by including in the composition an agent which delays absorption, for example, aluminum monostearate and gelatin.

Sterile solutions can be prepared by incorporating the compound in the required amount in an appropriate solvent with one or a combination of ingredients, such as those described herein, as required, followed by filtered sterilization. Generally, dispersions are prepared by incorporating the active compound into a sterile vehicle which contains a basic dispersion medium and the required other ingredients from those enumerated herein. In the case of sterile powders for the preparation of sterile injectable solutions, examples of useful preparation methods are vacuum drying and freeze-drying which yields a powder of the active ingredient plus any additional ingredient from a previously sterile-filtered solution thereof.

The pharmaceutical solid dosage forms described herein optionally include one or more pharmaceutically acceptable additives such as a compatible carrier, binder, filling agent, suspending agent, flavoring agent, sweetening agent, disintegrating agent, dispersing agent, surfactant, lubricant, colorant, diluent, solubilizer, moistening agent, plasticizer, stabilizer, penetration enhancer, wetting agent, anti-foaming agent, antioxidant, preservative, or one or more combination thereof.

In still other aspects, using standard coating procedures, such as those described in Remington's Pharmaceutical Sciences, 20th Edition (2000), a film coating is provided around the compositions. In some embodiments, the compositions are formulated into particles (for example for administration by capsule) and some or all of the particles are coated. In some embodiments, the compositions are formulated into particles (for example for administration by capsule) and some or all of the particles are microencapsulated. In some embodiments, the compositions are formulated into particles (for example for administration by capsule) and some or all of the particles are not microencapsulated and are uncoated.

Kits

Described herein are methods of treating tumors and/or cancers comprising administering to a subject a low dose of a PARP inhibitor compound.

For use in therapeutic methods described herein, kits and articles of manufacture are also described herein. In some embodiments, such kits include a carrier, package, or container that is compartmentalized to receive one or more containers such as vials, tubes, and the like, each of the container(s) including one of the separate elements to be used in a method described herein. Suitable containers include, for example, bottles, vials, syringes, and test tubes. The containers can be formed from a variety of materials such as glass or plastic.

The articles of manufacture provided herein contain packaging materials. Examples of pharmaceutical packaging materials include, but are not limited to, blister packs, bottles, tubes, inhalers, pumps, bags, vials, containers, syringes, bottles, and any packaging material suitable for a selected formulation and intended mode of administration and treatment. A wide array of formulations of the compounds and compositions provided herein are contemplated as are a variety of treatments for any disorder that benefit by inhibition of PARP-1, or in which PARP-1 is a mediator or contributor to the symptoms or cause.

For example, a container may include a compound of Formula (I) and one or more additional compounds. The container(s) optionally have a sterile access port (for example the container is an intravenous solution bag or a vial having a stopper pierceable by a hypodermic injection needle). Such kits optionally comprising a compound with an identifying description or label or instructions relating to its use in the methods described herein.

A kit will typically include one or more additional containers, each with one or more of various materials (such as reagents, optionally in concentrated form, and/or devices) desirable from a commercial and user standpoint for use of a compound described herein. Non-limiting examples of such materials include, but not limited to, buffers, diluents, filters, needles, syringes; carrier, package, container, vial and/or tube labels listing contents and/or instructions for use, and package inserts with instructions for use. A set of instructions will also typically be included.

In some embodiments, a label is on or associated with the container. A label can be on a container when letters, numbers or other characters forming the label are attached, molded or etched into the container itself; a label can be associated with a container when it is present within a receptacle or carrier that also holds the container, e.g., as a package insert. A label can be used to indicate that the contents are to be used for a specific therapeutic application. The label can also indicate directions for use of the contents, such as in the methods described herein.

In certain embodiments, a pharmaceutical composition comprising a PARP inhibitor is presented in a pack or dispenser device which can contain one or more unit dosage forms. The pack can for example contain metal or plastic foil, such as a blister pack. The pack or dispenser device can be accompanied by instructions for administration. The pack or dispenser can also be accompanied with a notice associated with the container in form prescribed by a governmental agency regulating the manufacture, use, or sale of pharmaceuticals, which notice is reflective of approval by the agency of the form of the drug for human or veterinary administration. Such notice, for example, can be the labeling approved by the U.S. Food and Drug Administration for prescription drugs, or the approved product insert. Compositions containing a compound provided herein formulated in a compatible pharmaceutical carrier can also be prepared, placed in an appropriate container, and labeled for treatment of an indicated condition.

EXAMPLES

Examples are provided below to facilitate a more complete understanding of the invention. The following examples illustrate the exemplary modes of making and practicing the invention. However, the scope of the invention is not limited to specific embodiments disclosed in these Examples, which are for purposes of illustration only, since alternative methods can be utilized to obtain similar results.

Example 1

Complex Roles for PARP-1 in Colon Cancer, Inflammation, and Tumor Immunity: Harnessing these Roles to Modulate Cancer One of the critical objectives of our laboratory is to test the hypothesis that DNA repair enzymes such as PARP-1 play important roles in not only cancer-related processes but also in the pathogenesis of many inflammatory diseases. Without wishing to be bound by theory, the function of PARP-1 in cancers is intimately related to its role in providing alternative and efficient pathways to cancer cells to survive especially for those associated with defects in DNA repair (e.g. triple negative breast and ovarian cancers), however, its role in inflammation may be very different. The role of PARP-1 in DNA repair requires full activity of the enzyme as partial inhibition of PARP-1 has not been associated with defects in DNA repair. The purpose of the present studies is to clarify the roles of PARP-1 in colon inflammation and cancer and determine whether they are related.

Figure 1:
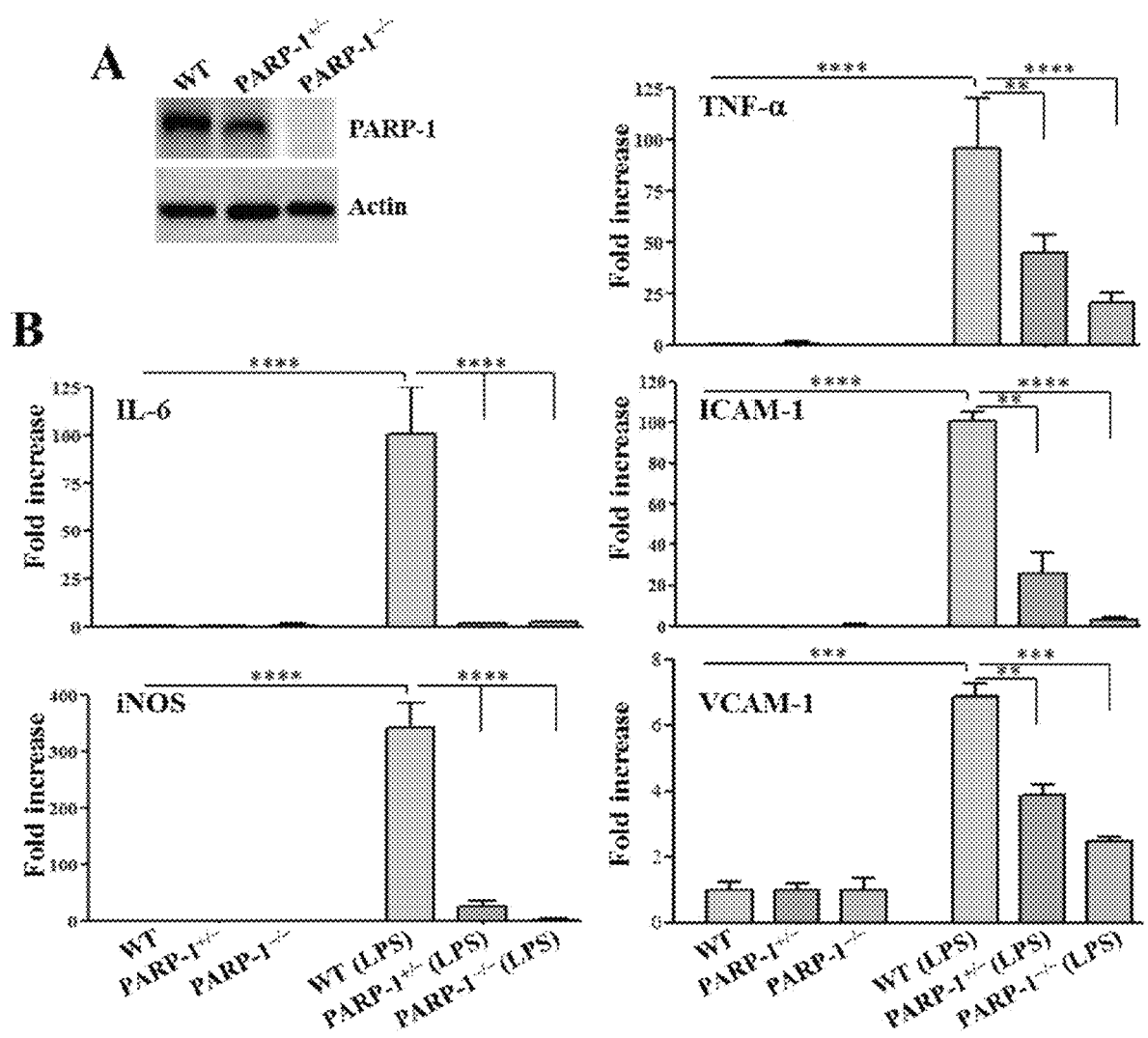
FIG. 1 shows the partial PARP-1 inhibition is sufficient to block expression of inflammatory genes in LPS-treated colon epithelial cells. Primary colon epithelial cells were isolated from WT, PARP-1+/−, or PARP-1−/− mice. (A) Protein extracts were subjected to immunoblot analysis with antibodies to PARP-1 or actin (Note that PARP-1+/− expressed ~50% of PARP-1 shown in WT cells. (B) Cells were treated with 2 mg/ml LPS. RNA was extracted then analyzed by real-time PCR. (C) Cells were treated with 10 ng/ml TNF-a. Protein extracts were subjected to immunoblot analysis with antibodies to COX-2, VCAM-1, or actin.

Referring to FIG. 1, for example, we show that partial PARP-1 inhibition (50%) was very effective at reducing or even blocking expression of inflammatory genes in response to LPS or TNF-α treatment and that complete inhibition of the enzyme was not necessary to achieve maximal effects.

This appears to be due, in part, to a reduction in NF-κB-signal transduction. The remarkable anti-inflammatory effects of PARP-1 inhibition (partial or total) suggested that such inhibition would be protective against chronic inflammation-driven colon carcinogenesis.

Referring to FIG. 2, for example, surprisingly, partial PARP-1 inhibition by gene heterozygosity was more efficient than complete inhibition by gene knockout at reducing chronic inflammation-driven colon tumorigenesis using an azoxymethane (AOM) followed by dextran sulfate sodium (DSS) exposure-based model of the condition although both genotypes provided similar reduction in the levels of systemic and colonic inflammation.

Referring to FIG. 5, for example, when a mutation in the 0-catenin pathway ($Apc^{Min}$) was the main driver for intestinal tumorigenesis, partial PARP-1 inhibition by gene heterozygosity or olaparib protected against the tumor burden in $Apc^{Min/+}$ mice while complete inhibition by gene knockout aggravated the burden. These differential effects were not mirrored with respective effects on systemic or intestinal inflammation, splenomegaly, or cachexia as all conditions lowered the aforementioned traits.

Referring to FIG. 20, for example, using an MCA-38 colon carcinoma cell-allograft mouse model, we show that the opposing effects of PARP-1 gene dosages on intestinal tumorigenesis occurred despite that they both provide a tumor suppressive microenvironment through a regulation of the function of Myeloid-Derived Suppressor Cells (MDSCs). These results exemplify the complexity of the role of PARP-1 in colon tumorigenesis, inflammation, and immunity that could be harnessed to effectively treat not only colon cancer but also others.

Example 2

PARP-1 Heterozygosity Noticeably Protects Against Tumorigenesis in $APC^{min/+}$ Mice.

Without wishing to be bound by theory, this protection can be due, in part, to the anti-inflammatory effects of PARP-1 inhibition at the level of the colon as well as systemically.

Although PARP-1 nullizigosity promotes an anti-inflammatory effect, it actually aggravates tumorigenesis in $APC^{min/+}$ mice. Preliminary studies using CGH analysis suggests that such effects may be associated with an increase in genomic instability, another driving force in colon carcinogenesis.

Using a low and a high doses of the PARP inhibitor olaparib, we were able to reproduce the protective effect of PARP-1 gene heterozygosity but not nullizigosity in $APC^{min/+}$ mice. Of note, using a high dose of olaparib was unreasonably expected to inhibit PARP-1 in a manner similar to that achieved by PARP-1 knockout.

It is noteworthy, however, that the pro-tumorigenic effect of PARP-1 nullizigosity may actually be associated with changes within the transformed colon epithelial cells rather the overall host response. Indeed, PARP-1 nullizigosity promotes a tumor-suppressive rather than a tumor-promoting host response as shown by our results using the MCA-38-allograft model When inflammation is the major driver, PARP-1 inhibition, pharmacologically or by gene knockout, protects against colon tumorigenesis. However, PARP-1 heterozygosity was more protective against AOM/DSS-induced tumor burden than gene knockout. This discrepancy may also be associated with the effect of PARP-1 knockout (not heterozygosity) in genomic instability.

Overall these studies call for a serious caution in the current approach to use PARP inhibitors including olaparib as a therapeutic strategy against colon cancer.

Referring to FIG. 1, for example, colon epithelial cells were treated with TNF-α for the indicated time intervals in the presence or absence 5 μM of the PARP inhibitor AZD2281. Cells were collected and protein extracts were subjected to immunoblot analysis with antibodies to VCAM-1 and COX2. AZD2281 inhibits the expression of inflammatory markers.

PARP-1 heterozygosity decreased tumorigenesis of the APCMin/+ mice, not PARP-1 nullizigosity. (A) Tumor numbers of small and large intestine were counted at 16-week-old of age in APCMin/+ mice (n=13) ApcMin/+ PARP+/− mice (n=14) and APCMin/+ PARP−/−(n=12). (B) Tumors were separated based on their size.

Example 3

Low Doses of PARP Inhibitors as a Novel Strategy to Enhance Anti-Tumor Immunity

The objective is to establish a better understanding of the different aspects of the contribution of poly(ADP-ribose) polymerase-1 (PARP-1) in tumorigenesis in such a way that it can be targeted in cancers other than those with BRCA mutations. Cancers including that of the colon are rank among the most common diseases in the US as well as worldwide with total national expenditure for care of affected individuals exceeding $125 billion. These studies will provide important insights on the utility of PARP inhibitors in targeting cancer cells indirectly by promoting an advantage to the host to use its immune system to attack cancer cells using the drugs at low doses, which reduces the potential for resistance and manifestation of side effects.

Summary

Targeting poly(ADP-ribose) polymerase (PARP) is a new strategy in cancer therapy. For example, this therapy is primarily effective in BRCA-defective cancers (approved for advanced ovarian cancer). The ultimate goal of this current therapy is maximal inhibition of PARP to achieve "synthetic lethality" taking advantage of the inability of BRCA-deficient cancer cells to repair DNA. See FIG. 13, for example. This strategy is limited by the requirement for a constant administration of high doses of the drugs (e.g. olaparib/Lynparza™) and the alarming rise of resistance to the drugs. Past studies on the utility of PARP-1 as a therapeutic target were based on the use of PARP-1$^{-/-}$ mice, very high doses of PARP inhibitors (such as 300 mg/day or more of PARP inhibitors), and immuno-compromised mice. Clinical trials exploring the efficacy of PARP inhibitors on several cancers lead to disappointing results. Because of such focus, many important aspects of PARP inhibition could not be harnessed for full clinical benefits.

Results herein show that partial PARP-1 inhibition (by gene heterozygosity or a low dose of olaparib) provides excellent protection against intestinal tumor burden in $APC^{Min/+}$ mice while extensive inhibition of the enzyme (by gene knockout or a high dose of olaparib) was ineffective or aggravated such burden. These divergent effects occurred despite a blockade in intra-tumoral and systemic inflammation and a promotion of tumor suppressive microenvironment.

Myeloid-Derived Suppressor Cells (MDSCs) recruitment and expansion are major determinants of cancer progression and resistance to therapies by modulating the tumor-killing capacity of the immune system. Results show that PARP-1 plays a key role in MDSC function and that partial inhibition of the enzyme is sufficient to block the suppressive function of these suppressor cells in a MCA-38 cell-based allograft model. Interestingly, anti-tumor immune cells (e.g. T, NK, and dendritic cells) are not affected even with maximal inhibition of PARP-1.

Without wishing to be bound by theory, high doses of PARP inhibitors suppress MDSC function but with a concomitant enhancement of the tumorigenic effects of cancer cells by increasing genomic instability. However, low doses of PARP inhibitors selectively reduce the suppressive activity of MDSCs, decrease inflammation, and provide an advantage to tumor-killing immune cell at reducing/blocking tumor progression without enhancing the tumorigenic traits of cancer cells.

This paradigm-shift will be tested by examining the relationship between PARP-1, its inhibition by decreasing doses of olaparib, and MDSCs differentiation, function, and recruitment to tumors using the allograft model and an ex vivo system. We will then examine whether myeloid-specific or colon epithelial-specific deletion of PARP-1 influences tumorigenesis and MDSC trafficking in a mouse model of $Apc^{Min}$-driven colon cancer. The results of the studies will allow us to establish a foundation on which we can demonstrate that PARP-1 inhibition with low doses of drugs constitutes an extraordinary opportunity to modulate the progression of colon cancer as well as many others by blocking MDSC recruitment and function, which potentially enhances the efficacy of many existing and future immuno-therapeutic strategies.

Description of Work

One of the hallmarks of tumor progression and resistance to therapy is the recruitment of myeloid-derived cells that suppress cancer cell-killing immune cells. Myeloid-Derived Suppressor Cells (MDSCs) recruitment and expansion represent critical events during cancer progression. These cells can influence as well as they can be influenced by the tumor microenvironment. Selective interference with the recruitment and/or function of these cells represents an ideal approach to prevent tumor progression, enhance potency of existing therapies, and promote tumor regression.

Targeting poly(ADP-ribose) polymerase (PARP) is a new strategy in cancer therapy. However, this therapy is primarily effective in BRCA-defective cancers (approved for advanced ovarian cancer). The ultimate goal of this therapy is maximal inhibition of PARP to achieve "synthetic lethality" taking advantage of the inability of BRCA-deficient cancer cells to repair DNA. This strategy is limited by the requirement for a constant administration of high doses of the drugs (e.g. olaparib/Lynparza™) and the premature emergence of resistance to the drugs. Past studies on the utility of PARP-1 as a therapeutic target were based on the use of PARP-1$^{-/-}$ mice, unreasonably high doses of PARP inhibitors, and immuno-compromised mice. Clinical trials exploring the efficacy of PARP inhibitors on several cancers lead to disappointing results. Because of such focus, many important aspects of PARP inhibition could not be harnessed for full clinical benefits.

Results herein show that partial PARP-1 inhibition (by gene heterozygosity or a low dose of olaparib) provides excellent protection against intestinal tumor burden in $APC^{Min/+}$ mice while extensive inhibition of the enzyme (by gene knockout (KO) or a high dose of olaparib) was ineffective or aggravated such burden. These divergent effects occurred despite a blockade in intra-tumoral and systemic inflammation and a promotion of a tumor suppressive microenvironment. Results show that PARP-1 plays a key role in MDSC function and that partial inhibition of the enzyme is sufficient to block the suppressive capacity of these cells in a MCA-38 cell-based allograft model. Interestingly, anti-tumor immune cells such as T, NK, and dendritic cells are not affected by PARP-1 inhibition. More importantly, low doses of olaparib are more effective than high doses in blocking MCA-38-based tumors in WT mice.

Without wishing to be bound by theory, high doses of PARP inhibitors may suppress MDSC function but with a concomitant enhancement of the tumorigenic effects of cancer cells by increasing genomic instability. However, low doses of PARP inhibitors selectively reduce the suppressive activity of MDSCs, decrease inflammation, and provide an advantage to tumor-killing immune cell at reducing/blocking tumor progression without enhancing the tumorigenic traits of cancer cells.

To demonstrate this, we will perform studies using an integrated approach including a MCA-38 colon adenocarcinoma cell-based allograft model and the $APC^{Min}$-based spontaneous intestinal tumorigenesis model. We will take advantage of our newly generated C57BL/6 PARP-1 conditional PARP-1$^{fl/fl}$ mice under the control of hematopoietic cell- or colon epithelial-specific Cre strain. We will also use an ex vivo cell culture model to address some aspects of this invention. Additionally, we will use PARP-1 depletion approaches primarily shRNA-based partial knockdown to mimic PARP-1 gene heterozygosity and CRISPR/Cas9 to mimic PARP-1 knockout on MCA-38 cells.

We will test this paradigm-shift as follows:

1: Examine the relationship between PARP-1, its inhibition by decreasing doses of olaparib, and MDSCs differentiation, intra-tumoral recruitment and function using a MCA-38 colon adenocarcinoma cell-based allograft model and an ex vivo system.

2: Examine whether myeloid-specific or colon epithelial-specific deletion of PARP-1 influences tumorigenesis and MDSC trafficking in a mouse model of ApcMin-driven colon cancer.

The studies will demonstrate that PARP-1 inhibition with low doses of drugs constitutes an extraordinary opportunity to modulate the progression of colon cancer as well as many others by enhancing the efficacy of many existing and future immunotherapeutic strategies.

Research Strategy (a) Significance

A disappointing aspect about the old and new generation cancer therapies is the emergence of drug resistance and the ability of the cancer cell to evade the immune system. PARP inhibitors are emerging as a promising therapy for several human cancers especially those driven by deficiencies in non-PARP-associated DNA repair[1]. Indeed, olaparib (Lynparza™) is now approved as a monotherapy for patients with advanced BRCA1-mutated ovarian cancer. Interestingly, several preclinical and clinical studies offered some hope for PARP inhibitors in the treatment of other cancers with no obvious mutations in BRCA[2]. Unfortunately, many of the clinical trials failed. Recently, olaparib was tested in a phase I[3] and a phase II[4] clinical trials on patients with advanced colon cancer as a monotherapy or in combination with irinotecan (Camptosar™), with disappointing results but encouraging more detailed studies. Without wishing to be bound by theory, the reason for the failure of PARP inhibitors in treating non-BRCA1-mutated cancers is the fact that we still do not understand the intricacies of the role of the enzyme in the pathogenesis of cancers including that of the colon.

One of our critical objectives is to unravel the unobvious functions of DNA repair enzymes such as PARP-1 and test the hypothesis that these enzymes play important roles not only in cancer cell-related processes (DNA repair, cell death, genomic integrity, etc.) but also in inflammatory and immune responses. The function of PARP-1 in cancers may be intimately related to its ability to provide an alternative pathway for cancer cells to survive especially for those associated with defects in DNA repair[5]; however, the mechanism by which it contributes to inflammation may be very different. The role of PARP-1 in DNA repair requires the full activity of the enzyme as partial inhibition of PARP-1 has not been associated with major defects in DNA repair[1]. Indeed, PARP-1 heterozygous cells or mice behave similarly to DNA damaging agents as the WT counterparts[6]. Interestingly, we reported that PARP-1 heterozygosity (which reduces PARP-1 by ~50%) or low doses of a PARP inhibitor substantially blocks atherosclerosis in high fat diet-fed ApoE$^{-/-}$ mice[7]. We have also shown that low doses of PARP inhibitors, including olaparib, protect against asthma[7-11].

MDSCs play a critical role in providing an advantage to cancer cells to evade the immune system[12]. These cells are specialized in blocking T cell function by promoting the expansion of $T_{Reg}$ cells, depriving T cells of essential aminoacids, producing oxidizing molecules (e.g. $H_2O_2$ and $ONOO^-$), and blocking T cell recruitment to tumors[13]. As most cancers, colon cancer is also characterized by the infiltration with immune cell types (e.g. T cells)[14]. However, because of MDSCs, these cells are dysfunctional. Therefore, interfering with the function and/or recruitment of MDSCs might provide tremendous benefit to strategies targeting cancer cells, representing an attractive strategy to treat not only colon cancer but also many others. Our data suggest that MDSCs are highly sensitive to PARP-1 inhibition and thus can be targeted with low doses of PARP inhibitors. These findings are highly significant because they provide a potential solution that can benefit not only patients with colon cancer but also those with other types of cancers using FDA-approved PARP inhibitors at low doses. This approach would certainly eliminate the possibility of drug resistance and enhance the efficacy of many existing and future immunotherapies.

(b) Innovation

Current therapeutic strategies aim at maximally inhibiting PARP, such as with high doses of PARP inhibitor compounds. Embodiment as described herein, which use low doses of the drugs to target MDSCs while preserving the function of cancer-killing immune cells, are novel and represent a paradigm-shifting concept.

(c) Results

Partial PARP-1 inhibition is sufficient to block expression of inflammatory genes in primary colon epithelial cells (CECs) upon LPS or TNF exposure. We developed a highly reproducible method to isolate CECs from mice[15, 16] and humans. FIG. 14(A) shows the square/hexagonal-shaped cells indicative of the epithelial nature of the cells (additional characterization of cells is described in[16]). FIG. 14(B) shows that PARP-1 heterozygosity reduces PARP-1 expression by ~50% compared to that of WT cells[7, 17]. PARP-1 heterozygosity was as effective as KO in reducing TNF, IL-6, and ICAM-1 in response to LPS (FIG. 14(C)) or TNF (FIG. 14(D)) as assessed by qRT-PCR.

Partial PARP-1 inhibition by gene heterozygosity is more efficient than KO at reducing chronic inflammation-driven colon tumorigenesis in mice despite an equal modulation of systemic inflammation. A single administration of the carcinogen azoxymethane (AOM) to animals in combination of 4 cycles of treatment with 2% dextran sulfate sodium (DSS) is a reliable chronic inflammation-induced colon cancer model. A single dose of AOM (FIG. 2A and [18, 19]) or the 4 cycles of DSS treatment are insufficient to induce tumorigenesis[20]. AOM/DSS treatment induced ~7-8 tumors in colons of WT mice (FIG. 15(A)). This burden was lower in PARP-1$^{+/-}$ counterparts but, surprisingly, much lower in PARP-11$^{+/-}$ mice. The tumors from AOM/DSS-treated PARP-1$^{-/-}$ mice were not different from those of similarly treated WT mice (FIG. 15 (B)). High PCNA immunoreactivity (a marker of cell proliferation) was detected in tumors of AOM/DS S-treated WT and PARP-1$^{-/-}$ mice, which was much lower in tumors of treated PARP-1$^{+/-}$ mice (p<0.001; FIG. 27). FIG. 15(D) shows that the colonic mucosa was almost completely absent in affected areas. However, the mucosa of AOM/DSS-treated PARP-1$^{+/-}$ or PARP-1$^{-/-}$ mice showed some disorganization and injury, but the colonic crypts were relatively intact or in the process of recovery. The results on colitis are consistent with[21]. The effects of PARP-1 inhibition on the tumor burden mirrored a decrease in systemic inflammation (FIG. 15(E)). These results show that there are benefits to partially inhibiting PARP-1 and support the notion that aiming at completely inhibiting the enzyme with high doses of PARP inhibitors (in non-BRCA-deficient cancers) may not provide an important clinical value and may become detrimental in the long run.

Partial inhibition of PARP-1 by gene heterozygosity protects against APC$^{Min}$-induced tumor burden in mice while complete inhibition by gene KO aggravates it. We next examined the effect of PARP-1 gene dosage on APC$^{Min}$-induced intestinal tumorigenesis. We generated C57BL/6 PARP-1$^{+/-}$ and PARP-1$^{-/-}$ mice[22] in the APC$^{Min/+}$ background (FIG. 21(A)). PARP-1 heterozygosity provided a remarkable protection against the tumor burden (FIG. 21(B)). Surprisingly, PARP-1 KO not only did not protect against the tumor burden, it significantly aggravated it. FIG. 21(C) shows that PARP-1 heterozygosity completely blocked the generation of large tumors (>4 mm) with a significant concomitant decrease in small and middle size tumors. Conversely, PARP-1 KO promoted an increase in the number of small tumors. Weight loss observed in the APC$^{Min/+}$ mice was prevented by PARP-1 heterozygosity but not KO (FIG. 28). PCNA immunoreactivity in tumors of APC$^{Min/+}$ mice with WT or PARP-1 KO was not different (FIG. 21(D)); but, the difference between these 2 groups and that of PARP$^{+/-}$ mice was highly significant (p<0.01). Paradoxically, intra-tumoral inflammation (VCAM-1 and COX-2; FIG. 21(D) and FIG. 21(E)) was equally reduced in tumors of PARP-1$^{+/-}$ and PARP-1$^{-/-}$ mice.

PARP inhibition with a low dose of olaparib (Lynparza™) is protective against APC$^{Min}$-induced tumor burden in mice while a higher dose of the drug is not. We next examined the effect of a low dose (5 mg/kg) and a five times higher dose (25 mg/kg) of olaparib starting at 8 week of age on APC$^{Min}$-driven tumorigenesis. FIG. 22(A) shows that although PARP inhibition with the low dose of olaparib provided a good protection against the tumor burden, the higher dose showed high variability but overall it provided no protection against the burden. In fact, some mice showed a tumor burden that was higher than that of the vehicle group. The differential effects of the two doses of olaparib on the tumor burden were mirrored by respective effects on cachexia (FIG. 22(B)). The results are relatively consistent with the differential effects attained using the genetic approach. Note that most, if not all, studies examining the effects of olaparib on carcinogenesis using preclinical models have used doses as high as 300 mg/kg/day. We are confident that higher and more frequent doses of olaparib would aggravate the tumor burden in our experimental model.

PARP-1 inhibition genetically (by gene heterozygosity or KO) or by olaparib is effective at blocking systemic inflammation in APC$^{Min/+}$ mice. Chronic inflammation exists in APC$^{Min}$-driven intestinal carcinogenesis (FIG. 23) and[23-25]. All forms of PARP-1 inhibition were able to significantly reduce IL-6 and TNF albeit not to the level of control mice. MCP-1 levels were significantly reduced by PARP-1 inhibition to levels similar to those of WT controls. These results demonstrate that PARP-1 inhibition promote an anti-inflammatory environment.

PARP-1 inhibition provides a tumor-suppressive environment in MCA-38 cell-based allograft model of colon cancer. Given the above results, it became critical to determine whether PARP-1 plays a role in the host response to tumor development. We took advantage of an allograft model using the colon adenocarcinoma cell line MCA-38 (from a C57BL/6 mouse), which is WT for PARP-1 (FIG. 24(A)). FIG. 24(B) and FIG. 24(C) show that grafting of MCA-38 cells onto WT mice leads to formation of large solid tumors; these tumors were significantly smaller when grafted onto PARP-1$^{+/-}$ or PARP-1$^{-/-}$ mice. The anti-tumor effects of PARP-1 gene heterozygosity and KO were accompanied by an efficient reduction in systemic (FIG. 24(C)) and intratumoral (FIG. 24(D)) inflammation as well as reduced CD68$^+$ inflammatory cell recruitment (FIG. 24(E)).

PARP-1 plays a role in MDSC function and its partial PARP-1 inhibition is sufficient to block the suppressive activity of these cells without affecting the function of dendritic cells. Since PARP-1 seems to play an important role in the host response to tumor formation, it may influence the function of MDSCs. To test this, we isolated MDSCs from MCA-38 cell-based tumors (by enzymatic digestion+purification using EasySep Mouse CD11b Positive Selection). Purity of MDSCs was verified by FACS for CD11b and Gr-1 positivity. MDSCs isolated from tumors of WT mice were very effective at suppressing T cell proliferation upon stimulation (FIG. 25(A)). Interestingly, MDSCs derived from tumors of PARP-1$^{+/-}$ or PARP-1$^{-/-}$ mice almost completely failed to suppress the proliferation of these WT T cells. Note that PARP-1 gene heterozygosity was sufficient to impair the function of MDSCs suggesting that they are very sensitive to PARP-1 inhibition.

Also note that PARP-1 inhibition does not modulate indiscriminately all immune cells as it has little to no effect on CD4$^+$ T[11], CD8$^+$ T[27], NK[27], or dendritic (DCs) (FIG. 25(B)) cell populations. We acknowledge that Aldinucci et al.[28] reported a role for PARP in DC maturation; this conclusion was reached using unreasonably high doses of PARP inhibitors (TIQ-A) (20-30 μM), which we showed to be cytotoxic[29].

Low concentrations of olaparib are more effective than high concentrations in blocking MCA-38-based tumors in WT mice. Given the above results, we next speculated that low doses of PARP inhibitors (e.g. olaparib) might be more beneficial than high doses in immunocompetent mice. To this end, WT mice were engrafted with MCA-38 cells and as soon as the tumors were palpable (day 6), mice received 0.2, 1, or 5 mg/kg olaparib or vehicle. Mice that received vehicle increased in size in a time-dependent manner and were sacrificed at day 16. The tumors in mice that received 5 mg/kg olaparib were relatively smaller than those of WT. Remarkably, the tumors in mice that received the lowest dose of olaparib barely increased above the size the tumors at the day 5. The middle dose (1 mg/kg) were very effective at blocking tumor growth; at 16 growth was more visible. These results are extremely important because they provide an unexpected and a novel paradigm-shifting concept with high clinical relevance. These results may also explain why high doses of PARP inhibitors failed to be efficacious against several cancers with no BRCA mutation.

(1) To Decipher the Relationship Between PARP-1, its Inhibition by Decreasing Doses of Olaparib, and MDSCs Differentiation, Intra-Tumoral Recruitment and Function Using the MCA-38 Cell-Based Allograft Model.

1. To Determine the Effects of PARP Inhibition on the Recruitment of MDSCs Using the Allograft Model.

PARP-1 appears to play a role in MDSC function and, without wishing to be bound by theory, this effect may accompany a decrease in MDSCs recruitment to the tumors. For example, PARP-1 inhibition may affect the recruitment of the cells given our reported connection between PARP-1 and CXCR2[30], a receptor required for trafficking to tumors[31].

Specific Experiment 1

MCA-38 cells will be engrafted onto mice as shown in FIG. 24. Tumors will be collected from sacrificed mice on day 15 (or when the size of the tumors is large enough to isolate MDSCs in all groups). Portions of the tumors and spleens will be digested to generate single cell suspension. Cells will be assessed for MDSC numbers by FACS with fluorescently labeled antibodies to CD11b, LyG6(Gr1), or Ly6C. The two latter markers will allow us to determine whether the recruited MDSCs are granulocytic (GrMDSCs) (CD11b$^+$, Ly6G$^{+high}$, Lv6C$^{low}$) or monocytic MoMDSCs) (CD11b$^+$, Ly6C$^{+high}$, Ly6G). Recruitment will be assessed as percent MDSCs of the total number of isolated cells. Given that percentages can be misleading and that the tumor size between groups could be very different, we will correct the numbers according to tumor volume. We will also assess the single cell suspension for the prevalence of cytotoxic CD8$^\square$ T-cell populations (IFNγ$^+$ CD8$^+$ CD3$^+$ CD45$^+$). MDSCs from all groups will also be isolated as described above and subjected to RNA extraction followed by quantitative RT-PCR using primer sets for iNOS and Arg1.

Specific Experiment 2.

To determine whether the tumor microenvironment influenced the differences we may see in the above experiment, a portion of the tumor will be subjected to RNA extraction followed by quantitative RT-PCR using primer sets specific for CXCR2 or CXCR4, GM-CSF, G-CSF, IL-4, IL-6, IL-13, TNF, TGFβ and several others.

2. To Determine Whether Low Doses of Olaparib Prevent Tumor Progression by Decreasing the Recruitment of MDSCs in the Allograft Model.

Specific Experiment 1

We will repeat the experiment described in FIG. 20 with two major alterations: 1) we will keep measuring tumor sizes for a longer period even after the termination of the groups receiving vehicle. This will allow us to have a better idea on how long the effect of the low doses of olaparib can maintain their effects on tumor progression. 2) We will also determine the lowest dose of the drug that can modulate tumor progression in our allograft model. We will continue using a de-escalation of the doses by five-fold increments as described in FIG. 20.

Specific Experiment 2:

While conducting experiment 1, we will assign a group of mice to be sacrificed at day 15 to conduct the same assays described herein, such as in Goal 1.

3. To Determine the Role of PARP-1 and the Effect of Olaparib on Differentiation of MDSCs Ex Vivo.

The results of goal 1 may not differentiate between the effects on MDSCs, other immune cells, and cancer cells. It is, thus, important to determine whether PARP inhibition affects directly differentiation of MDSCs. This becomes even more important when we consider the fact that olaparib as well as other PARP inhibitors affect both PARP-1 and PARP-2. We intend to examine whether PARP-1 expression and/or activity affect differentiation of MDSCs from BM progenitors.

Specific Experiment 1

BM cells will be harvested from WT, PARP-1$^{+/-}$, or PARP-1$^{-/-}$ as in[10], which will then be cultured with G-CSF, GM-CSF, and IL-6[32]. MDSCs will be assessed by FACS for numbers and subtypes. MDSCs will also be positively selected to assess their T-cell suppression capacity and their ability to express iNOS and Arg1 by RT-PCR.

Specific Experiment 2.

A portion of WT or PARP-1$^{-/-}$ BM cells will be cultured in the presence of 1, 0.2, 0.04 µM olaparib (at day 0 and day 2). Again, PARP inhibitors may affect PARP-1 and PARP-2 and thus it becomes important to examine whether the effects of olaparib are associated solely with PARP-1 or may also be related to PARP-2. To address this, we will treat PARP-1$^{-/-}$ BM cells with olaparib as will be done for WT cells. MDSCs from all conditions will be subjected to FACS analysis, purification, T cell suppression capacity, and RT-PCR for iNOS and Arg1.

4. To Determine Whether Partial or Complete Depletion of PARP-1 in Cancer Cells Affects Recruitment of MDSCs to Tumors in the Allograft Model.

We will next address whether PARP-1 plays a role in the ability of tumors to influence MDSC recruitment and activation. We will use shRNA and CRISPR/cas9 approaches on MCA-38 cells for partial and complete depletion, respectively, in a manner similar to that achieved in A549 cells (FIG. 26). Partial knockdown would mimic PARP-1 heterozygosity and deletion with CRISPR/Cas9 would mimic PARP-1 KO.

Specific Experiment.

MCA-38 cells that were subjected to partial knockdown (MCA38-PARP-1$^{shRNA}$) and those to CRISPR/Cas9 (MCA-38-PARP-1$^{CRISPR/Cas9}$) will be engrafted with their respective controls onto opposing flanks of WT mice. Tumor volumes will be assessed as in FIG. 24. At day 15 (or when the size of the tumors is large enough to isolate MDSCs in all groups), tumors will be harvested after sacrificing the mice. The tumors will be divided into equal portions by weight. A portion will be digested to generated single cell suspensions, which will be assessed for MDSCs populations by FACS or for MDSC isolation by positive selection to assess their T-cell suppression capacity or their ability to express iNOS and Arg1. The second portion of the tumors will be assessed for CXCR2 or CXCR4 and a number of inflammatory factors (described in Goal 1 of Aim 1) to determine whatever difference we see between the groups can be attributed to the ability of the cancer cells to produce the factors that are critical for MDSC recruitment and activation.

(2) To examine whether myeloid-specific or colon epithelial-specific deletion of PARP-1 influences tumorigenesis and MDSC trafficking in a mouse model of APC$^{Min}$-driven colon cancer.

Using spontaneous models will provide us with critical information that is of great relevance to the human condition. For the following studies, we have several options, which include different models of colon cancer representing the many aspects and complexity of the human disease. Our lab is very well versed in the APC$^{Min/+}$ mouse model. APC gene mutations are attributed to cases of familial adenomatous polyposis (FAP) as well as approximately ~70% of sporadic colorectal cancer[33-35]. We are also versed with a colon cancer model that is exclusively induced by repeated administrations of the carcinogen DMH[16] or its metabolite AOM. We also have the AOM/DSS model that is induced by chronic colon inflammation (FIG. 15). We will focus on the APC$^{Min}$ model because of its simplicity; however, we can use any of these models as needed, which altogether encompass many aspects of human colon cancer. We will use our new PARP-1-floxed mice under different Cre-strains. The mutant strain was generated (germ line transmission and Neo cassette removal) by Cyagen. We will be crossing the mutant mice with several Cre-strains. We succeeded in generating the floxed-PARP-1 under the control of Tek-Cre (FIG. 10) and termed PARP-1$^{Tek-fl/wt}$ and PARP-1$^{Tek-fl/fl}$ for heterozygous and KO, respectively. We should complete the generation of termed PARP-1$^{CDX2-fl/fl}$ strain rather shortly. These strains will then be crossed with APC$^{Min}$ as in FIG. 21.

1. To Examine Whether Myeloid-Specific PARP-1 Gene Heterozygosity or KO Reduces APC$^{Min}$-Induced Tumor Burden and Determine Whether it Alters Intra-Tumoral MDSC Trafficking and Function.

Specific Experiment

APC$^{Min/+}$/PARP-1$^{Tek-fl/wt}$ and APC$^{Min/+}$/PARP-1$^{Tek-fl/fl}$ mice will be sacrificed at 16 wks of age; we will use the APC$^{Min/+}$/PARP-1$^{fl/fl}$ littermates as WT PARP-1 animals. The tumor burden in the intestinal track will be assessed (numbers and sizes) as described in FIG. 21. Tumors will be collected and subdivided according to their position in the intestinal track. Two third of the tumors and spleens will be digested for single cell suspension. The remaining portion will be processed for RNA and DNA extraction. A small portion of the single suspensions will be assessed by FACS analysis for the number and subtypes of MDSCs. The remaining will be used for MDSC isolation as described above. Isolated MDSCs will be assessed for their T cell suppression capacity or for RNA extraction to assess the expression levels of iNOS and Arg1. Extracted RNA (directly from the tumors or spleens) will be assessed by qPCR with primer sets specific for CXCR2 or CXCR4 and a number of inflammatory factors (described in Goal 1 of Aim 1).

2. To Examine Whether Colon Epithelial Cell-Specific PARP-1 Gene Heterozygosity or KO Alter Apc$^{Min}$-Induced Tumor Burden by Influencing MDSC Trafficking and Function within the Tumor Microenvironment.

Specific Experiment

APC$^{Min/+}$/PARP-1$^{fl/fl}$, APC$^{Min/+}$/PARP-1$^{CDX2-fl/wt}$, APC$^{Min/+}$/PARP-1$^{CDX2-fl/fl}$ mice will be sacrificed at 16 wks of age and processed the same way as described in Goal 1, above.

3. To examine the potential differential effects of colon epithelial cell-specific PARP-1 gene heterozygosity and KO on Apc$^{Min}$-induced tumor burden is associated with changes in genomic instability in tumor cells. We believe that the primary reason for PARP-1 gene KO for aggravating the tumor burden in APC$^{Min/+}$ mice is the accumulation of genomic instability in addition to that induced by the APC$^{Min}$ mutation.

Specific Experiment.

DNA extracted from the tumors of the different experimental groups will be assessed by aCGH essentially as done in our published report[16]. The samples will be analyzed using the Agilent DNA microarray platform. Data including Copy Number Variations will be assessed by Agilent Feature Extraction software 12 and analyzed with Agilent Genomic Workbench software 7.0 using the statistical algorithms z score.

Expected Outcomes:

Without wishing to be bound by theory, we expect that partial PARP-1 inhibition would be effective in reducing the recruitment of MDSCs and their function. It is rather possible that low doses of olaparib block the function of MDSCs but not their recruitment. These potential differential effects are likely given our previous findings showing that low doses of olaparib interferes with T cell-response to CD3/CD28-stimulated production of Th2 inflammatory factors without affecting the signal leading to their proliferation[11]. We may also expect that inhibition of PARP in MDSCs may change their phenotype to acquire an anti-tumor trait in a manner similar to that observed when Chop protein was depleted in MDSCs[38]. This is based on the finding (FIG. 30) that PARP-1 inhibition decreases Chop expression in CD68$^+$ cells in response to oxidized cholesterols.

The effects of PARP-1 inhibition may be even more enhanced if its efficiency in increasing the efficacy of adoptive T cell and checkpoint blockade (e.g. PD-1 or PD-L1)-based therapies is examined. Clinical[39] and preclinical trials[40] have looked into the combination of PARP inhibitors and anti-PD1 therapy but again using high daily doses of the drugs or immunodeficient mice. In some studies, the dose of the PARP inhibitor was as high as 300 mg/kg/day, which is unreasonable and certainly nontherapeutic, as these high doses can be extremely toxic to all cell types including the cancer cells themselves. We believe that here resides the novelty of our hypothesis.

Without wishing to be bound by theory, we expect that the tumor burden to be significantly lower in both PARP-1$^{Tek-fl/wt}$ and PARP-1$^{Tek-fl/fl}$ mice compared to the PARP-1fl/fl (on Apc$^{Min}$ background) controls. This is based on the potential that myeloid cells that are partially or completely deficient in PARP-1 would be unable to induce inflammation even if the tumor cells would produce inflammatory cues. The associated MDSCs would also be incapable of suppressing T cells. It is possible that PARP-1 KO may have some effect on T cell function and if this possibility presents itself, we believe that APC$^{Min/+}$/PARP-1$^{Tek-fl/fl}$ mice would have a higher tumor burden than that of APC$^{Min/+}$/PARP-1$^{Tek-fl/wt}$ mice but would be significantly less than that of the APC$^{Min/+}$/PARP-1$^{fl/fl}$ controls. As for the APC$^{Min/+}$/PARP-1$^{CDX2-fl/wt}$ mice, it would be difficult to predict the outcome. If we consider that the complete absence of PARP-1 in CECs would prevent the production of inflammatory factors necessary for MDSC recruitment; these same cues may be necessary for recruiting cytotoxic T cells. The net outcome would depend on the effect of PARP-1 gene deletion on the cancer cell. If high genomic instability is reached, then one would expect to observed high incidence of tumors (size and/or numbers) in the colon while the tumor burden in the small intestine would remain the same as in the control mice.

REFERENCES CITED IN THIS EXAMPLE

1. Berger N A, Besson V C, Boulares A H, Burkle A, Chiarugi A, Clark R S, Curtin N J, Cuzzocrea S, Dawson™, Dawson V L, Hasko G, Liaudet L, Moroni F, Pacher P, Radermacher P, Salzman A L, Snyder S H, Soriano F G, Strosznajder R P, Sumegi B, Swanson R A, Szabo C. Opportunities for the repurposing of parp inhibitors for the therapy of non-oncological diseases. *Br J Pharmacol.* 2017
2. George A, Kaye S, Banerjee S. Delivering widespread brca testing and parp inhibition to patients with ovarian cancer. *Nature reviews. Clinical oncology.* 2016
3. Chen E X, Jonker D J, Siu L L, McKeever K, Keller D, Wells J, Hagerman L, Seymour L. A phase i study of olaparib and irinotecan in patients with colorectal cancer: Canadian cancer trials group ind 187. *Invest New Drugs.* 2016; 34:450-457
4. Leichman L, Groshen S, O'Neil B H, Messersmith W, Berlin J, Chan E, Leichman C G, Cohen S J, Cohen D, Lenz H J, Gold P, Boman B, Fielding A, Locker G, Cason R C, Hamilton S R, Hochster H S. Phase ii study of olaparib (azd-2281) after standard systemic therapies for disseminated colorectal cancer. *Oncologist.* 2016; 21:172-177
5. Pommier Y, O'Connor M J, de Bono J. Laying a trap to kill cancer cells: Parp inhibitors and their mechanisms of action. *Sci Transl Med.* 2016; 8: 362ps317
6. Wang Z Q, Auer B, Stingl L, Berghammer H, Haidacher D, Schweiger M, Wagner E F. Mice lacking adprt and poly(adp-ribosyl)ation develop normally but are susceptible to skin disease. *Genes & development.* 1995; 9:509-520
7. Oumouna-Benachour K, Hans C P, Suzuki Y, Naura A, Datta R, Belmadani S, Fallon K, Woods C, Boulares A H. Poly(adp-ribose) polymerase inhibition reduces atherosclerotic plaque size and promotes factors of plaque stability in apolipoprotein e-deficient mice: Effects on macrophage recruitment, nuclear factor-kappab nuclear translocation, and foam cell death. *Circulation.* 2007; 115:2442-2450
8. Boulares A H, Zoltoski A J, Sherif Z A, Jolly P, Massaro D, Smulson M E. Gene knockout or pharmacological inhibition of poly(adp-ribose) polymerase-1 prevents lung inflammation in a murine model of asthma. *Am J Respir Cell Mol Biol.* 2003; 28:322-329
9. Oumouna M, Datta R, Oumouna-Benachour K, Suzuki Y, Hans C, Matthews K, Fallon K, Boulares H. Poly(adp-ribose) polymerase-1 inhibition prevents eosinophil recruitment by modulating th2 cytokines in a murine model of allergic airway inflammation: A potential specific effect on il-5. *J Immunol.* 2006; 177:6489-6496
10. Ghonim M A, Pyakurel K, Ibba S V, Al-Khami A A, Wang J, Rodriguez P, Rady H F, El-Bahrawy A H, Lammi M R, Mansy M S, Al-Ghareeb K, Ramsay A, Ochoa A, Naura A S, Boulares A H. Parp inhibition by olaparib or gene knockout blocks asthma-like manifestation in mice by modulating cd4(+) t cell function. *Journal of translational medicine.* 2015; 13:225
11. Ghonim M A, Pyakurel K, Ibba S V, Wang J, Rodriguez P, Al-Khami A A, Lammi M R, Kim H, Zea A H, Davis C, Okpechi S, Wyczechowska D, Al-Ghareeb K, Mansy M S, Ochoa A, Naura A S, Boulares A H. Parp is activated in human asthma and its inhibition by olaparib blocks house dust mite-induced disease in mice. *Clin Sci (Lond)*. 2015; 129:951-962
12. Gabrilovich D I. Myeloid-derived suppressor cells. *Cancer immunology research.* 2017; 5:3-8
13. Al-Khami A A, Rodriguez P C, Ochoa A C. Metabolic reprogramming of myeloid-derived suppressor cells (mdsc) in cancer. *Oncoimmunology.* 2016; 5:e1200771
14. Mei Z, Liu Y, Liu C, Cui A, Liang Z, Wang G, Peng H, Cui L, Li C. Tumour-infiltrating inflammation and prognosis in colorectal cancer: Systematic review and meta-analysis. *Br J Cancer.* 2014; 110:1595-1605
15. Oumouna-Benachour K, Oumouna M, Zerfaoui M, Hans C, Fallon K, Boulares A H. Intrinsic resistance to apoptosis of colon epithelial cells is a potential determining factor in the susceptibility of the a/j mouse strain to dimethylhydrazine-induced colon tumorigenesis. *Mol Carcinog.* 2007; 46:993-1002
16. Errami Y, Brim H, Oumouna-Benachour K, Oumouna M, Naura A S, Kim H, Ju J, Davis C J, Kim J G, Ashktorab H, Fallon K, Xu M, Zhang J, Del Valle L, Boulares A H. Icad deficiency in human colon cancer and predisposition to colon tumorigenesis: Linkage to apoptosis resistance and genomic instability. *PLoS One.* 2013; 8:e57871
17. Kanai M, Tong W M, Wang Z Q, Miwa M. Haploinsufficiency of poly(adp-ribose) polymerase-1-mediated poly(adp-ribosyl)ation for centrosome duplication. *Biochemical and biophysical research communications.* 2007; 359:426-430
18. Nambiar P R, Girnun G, Lillo N A, Guda K, Whiteley H E, Rosenberg D W. Preliminary analysis of azoxymethane induced colon tumors in inbred mice commonly used as transgenic/knockout progenitors. *Int J Oncol.* 2003; 22:145-150
19. Bissahoyo A, Pearsall R S, Hanlon K, Amann V, Hicks D, Godfrey V L, Threadgill D W. Azoxymethane is a genetic background-dependent colorectal tumor initiator and promoter in mice: Effects of dose, route, and diet. *Toxicological sciences: an official journal of the Society of Toxicology.* 2005; 88:340-345
20. Tanaka T, Kohno H, Suzuki R, Yamada Y, Sugie S, Mori H. A novel inflammation-related mouse colon carcinogenesis model induced by azoxymethane and dextran sodium sulfate. *Cancer science.* 2003; 94:965-973
21. Larmonier C B, Shehab K W, Laubitz D, Jamwal D R, Ghishan F K, Kiela P R. Transcriptional reprogramming and resistance to colonic mucosal injury in poly(adp-ribose) polymerase 1 (parp1)-deficient mice. *The Journal of biological chemistry.* 2016; 291:8918-8930
22. Datta R, Naura A S, Zerfaoui M, Errami Y, Oumouna M, Kim H, Ju J, Ronchi V P, Haas A L, Boulares A H. Parp-1 deficiency blocks il-5 expression through calpain-dependent degradation of stat-6 in a murine asthma model. *Allergy.* 2011; 66:853-861
23. Serebrennikova O B, Tsatsanis C, Mao C, Gounaris E, Ren W, Siracusa L D, Eliopoulos A G, Khazaie K, Tsichlis P N. Tpl2 ablation promotes intestinal inflammation and tumorigenesis in apcmin mice by inhibiting il-10 secretion and regulatory t-cell generation. *Proc Natl Acad Sci USA.* 2012; 109:E1082-1091
24. McClellan J L, Davis J M, Steiner J L, Day S D, Steck S E, Carmichael M D, Angela Murphy E. Intestinal inflammatory cytokine response in relation to tumorigenesis in the apcmin/+mouse. *Cytokine.* 2012; 57:113-119
25. Gounaris E, Erdman S E, Restaino C, Gurish M F, Friend D S, Gounari F, Lee D M, Zhang G, Glickman J N, Shin K, Rao V P, Poutahidis T, Weissleder R, McNagny K M, Khazaie K. Mast cells are an essential hematopoietic component for polyp development. *Proc Natl Acad Sci USA.* 2007; 104:19977-19982
26. Hossain F, Al-Khami A A, Wyczechowska D, Hernandez C, Zheng L, Reiss K, Valle L D, Trillo-Tinoco J, Maj T, Zou W, Rodriguez P C, Ochoa A C. Inhibition of fatty acid oxidation modulates immunosuppressive functions of myeloid-derived suppressor cells and enhances cancer therapies. *Cancer Immunol Res.* 2015; 3:1236-1247
27. Rosado M M, Bennici E, Novelli F, Pioli C. Beyond DNA repair, the immunological role of parp-1 and its siblings. *Immunology.* 2013; 139:428-437
28. Aldinucci A, Gerlini G, Fossati S, Cipriani G, Ballerini C, Biagioli T, Pimpinelli N, Borgognoni L, Massacesi L, Moroni F, Chiarugi A. A key role for poly(adp-ribose) polymerase-1 activity during human dendritic cell maturation. *J Immunol.* 2007; 179:305-312
29. Kim H, Naura A S, Errami Y, Ju J, Boulares A H. Cordycepin blocks lung injury-associated inflammation and promotes brca1-deficient breast cancer cell killing by effectively inhibiting parp. *Mol Med.* 2011
30. Zerfaoui M, Naura A S, Errami Y, Hans C P, Rezk B M, Park J, Elsegeiny W, Kim H, Lord K, Kim J G, Boulares A H. Effects of parp-1 deficiency on airway inflammatory cell recruitment in response to 1 ps or tnf: Differential effects on cxcr2 ligands and duffy antigen receptor for chemokines. *J Leukoc Biol.* 2009; 86:1385-1392
31. Highfill S L, Cui Y, Giles A J, Smith J P, Zhang H, Morse E, Kaplan R N, Mackall C L. Disruption of cxcr2-mediated mdsc tumor trafficking enhances anti-pd1 efficacy. *Science translational medicine.* 2014; 6:237ra267
32. Al-Khami A A, Rodriguez P C, Ochoa A C. Energy metabolic pathways control the fate and function of myeloid immune cells. *J Leukoc Biol.* 2017; 102:369-380
33. Fearnhead N S B M, Bodmer W F. The abc of apc. *Human Molecular Genetics.* 2001; 10:721-733
34. Powell S M. Apc mutations occur early during colorectal tumorigenesis. *Nature.* 1992; 359
35. Kinzler K W. Lessons from hereditary colorectal cancer. *Cell.* 1996; 87:159-170
36. Fahs S A, Hille M T, Shi Q, Weiler H, Montgomery R R. A conditional knockout mouse model reveals endothelial cells as the principal and possibly exclusive source of plasma factor viii. *Blood.* 2014; 123:3706-3713
37. Schlaeger T M, Bartunkova S, Lawitts J A, Teichmann G, Risau W, Deutsch U, Sato T N. Uniform vascular-endothelial-cell-specific gene expression in both embryonic and adult transgenic mice. *Proc Natl Acad Sci USA.* 1997; 94:3058-3063
38. Thevenot P T, Sierra R A, Raber P L, Al-Khami A A, Trillo-Tinoco J, Zarreii P, Ochoa A C, Cui Y, Del Valle L, Rodriguez P C. The stress-response sensor chop regulates the function and accumulation of myeloid-derived suppressor cells in tumors. *Immunity.* 2014; 41:389-401
39. Lee J M, Cimino-Mathews A, Peer C J, Zimmer A, Lipkowitz S, Annunziata C M, Cao L, Harrell M I, Swisher E M, Houston N, Botesteanu D A, Taube J M, Thompson E, Ogurtsova A, Xu H, Nguyen J, Ho T W, Figg W D, Kohn E C. Safety and clinical activity of the programmed death-ligand 1 inhibitor durvalumab in combination with poly (adp-ribose) polymerase inhibitor olaparib or vascular endothelial growth factor receptor 1-3 inhibitor cediranib in women's cancers: A dose-escalation, phase i study. *J Clin Oncol.* 2017; 35:2193-2202
40. Jiao S, Xia W, Yamaguchi H, Wei Y, Chen M K, Hsu J M, Hsu J L, Yu W H, Du Y, Lee H H, Li C W, Chou C K, Lim S O, Chang S S, Litton J, Arun B, Hortobagyi G N, Hung M C. Parp inhibitor upregulates pd-11 expression and enhances cancer-associated immunosuppression. *Clin Cancer Res.* 2017; 23:3711-3720

Example 4

Use of Low Doses of PARP Inhibitors as Adjuvant Therapy for Immunotherapeutic Approaches and Treatment Strategies that do not Target DNA Repair/Damage Mechanisms PARP inhibitors such as olaparib (LYNPARZA™) and others (under clinical trials) are used to target cancer cells with deficiencies in DNA repair enzymes (e.g. BRCA mutations) with a goal to achieve synthetic lethality (specific death of cancer cells). Our results show that partial PARP inhibition is very effective at reducing cancer-related inflammation and promoting a tumor-suppressive environment by interfering with the tumor promoting activity of MDSCs. Without wishing to be bound by theory, one can use PARP inhibitors at a dose that can be gaged according cancer type and affected patient to achieve a better clinical outcome with immunotherapy approaches or with therapies whose targets do not include DNA repair/damage enzymes.

The PARP inhibitor olaparib (LYNPARZA™) is currently being used as an oral treatment for women with BRCA-mutated advanced ovarian cancer; other PARP inhibitors are under clinical trials for other cancers with DNA repair deficiency. As described herein, PARP inhibitors, at low doses, can be used to increase the efficacy of immunotherapy approaches and other approaches that do not target DNA repair/damage enzymes. See FIG. 31, for example. Thus PARP inhibitors can be used for the treatment of a variety of cancers that can benefit from immunotherapy.

The current concept in the use of PARP inhibitors is to achieve maximal inhibition of the enzyme (PARP) with synthetic lethality (i.e. death of mutated cancer cells) as the ultimate goal 1. Embodiments as described herein enhance the immune system in such a way to improve the efficacy of immunotherapy or approaches that do not target DNA repair/damage enzymes in fighting cancer. An additional but important aspect with this approach is that low doses of the drugs may lead to fewer side effects.

Example 5

Metronomic Therapy Targeting Myeloid-Derived Suppressor Cells with the PARP Inhibitor Olaparib Enhances Anti-PD1 Immunotherapy in Colon Cancer Focusing on the maximum-tolerated-dose of PARP inhibitors (PARPi) detracts from reaping the benefits of targeting DNA repair-independent aspects of PARP with lower drug doses. Here, we show that partial PARP-1 inhibition via gene heterozygosity or a moderate olaparib dose protected against colitis- or $APC^{Min}$-mediated intestinal tumorigenesis, while extensive inhibition via gene knockout or a high olaparib dose was ineffective despite anti-inflammatory effects and promotion of a tumor-suppressive microenvironment. A sub-IC50 metronomic dose of olaparib was sufficient to block tumorigenesis in syngeneic colon cancer models by modulating the T-cell suppressive function, but not intratumoral migration, of myeloid-derived suppressor cells (MDSCs) via a reduction of arginase-1/iNOS/COX-2 expression but independently of PARP-1-trapping on chromatin. A metronomic olaparib dose exhibited remarkable synergy with anti-PD1-based immunotherapy in mice. These results indicate that targeting MDSCs with metronomic PARPi doses enhances efficacy of immunotherapies, validating a paradigm-shift that expands the utility of PARPi in anti-cancer therapy.

Introduction

PARP inhibitors (PARPi) are emerging as a promising therapy for ovarian and breast cancers as well as potentially for a few other cancers that may be driven by deficiencies in non-PARP-associated DNA repair (1). Interestingly, a number of clinical trials demonstrated the efficacy of PARPi in the treatment of other cancers with no obvious mutations in the BRCA1 gene (2). These observations clearly suggest a potential for this therapeutic strategy to be utilized in non-BRCA1 mutated cancers. Unfortunately, many of these trials fail to advance to actual therapies. Olaparib was tested in phase I (3) and phase II (4) clinical trials on patients with advanced colon cancer as a monotherapy or in combination with irinotecan (Camptosar) with disappointing results but with recommendations for more comprehensive studies. Without wishing to be bound by theory, the primary reason for the failure of PARPi in treating non-BRCA1 mutated cancers is the fact that the intricacies of the role of the enzyme in cancer pathogenesis are not fully understood. This idea becomes even more important when considering that the cancer microenvironment is not only influenced by the neoplastic cell but also by structural and cellular components that include immune cells. Important objectives of our laboratory are to unravel unobvious functions of DNA repair enzymes, such as PARP-1, and to validate that these enzymes play critical roles not only in cancer cell-related processes (e.g. DNA repair, cell death, and genomic integrity) but also in inflammatory and immune responses. The function of PARP-1 in cancers may be intimately related to its ability to provide an alternative pathway for cancer cells to survive, especially for those cancers associated with defects in DNA repair; however, the mechanism by which PARP-1 contributes to inflammation and immune responses may be very different.

The role of PARP-1 in DNA repair requires the full activity of the enzyme, as partial inhibition of PARP-1 is not associated with major defects in DNA repair (5). Indeed, PARP-1 heterozygous cells or mice respond similarly to DNA-damaging agents as their wild-type (WT) counterparts (5, 6). Interestingly, we reported that PARP-1 heterozygosity, which reduces PARP-1 by ~50%, or a metronomic dose of PARPi substantially blocked atherosclerosis in high-fat diet-fed $ApoE^{-/-}$ mice and asthma in allergen-exposed mice (7-9). Inhibition of PARP with 3-aminobenzamide, an old-generation weak inhibitor, was shown to provide protection against trinitrobenzene sulfonic acid-induced colitis in rodents and in an interleukin (IL)-10 deficiency-based mouse model of chronic intestinal inflammation (reviewed in (10)), while complete inhibition of PARP-1 by gene knockout enhanced tumorigenesis to azoxymethane-induced colon tumorigenesis (11). In vitro studies from our laboratory revealed that an olaparib concentration that does not affect proliferation of human $CD3^+$ T cells was very effective at reducing expression of Th2-associated genes, while sparing such effects on IFNγ expression (9). Furthermore, while a moderate concentration (1 μM) of olaparib did not induce an increase in the $CD25^+/Foxp3^+$ Treg cell population upon stimulation of $CD4^+$ T-enriched cells with antibodies to CD3/CD28, a higher concentration (5 μM) almost doubled the percentage of these regulatory cells. Altogether, these reports clearly suggest that low-to-moderate doses of PARPi may have completely different effects than those mediated by high doses of the drugs.

One of the hallmarks of tumor progression and resistance to therapy is the recruitment of myeloid-derived cells that suppress cancer cell-killing immune cells. Myeloid-derived suppressor cell (MDSC) recruitment and expansion represent critical events during cancer progression, which can be classified as granulocytic or polymorphonuclear (G- or PMN) or monocytic (M)-MDSCs. While PMN-MDSCs resemble neutrophils, M-MDSCs display more monocytic-like traits (12, 13). These cells provide an advantage to cancer cells, allowing them to evade the immune system (12). MDSCs are specialized in blocking T-cell function by promoting the expansion of Treg cells, depriving T cells of essential amino-acids through expression of arginase (ARG)-1, producing oxidizing molecules (e.g., $ONOO^-$) through the expression of inducible nitric oxide synthase (iNOS), and blocking T-cell recruitment to tumors (12). Therefore, it is clear that interfering with the function and/or recruitment of MDSCs may provide important benefits to strategies targeting cancer cells, representing an attractive strategy to treat not only colon cancer but also many other cancers.

Most current therapeutic strategies rely heavily on the administration of chemotherapeutic agents based on the maximum-tolerated-dose (MTD) paradigm, even when combined with adjuvant therapies; however, such a philosophy misses the potential of metronomic regimens aimed at the same or alternate targets that may be of equal or greater benefit (14, 15). A primary goal of the current study was to compare the effects of partial PARP inhibition by gene heterozygosity or a low-to-moderate dose of olaparib provided in a metronomic manner to complete or extensive inhibition of the enzyme by gene knockout or high-dose olaparib on inflammation-driven or spontaneous colon cancer. We also sought to examine whether the different approaches exert different immune responses to carcinogenesis by focusing primarily on MDSCs and determine whether a metronomic dose of olaparib synergizes with anti-PD1 immunotherapy.

Results

Partial PARP-1 Inhibition is More Efficient than Complete Inhibition at Reducing Chronic Inflammation-Driven Colon Tumorigenesis in Mice Despite an Equal Modulation of Systemic Inflammation PARP-1 gene heterozygosity reduced PARP-1 expression by ~50% compared to that of WT cells (FIG. 32A), which is consistent with our previous report (8) and is known to lead to an equal reduction in enzymatic activity (16). Using a method for colon epithelial cell (CEC) isolation from mice developed by our laboratory, we compared the efficacy of partial PARP-1 inhibition by gene heterozygosity in reducing lipopolysaccharide (LPS)- or tumor necrosis factor (TNF)-α-induced expression of inflammatory genes with that of complete inhibition achieved by gene knockout. FIG. 32B shows that the potent capacity of LPS to induce expression of IL-6, TNF-α, iNOS, intercellular adhesion molecule (ICAM)-1, and vascular cell adhesion molecule (VCAM)-1 in WT CECs was significantly reduced in similarly treated PARP-1$^{+/-}$ and PARP-1$^{-/-}$ CECs. Remarkably, PARP-1 heterozygosity was as effective as knockout at reducing or blocking the expression of the examined genes. In response to TNF-α, PARP-1 heterozygosity was either equally effective or even better than knockout at reducing expression of the adhesion molecules ICAM-1 and VCAM-1, respectively (FIG. 32B). These results demonstrate that complete inhibition of the enzyme is not necessary to achieve maximal blockade of inflammatory responses.

We next examined whether PARP-1 gene dosage exerted similar effects on inflammation-driven colon cancer. To this end, we selected a colon cancer model that is exclusively induced by chronic inflammation via a single administration of the rodent carcinogen azoxymethane (AOM) to mice followed by four cycles of dextran sulfate sodium (DSS) in drinking water. Notably, neither administration of AOM nor DSS was sufficient to induce tumorigenesis (FIG. 32C). The AOM/DSS combination is highly consistent in inducing primarily colon tumors ((17) and FIG. 32D), and this AOM/DSS treatment regimen induced an average of 8-10 tumors in colons of WT mice. AOM/DSS-treated PARP-1$^{-/-}$ mice displayed a significantly (p<0.001) lower tumor burden than similarly treated WT mice, consistent with a recent report by Dorsam et al. (18). Surprisingly, partial PARP-1 inhibition generated by gene heterozygosity was far more effective than gene knockout at reducing the tumor burden (p=0.0063). Overall, the tumors detected in all experimental groups were small (~2 mm in diameter), reaching adenoma or adenocarcinoma status (>1 mm) only in AOM/DSS-treated WT and PARP-1$^{-/-}$ mice. Examination of tissue sections prepared from the colons of AOM/DSS-treated WT mice showed rather typical colon tumors with marked hyperplasia and dysplasia and development of large aberrant crypt foci (ACF), which were not drastically different from those of similarly treated PARP-1$^{-/-}$ mice (FIG. 32D). Interestingly, the tumors from AOM/DSS-treated PARP-1$^{+/-}$ mice were markedly smaller and consisted primarily of large ACFs. High immunoreactivity to PCNA, a marker of cell proliferation, was detected in tumors of AOM/DSS-treated WT and PARP-1$^{-/-}$ mice (FIG. 32E), and this immunoreactivity was much lower in tumors of treated PARP-1$^{+/-}$ mice (p<0.001; FIG. 38). AOM/DSS treatment-induced damage to the colonic mucosa in PARP-1$^{+/-}$ and PARP-1$^{-/-}$ mice was not as prevalent as that observed in similarly treated WT mice (FIG. 32F). It is noteworthy that the mucosa of AOM/DSS-treated PARP-1$^{+/-}$ or PARP-1$^{-/-}$ mice showed some disorganization and injury, but the colonic crypts were relatively intact or appear to be in the process of recovery. These results are consistent with those reported by Larmonier et al. (19) in which PARP-1$^{-/-}$ mice were found to be resistant to DSS-based colitis induction.

Given the clinical relevance of our studies, we then sought to examine whether pharmacological inhibition of PARP with olaparib prevents or reduces colon tumorigenesis in the AOM/DSS mouse model of colon cancer. It is noteworthy that olaparib inhibits both PARP-1 and PARP-2, and therefore, specificity to PARP-1 in our studies is always based on the common results between those attained with the drug and those attained in PARP-1$^{+/-}$ or PARP-1$^{-/-}$ mice. To conduct this study, we elected to use a moderate olaparib dose of 5 mg/kg to be consistent with our previous studies in addition to an olaparib dose that is five times higher (25 mg/kg), which is a beginning dose in most published preclinical cancer studies (10). The drug was administered twice weekly for the duration of the protocol. FIG. 32G shows that treatment with olaparib at either dose significantly reduced the tumor burden compared to treatment with the vehicle. When colonic mucosa was examined for evidence of colitis in the two groups, olaparib treatment provided a notable protection against AOM/DSS treatment-induced effects (FIG. 32H). These results are in agreement with those attained using AOM/DSS-treated PARP-1$^{+/-}$ and PARP-1$^{-/-}$ mice, indicating that PARP inhibition, partially or completely, is effective at blocking colitis. As stated above, the AOM/DSS colon cancer model is driven primarily by chronic inflammation; thus, we next assessed mice sera for inflammatory factors TNF-α, IL-6, and MCP-1, which are highly relevant to human colon carcinogenesis. FIG. 32I shows that all forms of PARP-1 inhibition were associated with a marked reduction in the levels of TNF-α and MCP-1 with a moderate effect on IL-6 levels. These results indicate that the role of PARP-1 in colon inflammation may, in part, constitute the underlying mechanism by which the enzyme participates in the pathogenesis of colon cancer.

Partial Inhibition of PARP-1 by Gene Heterozygosity or a Moderate Dose of Olaparib Protects Against $APC^{Min}$-Induced Tumor Burden in Mice while Complete Inhibition by Gene Knockout Aggravates Tumor Burden If chronic inflammation is the sole mechanism by which PARP-1 participates in colon tumorigenesis, then the ability to severely block inflammation upon inhibition of the enzyme, pharmacologically or genetically, should almost entirely alleviate the tumor burden. According to the above data, however, this is not the case. Therefore, we next examined the role of PARP-1 gene dosage on colon tumorigenesis using the $APC^{Min/+}$ mouse model, which spontaneously develops intestinal tumors but does not exclusively rely on inflammation. In general, $APC^{Min/+}$ mice have a rather short lifespan and often die not only as a result of tumor burden but also due to development of severe anemia, substantial cachexia, and/or intestinal intussusceptions. To this end, C57BL/6 PARP-1$^{+/-}$ and PARP-1$^{-/-}$ mice were generated in the $APC^{Min/+}$ background (FIG. 39). PARP-1 heterozygosity provided remarkable protection against tumor development (FIG. 33A). Surprisingly, PARP-1 knockout not only failed to provide any protection but actually significantly aggravated the tumor burden. In addition, PARP-1 heterozygosity completely blocked the generation of large tumors (>4 mm in diameter) with a significant concomitant decrease in small and medium-sized tumors (FIG. 33B). Conversely, PARP-1 knockout promoted an increase in the number of small tumors. PCNA immunoreactivity in tumors of $APC^{Min/+}$ mice did not differ from that observed in $APC^{Min/+}$ PARP-1-/- mice (FIG. 33C), but the difference between these two groups and that of PARP-1$^{+/-}$ mice was highly significant (data not shown). Paradoxically, intratumoral inflammation as assessed by immunoreactivity to COX-2 (FIG. 33D) was equally reduced in tumors of PARP-1$^{+/-}$ and PARP-1$^{-/-}$ mice. We next examined the effect of administration of a moderate (5 mg/kg) or a high (25 mg/kg) dose of olaparib on $APC^{Min}$-driven tumorigenesis in mice starting at 6 week of age. PARP inhibition from the moderate dose of olaparib provided good protection against tumor development; however, although the higher dose resulted in great variability in response, overall, it provided no significant protection with respect to tumor burden (FIG. 33E). In fact, some of the mice treated with the higher olaparib dose showed a greater tumor burden than that of the vehicle group.

Weight loss or cachexia is often observed in patients with colon cancer and is a persistent trait in the $APC^{Min/+}$ mouse model of colon cancer. Indeed, $APC^{Min/+}$ mice weighed ~15-25% less than WT mice (FIG. 33F), consistent with published reports (20). PARP-1 heterozygosity completely prevented cachexia. Surprisingly, while PARP-1 knockout aggravated the tumor burden in $APC^{Min/+}$ mice, this genotype not only failed to aggravate the weight loss observed in these mice but also actually prevented this weight loss to a small but statistically significant level. While the moderate dose of olaparib protected against cachexia in $APC^{Min/+}$ mice, the high dose of the drug did not. Although splenomegaly is not a common feature in human colon cancer, it is a persistent trait of $APC^{Min/+}$ mice and other mouse tumor models. FIG. 33G shows that, as expected, $APC^{Min/+}$ mice displayed larger spleens that were often as much as 6× larger than that of a matched age WT mice. Interestingly, all forms of PARP-1 inhibition reduced the size of spleens similarly, although control spleen sizes were not reached. Systemic inflammation is also a component of $APC^{Min}$-driven intestinal carcinogenesis. All forms of PARP-1 inhibition significantly reduced MCP-1 to levels comparable to those detected in sera of WT mice (FIG. 33H) but had more moderate effects on TNF-α levels. As for IL-6, only PARP-1 heterozygosity promoted a slight but statistically significant reduction in the cytokine. These results indicate that the protective effects of PARP-1 heterozygosity or the moderate dose of olaparib is not strictly associated with a reduction in systemic inflammation but is related, rather, to host response to such inflammation and tumor development.

A Metronomic Dose of Olaparib or PARP-1 Gene Heterozygosity are Sufficient to Promote a Tumor-Suppressive Environment in the MC-38 Cell-Based Syngeneic Colon Cancer Mouse Model It is noteworthy that the host immune response is recognized as an important determinant of carcinogenesis in general and of colon cancer in particular (21). Given the above results, it became imperative to determine whether PARP-1 plays a role in the host response to tumor development. To this end, we took advantage of a syngeneic model based on the colon adenocarcinoma cell line MC-38, which was derived from a C57BL/6 mouse. MC-38 cells express abundant levels of PARP-1 protein (FIG. 34A) and are expected to behave as WT cells. Engraftment of MC-38 cells into the flanks of WT mice led to sizable solid tumors (FIG. 34B), while engraftment into either PARP-1 heterozygous or knockout mice significantly reduced the size of the tumors at day 22. The tumors generated in PARP-1$^{+/-}$ and PARP-1$^{-/-}$ mice displayed little inflammation compared to the WT counterparts as assessed by ICAM-1 immunoreactivity (FIG. 34C). This reduction in tumor burden was accompanied by a maintenance of normal size spleens (FIG. 34D).

Because a moderate dose of 5 mg/kg olaparib provided superior protection compared to a high dose in the $APC^{Min/+}$ mouse model, we elected to continue using the moderate dose but also examined the effects of a 25-fold lower metronomic dose (i.e., 0.2 mg/kg). To this end, WT mice were engrafted with MC-38 cells, and when tumors were palpable, mice were administered either 0.2 or 5 mg/kg olaparib once every 2 days. Surprisingly, although the moderate dose of olaparib provided a significant reduction in the size of MC-38 cell-based tumors, the lower dose of the drug was more effective at reducing the tumor burden (FIG. 34E). An evaluation of intratumoral ICAM-1 immunoreactivity as a surrogate for inflammation revealed that both doses promoted a reduction in inflammation (FIG. 34F). Systemic inflammation, as assessed by the levels of TNF-α, IL-6, and MCP-1 in sera of animals, was moderately reduced by both doses of olaparib, despite the different outcomes on the tumor burden (FIG. 34G). Examination of protein extracts prepared from tumors from the different experimental groups showed that all forms of PARP inhibition tended to increase the levels of active caspase-3 and -7 (FIG. 34H), indicating higher levels of cell death within those tumors. Overall, these results indicate that a low dose of olaparib can exert a superior anti-tumor effect compared to a high dose, despite the relatively similar reduction in intratumoral and systemic inflammation.

PARP-1 Plays a Key Role in MDSC Function, and Partial Inhibition of PARP-1 by Gene Heterozygosity or Low-to-Moderate Doses of Olaparib are Sufficient to Block the Suppressive Activity of these Cells Pro-tumor immune cells, such as MDSCs, are important players in the regulation of the tumor microenvironment via suppression of the host responses to tumors and promotion of tumorigenesis (12). We therefore examined whether partial PARP inhibition by olaparib treatment or gene heterozygosity affected this cell population in MC-38 cell-generated tumors. The low dose (0.2 mg/kg) of olaparib did not significantly affect the percentages of CD11b$^+$/Gr1$^+$ MDSCs or their numbers in the examined tumors (FIGS. 35A &B). The moderate dose (5 mg/kg) of olaparib, however, significantly increased the numbers and percentages of M-MDSCs, albeit by a relatively small amount (FIG. 35C). PARP-1 heterozygosity, on the other hand, was associated with a minor but statistically significant increase in the percentage of M-MDSCs with a concomitant decrease in PMN-MDSCs; however, the overall cell numbers were comparable to those detected in tumors generated in WT mice (FIG. 35C). Only the low dose of olaparib increased CD3$^+$ T cells, and most of these were CD8$^+$ T cells (FIG. 35D). The intratumoral distribution of MDSCs (Gr1$^+$) and CD8$^+$ cells in the different experimental groups was corroborated using immunohistochemistry with antibodies to murine Gr1 or CD8 by a pathologist (Dr. L. DelValle), who was blinded to the different groups (FIG. 35E). Interestingly, in the spleens, only the moderate dose of olaparib promoted a substantial decrease in overall CD3$^+$ T cells and a concomitant decrease in CD8$^+$ T cells (FIG. 35F), suggesting immune suppressive effects.

The lack of a major effect of PARP inhibition on MDSC populations indicates that the migration of these cells into the tumors was not drastically affected by the different forms of PARP-1 inhibition to sufficiently explain the reduction in tumor burden. Without wishing to be bound by theory, PARP-1 may influence the function rather than the phenotype of MDSCs. To test this, MDSCs were isolated from MC-38 cell-generated tumors using CD11b positive selection and then co-cultured with CFSC-labeled anti-CD3/CD28-activated WT T cells without the addition of olaparib. As expected, MDSCs isolated from tumors of WT mice were effective at suppressing T-cell proliferation upon stimulation (FIG. 35G). MDSCs derived from tumors of olaparib-treated mice exhibited a reduced capacity to suppress T-cell proliferation, and cells from mice treated with the moderate dose displayed a more pronounced effect. Remarkably, MDSCs derived from tumors of PARP-1$^{+/-}$ mice completely failed to suppress the proliferation of WT T cells. MDSCs derived from tumors of PARP-1$^{-/-}$ mice also failed to suppress T-cell proliferation in vitro (FIG. 40). Altogether, these results suggest that PARP-1 plays a critical role in MDSC function and that these cells are very sensitive to PARP-1 inhibition either with a low dose of olaparib or PARP-1 heterozygosity.

A Sub-IC50 Concentration of Olaparib is Sufficient to Reduce MDSC Suppressive Function In Vitro, in Part, by Blocking the Expression of ARG-1, iNOS, and COX2, and the Adoptive Transfer of WT MDSCs Abrogates the Protective Effects of PARP-1 Heterozygosity Against the Tumor Burden We next explored the potential mechanism(s) by which even a low dose of a PARPi reduces the function of MDSCs. To this end, bone marrow cells collected from WT or PARP-1$^{+/-}$ mice were incubated with a cocktail containing GM-CSF, G-CSF, and IL-6. After 24 hours in culture, some WT cells were treated once with increasing concentrations of olaparib or 0.01% DMSO for an additional 3 days. We used 4 nM olaparib as a low-concentration dose, as this is below the IC50 for the drug; 0.1 and 5 µM olaparib were used as the moderate and high concentrations, respectively. After 4 days in culture, cell phenotypes were determined by FACS. The viability of MDSCs was not affected by any condition (FIG. 41A). PARP-1 inhibition by a low or moderate concentration of olaparib exerted no effect on the percentage of CD11b$^+$/Gr1$^+$ MDSCs generated during the differentiation process (FIG. 36A). Interestingly, the high concentration of the drug (5 µM) increased the number of the examined MDSCs. PARP-1 heterozygosity did not increase the percentage of MDSCs, but similarly to the high olaparib concentration, PARP-1 knockout significantly increased the MDSC population (FIG. 41B). It is noteworthy that the prevalence of MDSCs in tumors of APC$^{Min/+}$ PARP-1$^{-/-}$ mice was also higher than that in tumors of APC$^{Min/+}$ mice (FIG. 42). Gr1$^+$-MDSCs from the different experimental groups were co-cultured at day 4 with CFSE-labeled WT CD3$^+$ T cells. Proliferation of T cells was assessed 3 days later by FACS. The co-culture assay was conducted in the absence of olaparib. WT MDSCs were efficient at suppressing the proliferation of T cells (FIG. 36B). Such suppressive activity was significantly reduced even after treatment with the low olaparib concentration of 4 nM. The moderate and high concentrations blocked the function of MDSCs completely, and this result was mirrored by PARP-1 heterozygosity. The low concentration of olaparib exerted no effect on proliferation of T cells (FIG. 36C); however, despite the inhibition of the moderate and high concentrations of olaparib of MDSC function, such concentrations exerted significant effects on T-cell proliferation (FIG. 36C), consistent with our previous studies using primary human T cells (9). To determine whether the effects of PARP inhibition on MDSCs were, at least in part, responsible for the effects on tumorigenesis, we adoptively transferred bone marrow-derived in vitro-differentiated WT MDSCs into MC-38 cell-based tumors in PARP-1$^{+/-}$ mice. Since a pharmacological approach is not appropriate to address the question, we used PARP-1$^{+/-}$ mice as a model for partial PARP inhibition. FIG. 36D shows that adoptive transfer of MDSCs into WT mice exerted no effect on the size of the tumors, and this result is consistent with the report by Sceneay et al.(22). Administration of WT MDSCs into tumors of PARP-1$^{+/-}$ mice, however, temporally abrogated the effects of PARP-1 heterozygosity, resulting in increased tumor size. Interestingly, the tumor tended to shrink to the level observed in control PARP-1$^{+/-}$ mice a few days after the increase, and a second administration of MDSCs reversed the tumor size to that observed in tumors of WT mice.

In an effort to determine the mechanism(s) by which PARP-1 regulates MDSC function, we next explored the effect of PARP-1 inhibition on the expression of key factors, such as iNOS, ARG-1, and COX2, which are known to play a major role in the ability of MDSCs to suppress T-cell proliferation (12, 23). We conducted a time course and followed the expression of these factors during the differentiation process; all treatments with olaparib were performed once, starting 24 hours after plating. An expected gradual increase in ARG-1, iNOS, and COX2 upon stimulation with GM-CSF/G-CSF/IL-6 was observed (FIG. 36E). MDSCs appeared to be extremely sensitive to treatment with olaparib, as the 4 nM concentration was sufficient to prevent the increase in ARG-1, iNOS, and COX2 observed in control cells; however, the pattern of the effect on ARG-1 was different from that of iNOS and COX2. ARG-1 expression was not affected during the first 24 h of treatment with either concentration of olaparib. The downregulation of ARG-1 occurred beginning at 2 days of treatment. The decrease in the aforementioned factors was associated with a reduction in p53 phosphorylation. Surprisingly, only the low concentration of olaparib increased the overall levels of STAT3 with a concomitant increase in its phosphorylated α and β forms. The inhibitory effects of the low and high concentrations of olaparib on ARG-1 and iNOS were also observed following stimulation of MDSCs by cancer cells through a co-culture with MC-38 cells (FIG. 36F). Similar results were observed when the 3LL lung carcinoma cell line was used as the stimulus (FIG. 36G). The specificity of the relationship between ARG-1 and PARP-1 was verified using MDSCs derived from bone marrow of PARP-1$^{+/-}$ mice (FIG. 36G). Furthermore, the addition of olaparib to PARP-1$^{+/-}$ MDSCs co-cultured with 3LL cells did not dramatically change the effect on ARG-1 expression. Overall, the above results demonstrate that PARP-1 plays a critical role in MDSC function, that these cells are highly sensitive to inhibition of the enzyme, and that this effect is key to the protective effects of low doses of olaparib against tumor formation.

The Modulatory Effect of Low-Dose Olaparib on MDSC Function is Independent of PARP-1 Trapping to Chromatin The principal mechanism by which PARPi achieve cytotoxic effects on BRCA-mutant cancer cells is by trapping PARP-1 to breaks in the chromatin induced by exposure to DNA-damaging agents (2). Thus, we determined whether the effect of olaparib on MDSC function is related to this process. MDSCs were treated with different concentrations of olaparib for 12 h, and then nuclear and chromatin fractions were isolated. PARP-1 remained primarily in the nuclear fraction after treatment with the different concentrations of olaparib (FIG. 36H). FIG. 36I shows PARP-1 trapping on DNA chromatin following treatment of Jurkat T cells with the DNA-damaging agent VP-16. The low concentration of olaparib promoted little to no trapping of PARP-1 on the chromatin, while the high concentration of olaparib promoted substantial trapping, and these findings reflected the extent of DNA damage as indicated by the level of phosphorylated H2AX (γH2AX).

A Metronomic Dose of Olaparib Synergizes with Anti-PD1 Therapy to Eradicate MC-38 Cell-Based Tumors in Mice It is important to acknowledge the unlikely scenario in which low doses of PARPi are adopted in the clinic based on the concern of potentially subjecting patients to unacceptable risks. However, without wishing to be bound by theory, this strategy may be ideal for the enhancement of existing anti-cancer immunotherapies, such as checkpoint blockers (24). We, thus, examined the efficacy of a metronomic dose (0.2 mg/kg on alternate days) in enhancing the anti-tumor effect of anti-PD-1 therapy (100 μg/mouse administered every 4 days) in the MC-38 cell-based model. As expected, anti-PD1 and olaparib, individually, significantly reduced the progression of MC-38 tumors in WT mice (FIG. 37A). Interestingly, the efficacy of the low dose of olaparib in reducing tumor size was comparable to that promoted by anti-PD1 therapy. Remarkably, however, the combination was substantially more effective at blocking tumor progression. In fact, some mice displayed complete tumor remission. The efficacy of a low dose of olaparib and anti-PD-1 therapy was reproduced using MC-38 cells transfected with a GFP- and luciferase-expressing plasmid. Tumors in mice from the different experimental groups were examined using biophotonic imaging (FIG. 37B), and the luciferase activity signal in the different tumors was determined (FIG. 37C), further indicating the significant synergy between the metronomic dose of olaparib and anti-PD1 therapy. Specificity to PARP-1 was verified with the same approach using PARP-1$^{+/-}$ mice (FIG. 37D). All forms of treatment either partially or completely prevented the tumor-associated increase in spleen size (FIG. 37E). Similarly, all forms of treatment reduced systemic inflammation, although anti-PD-1 or its combination with olaparib exerted a more pronounced reduction in MCP-1 and IL-6 (FIG. 37F). Given the eradication of tumors by the combination of olaparib and anti-PD1, only a few tumors were large enough to be used for protein extraction followed by immunoblot analysis. While both the low dose of PARPi and anti-PD1 immunotherapy induced an increase in PD-L1 in tumors, the combination therapy was associated with a decrease in PD-L1 (FIG. 37G). The overall activation of caspases-3, -7, -8, and -9 was higher in tumors isolated from animals treated with olaparib, anti-PD1 therapy, or the combination of both treatments. There was a concomitant increase in γH2AX, which may be due to DNA breaks generated upon stimulation of the caspase-activated endonuclease. An increase in p21/Waf1 in these groups indicated a simultaneous increase in cell cycle arrest (FIG. 37G, lower panels). Surprisingly, all forms of treatment induced a moderate increase in PARP activation, as assessed by immunoblot analysis with antibodies to poly(ADP-ribosyl)ated proteins.

Finally, the strong synergy between a metronomic dose of olaparib and anti-PD1 therapy required verification in a different colon cancer model. Therefore, we used the more aggressive colon carcinoma cell line CT-26, which has a BALB/c genetic background. Although a low dose of olaparib promoted a statistically significant reduction in tumor size in BALB/c mice, especially early during the protocol, the overall effect was marginal (FIG. 37H). The anti-PD1 therapy also proved efficient in this model but not to the extent of that observed in the MC-38 cell-based model. The effect of the combination of treatments, however, was substantially better at reducing the tumor burden in this model, revealing a significant synergy between two therapies. These results were mirrored by effects on spleen size (FIG. 37I). The tumors in this model were sufficiently large to determine that anti-PD1 treatment promoted a slight, but statistically significant, increase in the percentage of MDSCs, which was reduced to control levels by olaparib treatment (FIG. 43). Overall, these results indicate a significant synergy between a low dose of Olaparib and anti-PD1 therapy.

Discussion

The status of anti-cancer therapy is undoubtedly unsatisfactory, and much remains to be done to increase the efficacy of current strategies in order to provide additional viable options to affected individuals to improve their quality of life. The results of our studies unravel an unexpected role for PARP-1 in regulating MDSC function, providing a paradigm-shifting concept that may be applied not only to colon cancer but also to all conditions that reap benefits from immunotherapy. Our data demonstrate that targeting MDSC function with a low dose of olaparib provides an impressive effect on tumor growth alone, and more importantly, this olaparib treatment synergizes with anti-PD1 immunotherapy. The superiority of partial PARP-1 inhibition compared to extensive inhibition was demonstrated in several models, increasing our confidence in the relevance to human disease. The concept is that modulation of the suppressive function of MDSCs within the tumor microenvironment using metronomic doses of PARPi provides an advantage to the immune system to attack the tumor and to prevent its progression or promote its regression. The addition of immunotherapy, such as anti-PD1, ensures the maintenance of a robust anti-tumor response.

The ultimate goal of high doses of PARPi-based therapy is the promotion of synthetic lethality in BRCA-mutated cancer cells (1). Although this concept is appealing and is theoretically expected to affect only the cancer cell, the reality is that such therapy also affects normal healthy cells. Indeed, moderate and high doses of PARPi have been shown to be immunosuppressive ((1, 2), see FIG. 35D). While such effects may be counterintuitive when checkpoint blockers are considered, results of some clinical trials using a combination of high doses of PARPi and immunotherapy to target lung cancer with a high mutation rate were promising (reviewed in (1)); however, the long-term beneficial or detrimental effects remain to be determined. In a very recent single-arm phase II clinical trial, the combination of durvalumab, an anti-PD1 antibody, plus a maximal dose of olaparib (600 mg/daily) did not meet the primary set endpoint in patients with relapsed small cell lung cancer (25). An important observation from this study that needs to be mentioned is that 60% of patients exhibited significant lymphopenia and 50% displayed leucopenia indicating important immunosuppression. PARPi therapy aims at increasing the mutation rate of cancer cells to promote the generation of a higher number of neoantigens in such a way that immunotherapy becomes more effective; yet, it may not selectively achieve the intended goal, as it is also expected to increase mutations in genes that may elevate tumor progression, resistance to therapies, and recurrence. Despite the recent application of PARPi-based therapy, there are concerns regarding resistance to PARPi (1). However, without wishing to be bound by theory, the use of metronomic doses of PARPi is unlikely to cause similar side effects, as the outcome of such treatment may be limited to a portion of the immune cell populations and may not exert any direct DNA repair-associated alterations in the cancer cell. Further validation of the efficacy of metronomic doses of PARPi in combination with immunotherapy can be attained through clinical testing. The metronomic chemotherapy concept is not very new; however, its adoption in the clinic has been limited (14, 15). With the development of precision medicine, interest in this concept is becoming more apparent. Dalgleish and Stern (15), in a very elegant and objective examination of the status and potential of this concept in current anti-cancer therapies, propose that investigators focus attention on the notion that "less can be more", perhaps not only enhancing anti-tumor therapy efficacy but also sparing patients from many of the life quality-reducing side effects of the therapies.

Migration of MDSCs to tumors is critical both for their activation and their suppressive activity against T cells. In several studies, we demonstrated that PARP inhibition either genetically or pharmacologically via moderate doses of PARPi affects the migration of either Th1 or Th2 inflammatory cells into sites of injury (9). We attributed this effect to a reduction in several chemokines, including MCP-1, and adhesion molecules, such as ICAM-1. It is rather puzzling that PARP inhibition did not affect the migration of MDSCs into tumors, despite the clear reduction in systemic MCP-1 and intratumoral ICAM-1. These results suggest that MDSCs do not require large amounts of the chemokines or adhesion molecules for intratumoral migration.

What is clear from our results is that MDSC function is highly sensitive to PARP inhibition and that such effect is not associated with PARP-1 trapping on the chromatin. A sub-IC50 concentration and dose of olaparib were capable of reducing the suppressive capacity of MDSCs in vitro and ex vivo, respectively. The low concentration of the drug did not promote PARP-1 trapping on the chromatin, suggesting that the mechanism by which PARP inhibition reduces MDSC function is unrelated to its role in DNA repair. In addition, the effect of PARP inhibition on MDSC function also appears to be durable, as MDSCs isolated from tumors of olaparib-treated mice remained, at least partially, incapable of regaining their suppressive function, despite the fact that the assay was performed in the complete absence of the drug ex vivo. Equivalent concentrations of olaparib or other PARPi do not exert any major effects on cancer cells (10). Interestingly, the primary mechanism by which PARP inhibition modulates the suppressive activity of MDSC appears to be via reduction of the expression of factors necessary for the function of these cells. An effect by PARP inhibition on iNOS and COX2 may be predictable because these proteins can be regulated by several factors, including NF-κB and STAT6, that PARP-1 influences. However, the mechanism by which PARP-1 inhibition reduces ARG-1 levels appears to be different, as the effects were not evident until after 24 h of treatment. The levels of ARG-1 were always low in PARP-1$^{+/-}$ MDSCs, suggesting that long-term inhibition of PARP is necessary for ARG-1 downregulation. As stated above, olaparib inhibits both PARP-1 and PARP-2. The addition of the drug to PARP-1$^{+/-}$ MDSCs did not change the effect on ARG-1 expression suggesting a potentially specific relationship between ARG-1 and PARP-1 but not PARP-2. Efforts to identify the transcription factor(s) that is targeted by PARP inhibition both in terms of expression levels and posttranslational modifications provided no concrete conclusions, as many of relevant transcription factors were not affected during the process of MDSC differentiation in vitro. A more comprehensive investigation is required to decipher the exact signaling mechanism by which PARP-1 influences MDSC function. Nevertheless, our current findings are certainly translatable and can serve as a platform for immediate clinical trials.

Currently, there are several clinical trials examining the combination of PARPi and checkpoint blockers. The primary goals of these trials are to test whether checkpoint blockers enhance efficacy of PARPi in a variety of cancers or to explore the potential of PARPi in increasing the rate of mutations to promote a greater number of neoantigens. The doses used in these trials are not different from those used as a monotherapy, and few trials propose dose-escalation strategies. Embodiments described in the present work are quite different and does not target the cancer cell. Instead, embodiments herein target MDSCs. Without wishing to be bound by theory, the present invention will not only expand the utility of FDA-approved PARPi but will also revive interest in PARPi with a low-to-moderate capacity to trap PARP-1 on damaged chromatin. Such expansion will undoubtedly increase the options available to cancer patients and may have immediate clinical benefits. Very recently, Jiao et al. (26) reported that olaparib, at a dose of 50 mg/kg daily, enhances anti-PD1 immunotherapy in an allograft breast cancer mouse model, although the PARPi used in the study promoted immunosuppression with a concomitant upregulation of PD-L1 expression. Such effects appeared to be independent of the immune system, since it manifested in a breast cancer xenograft model. In our experimental system, a low dose of PARPi also induced an increase in PD-L1 in tumors, an effect that is not different from that induced by anti-PD1 immunotherapy. Interestingly, combination therapy was associated with a decrease in PD-L1. Although it is difficult to explain this result, it is possible that the lower levels of PD-L1 are associated with the predicted increase in cell killing and proteasomal activity that is known to regulate the fate of the protein. Unlike in whole tumors, the low and high concentrations of olaparib exerted opposing effects on MC-38 cell-stimulated PD-L1 expression in MDSCs (FIG. 44), and notably, the MC-38 cells, in our hands, did not express PD-L1 in either the absence or presence of olaparib. Again, high concentrations of PARPi have been shown to be immunosuppressive, and such an effect can be detrimental as a robust immune system to attack tumor cells is needed for immunotherapy success. Furthermore, the use of high doses of PARPi will undoubtedly lead to undesired side effects and potential resistance to the drugs. More problematic is the fact that these doses will ultimately promote genomic instability of cancer cells as well as normal cells, ultimately leading to additional complications. This notion is supported by our results in the $APC^{Min/+}$ mouse model, in which complete inhibition of PARP-1 by gene knockout actually aggravated the tumor burden instead of providing protection as PARP-1 heterozygosity. We reported this dichotomy several years ago in a conference report (*Paradoxical roles of PARP-1 in colon inflammation and tumorigenesis; FASEB J. Vol.* 29, *No.* 1_*supplement April* 2015) and was supported by a recent study that reported that complete inhibition of PARP-1 by gene deletion increased the AOM/DSS-induced tumor burden when combined with amplified DNA damage via deletion of the DNA repair gene $O^6$-methylguanine-DNA methyltransferase (18). In addition to enhancing the effects of immunotherapy, PARPi may mitigate colitis or cachexia, which are prominent side effects of immunotherapy and cancer in general, respectively. Our observation of the effect of olaparib on cachexia is consistent with a recent study that showed that in a diaphragm and gastrocnemius model of lung cancer with the LP07 adenocarcinoma cell line, PARP-1 (and PARP-2) gene knockout partially protected against cachexia (27).

In conclusion, our results will provide extraordinary opportunities for immediate clinical trials. Without wishing to be bound by theory, the results of such trials can benefit a large proportion of cancer patients. Our findings highlight the notion that targeting the cancer cell with PARPi should not always be the main goal, as targeting cells of the immune system may allow us to treat additional cancer types in addition to BRCA-mutated breast or ovarian cancer with this therapeutic modality.

Materials and Methods

Animals and Genotyping:

C57BL/6 or BALB/c WT mice and C57BL/6 $APC^{Min/+}$ mice were purchased from Jackson Laboratories (Bar Harbor, Me.) and allowed to acclimate prior to experiments. $PARP-1^{+/-}$ mice were maintained on a C57BL/6 background as described previously (28) and interbred to generate $PARP-1^{-/-}$ mice or crossed with $APC^{Min/+}$ mice to generate $APC^{Min/+}$ $PARP-1^{+/-}$ mice. Male $APC^{Min/+}$ $PARP-1^{+/-}$ were crossed with $PARP-1^{-/-}$ females to generate $APC^{Min/+}$ $PARP-1^{-/-}$ mice. All mice were housed in a specific pathogen-free facility at LSUHSC (New Orleans, La.) in a 12-hour light: 12-hour dark photoperiod with unlimited access to sterilized chow and water. Maintenance, experimental protocols, and procedures were all approved by the LSUHSC Institutional Animal Care and Use Committee (IACUC). The different mouse strains were genotyped using DNA extracted from tail snips according to standard protocols with primer sets specific for PARP-1, APC, or $APC^{Min}$ (IDT, Coralville, Iowa) and recommended by Jackson Laboratories (Supplementary Table S1).

Cell Isolation, Culture, Treatments, RNA Extraction, cDNA Synthesis and Quantitative PCR—

Primary CEC were isolated essentially as described (29). The mouse colon adenocarcinoma (MC-38 or CT-26), Jurkat T, RAW264.7, or 3LL lung carcinoma cell lines were purchased from Kerafast (Boston, Mass.) or ATCC (Manassas, Va.). Mouse embryonic fibroblasts were derived from WT, $PARP-1^{+/-}$, or $PARP-1^{-/-}$ mice using standard protocols. CEC were serum-starved overnight in 0.5% FBS prior to treatment. Treatment with 2 µg/ml LPS (Sigma-Aldrich, St Louis, Mo.) or 10 ng/ml TNF-α (Roche Diagnostics Corp, Indianapolis, Ind., USA) was conducted in starving medium. MC-38 and CT-26 cells were cultured in RPMI medium supplemented with 10% FBS and 1% penicillin/streptomycin, 29.2 mM Hepes, 2 mM L-glutamine, and 0.03 mM β-mercaptoethanol. Jurkat T and 3LL cells were grown in RPMI or DMEM, respectively, supplemented with 10% FBS and antibiotics. At 85-90% confluency, attached cells were trypsinized and suspended in PBS to a final density of $1\times10^6$ cells/ml. For in vitro studies, $0.5-1\times10^6$ cells were seeded for 24 h prior to treatment. Total RNA was extracted using a RNA extraction kit (Qiagen, Valencia, Calif.) according to the manufacturer's instructions. RNA was used to generate cDNA using reverse transcriptase III (Invitrogen, Carlsbad, Calif.). PCR was done using previously validated primer sets (IDT) specific for mouse TNF-α, IL-6, MCP-1, or β-actin (Supplementary Table S1) (30-32). Quantitative determination of gene expression levels using a 2-step cycling protocol was conducted on a MyIQ Cycler (Bio-Rad, Hercules, Calif., USA). Relative expression levels were calculated using the 2[-Delta Delta C(T)] method. Quantities of all targets were normalized to the mouse β-actin gene.

$CD3^+$ T cells were isolated from spleens of naive WT mice using MagniSort Mouse T-cell Enrichment Kit (eBioscience, San Diego, USA) according to the manufacturer's instructions. The Purity of the enriched T-cells was tested by FACS analysis using antibody to mouse CD3 (BD, Franklin Lakes, N.J.). Bone marrow-MDSCs were generated by incubating bone marrow cells with a cocktail of either 20 or 40 ng/ml of GM-CSF, G-CSF, and IL-6. For tumor MDSCs, MC-38-engrafted tumors were harvested and digested with liberase (Roche) and DNase I (Sigma-Aldrich) solution for 45 minutes at 37° C. Myeloid cells were then isolated using EasySep Mouse CD11b Positive Selection Kit (Stem Cell, Vancouver, Canada); purity of MDSCs was assessed by FACS analysis with antibodies to mouse CD11b (eBioscience) and Gr-1 (BD, Franklin Lakes, N.J.). To conduct the suppression assay, T cells, tumor- or bone marrow-derived MDSCs were co-cultured with T cells labeled with carboxyfluorescein diacetate succinimidyl ester (CFSE) (Life Technologies, Carlsbad, Calif.) at a ratio of 1:8. The co-culture was conducted in plates that were pre-coated, overnight, with 1 µg/ml of CD3 (clone 145-2C11) and CD28 (clone; 37.51) (BD, Franklin lakes, USA). T cell proliferation was assessed 72 h later by FACS.

Tumor Models, Assessment of Tumor Burden and Adoptive Transfer—

For the azoxymethane/Dextran Sulfate Sodium (AOM/DSS)-induced tumorigenesis model, six to eight weeks old WT, $PARP-1^{+/-}$ or $PARP-1^{-/-}$ mice received a single dose (10 mg/kg) of AOM, i.p., followed by 4 cycles of 1.25% DSS provided in drinking water. Each cycle consisted of a week of DSS water separated by 2 weeks of regular water. In some experiments, AOM/DSS-treated WT mice were administered, i.p., 5 or 25 mg/kg (Selleckchem, TX) of olaparib or vehicle twice a week starting at week 2 until the end of the protocol. At week 22 after the start of the experimental protocol, mice were sacrificed by $CO_2$ asphyxiation. Colons, spleens, and blood were collected for analysis. Colons were opened longitudinally and washed with PBS to assess the tumor burdens using a dissecting microscope. For the $APC^{Min}$-mediated model, $APC^{Min/+}$, $APC^{Min/+}$ $PARP^{-/-}$, or $APC^{Min/+}$ $PARP-1^{-/-}$ male mice were sacrificed at 16 weeks of age. Some $APC^{Min/+}$ mice received i.p injections of olaparib starting at week 6 for 10 weeks. Sacrificed mice were processed as described above except that the tumor burden was assessed along the whole intestinal track. Tumors were counted and divided in groups lower than 2 mm, 2-4 mm, and tumors bigger than 4 mm in diameter.

For the syngeneic tumor models, six to eight weeks old WT, $PARP-1^{+/-}$, or $PARP-1^{-/-}$ mice were subcutaneously inoculated with $2.5 \times 10^5$ MC-38 cells. In some experiments, MC-38 cells transfected with p193-PGK-SB100X and $pKT_2PGK$-BsdGFP_CLP-Luc plasmids (flanked by Sleeping Beauty transposons) and sorted by FACS. Selected cells were then engrafted onto mice as described above. When tumors became palpable (at day 4-6), WT mice were randomized and assigned to the different experimental groups. Some WT mice received i.p injections of olaparib in doses of 0.2, 5, or 25 mg/kg three times per week and others received i.p. anti-mouse PD-1 (CD279) antibodies (100 μg/mouse) or isotype control (BioXCell, NH, USA) twice per week. Tumor volumes were measured with a digital caliper or assessed using GFP/Luc-Biophotonic Imaging (Xenogen IVIS200, PerkinElmer, Boston, Mass.). Tumors were measured by the greatest longitudinal diameter (length) and the greatest transverse diameter (width) using a digital caliper. Tumor volumes were calculated using the following formula: tumor volume=(length×width$^2$)/2. For luciferase imaging, tumor-bearing mice received 150 mg/kg of D-luciferin potassium salt solution (PerkinElmer, Boston, Mass.) i.p. five minutes prior to anesthetic induction and imaging. Bioluminescence within a predetermined region of interest (ROI) on each mouse was quantified in photons/sec/cm$^2$/sr. At the end of the protocol (day 20-24), mice were sacrificed and tumors were harvested for further processing and analysis. For the adoptive transfer experiments, $3 \times 10^6$ BM-MDSCs derived from WT mice or vehicle were injected, intratumorally, into WT or $PARP-1^{+/-}$ mice. The MDSCs were delivered at five injection sites at days 8 and 16 following engraftment of MC-38 cells.

Tissue Processing, Immunohistochemistry, Immunofluorescence and Cytokines Measurement—

Some tissues were fixed in buffered formalin (10%), paraffin-embedded, then sectioned. Serial sections were subjected to H&E staining, immunohistochemistry (IHC) or immunofluorescence, as described (33), with antibodies to PCNA (Novusbio, Littleton, Colo.), COX-2 (Santa Cruz Biotechnology, Santa Cruz, Calif.), ICAM-1 (Santa Cruz Biotechnology), CD8 (Santa Cruz Biotechnology), or Gr1 (eBioscience, San Diego, USA) as previously described (34). Some of the sections were subjected to immunofluorescence with antibodies to CD8 or Gr1. Blood, collected by cardiac puncture, was run through a Microtainer Serum Separator tube (BD, Franklin Lake, NJ). The collected sera were immediately stored at −80° C. for future use and analysis. Cytokine levels were assessed for TNF-α (ELM-TNFα-1), IL-6 (ELM-IL-6-1), and MCP-1 (ELM-MCP1) by ELISA (all from RayBiotech, Norcross, Ga.) according to the manufacturer's instructions and recommendations.

Cell Fractionation, Protein Extraction and Immunoblot Analysis—

Tumor tissues or cells were harvested and homogenized in RIPA lysis buffer (Santa Cruz Biotechnology) containing a cocktail of protease and phosphatase inhibitors on ice. Nuclear fractions were isolated as described (35) and the remaining chromatin pellets were washed then suspended in an isotonic buffer followed by sonication. Protein extracts were subjected to immunoblot analysis essentially as described (9) with antibodies against PARP-1 (1:1000, MA5-15031, Invitrogen), cleaved (p85) PARP-1 (1:1000, 9541, Cell Signaling), cleaved caspase-3 (1:1000, 9664, Cell Signaling), cleaved caspase-7 (1:1000, 9491, Cell Signaling), ARG1 (1:1000, 610708, BD), COX-2 (1:1000, 4842, Cell Signaling), p53 (FL-393) (1:1000, sc-6243, Santa Cruz Biotechnology), phospho-(S15) p53 (1:1000, 9284, Cell Signaling), phospho-(S37) p53 (1:1000, 9289, Cell Signaling), STAT3 (1:1000, 9132, Cell Signaling), phospho-(Y705) STAT3 (1:1000, 9131, Cell Signaling), γH2AX (1:1000, H5912, Sigma-Aldrich), Anti-GRB2 (1:1000, 610112, BD), PD-L1 (1:1000, 66248, Proteintech), cleaved caspase 9 (Asp315) (1:1000, 9505, Cell Signaling), caspase 8 (1C12) (1:1000, 9746, Cell Signaling), p21/Waf1/Cip1 (1:1000, 2946, Cell Signaling), PAR (1:1000, 4335, Trevigen), GAPDH (G-9) (1:1000, sc-365062, Santa Cruz Biotechnology), Histone 3 (H3) (1:1000, D2B12, Cell Signaling), tubulin (1:1000, 3873, Cell Signaling), actin (C-2) (1:1000, sc-8432, Santa Cruz Biotechnology); the last four antibodies were used to detect control proteins. Protein expression signals developed by ECL (Pierce, ThermoFisher Scientific) were determined by a G: Box Gel Image Analysis System (Syngene, Cambridge, UK) equipped with the GeneSys image capture software.

Flow Cytometric Characterization of Tumor Infiltrating Immune Cells Using Fluorescence-Activated Cell Sorting (FACS) Analysis—

Following digestion, tumor homogenates were filtered through a 70 μM cell strainer to obtain a single cell suspension. Cell suspensions were then subjected to red blood cell lysis using ACK buffer for 5 minutes before resuspending in complete media. Cells were treated with anti-CD16/CD32 (BD; 2.4G2) for Fc blocking prior to staining with fluorescently-labeled mouse antibodies specific for CD45 (30-F11), CD3e (500A2) (both from eBioscience, San Diego, Calif.), Ly6C (AL-21), Ly6G (1A8), Gr1 (RB6-8C5), CD11b (M1/70), CD8 (53-6.7), and PD-1 (PA5-J43) (all from BD Biosciences, San Jose, Calif.). Single cells were gated by first using forward- and side-scatter doublet discrimination. Immune cells were discriminated from this doublet-excluded population using CD45. Myeloid cells were identified using a CD11b$^+$ gate and MDSC subtypes identified by Gr1 selection and then plotted Ly6G/Ly6C. CD3$^+$ T-cells were gated from CD45$^+$ cells. CD4+ and C8$^+$ T-cells were identified from CD3$^+$ gate. The detailed gating strategy is described in FIG. 45.

Statistical Analysis—

All data are presented as mean±standard error of mean (SEM). Analysis of the variance for the different groups (same experiment) was conducted using a one-way ANOVA followed by Tukey's multiple comparison test. When a comparison is conducted between two groups, an unpaired Student t-test was used. These analyses were facilitated by the PRISM software (GraphPad, San Diego, Calif.).

REFERENCES CITED IN THIS EXAMPLE

1. C. Gourley et al., Moving From Poly (ADP-Ribose) Polymerase Inhibition to Targeting DNA Repair and DNA Damage Response in Cancer Therapy. *J Clin Oncol,* JCO1802050 (2019).
2. T. A. Hopkins et al., PARP1 Trapping by PARP Inhibitors Drives Cytotoxicity in Both Cancer Cells and Healthy Bone Marrow. *Mol Cancer Res* 17, 409-419 (2019).
3. E. X. Chen et al., A Phase I study of olaparib and irinotecan in patients with colorectal cancer: Canadian Cancer Trials Group IND 187. *Invest New Drugs* 34, 450-457 (2016).
4. L. Leichman et al., Phase II Study of Olaparib (AZD-2281) After Standard Systemic Therapies for Disseminated Colorectal Cancer. *Oncologist* 21, 172-177 (2016).
5. A. Claybon, B. Karia, C. Bruce, A. J. Bishop, PARP1 suppresses homologous recombination events in mice in vivo. *Nucleic Acids Res* 38, 7538-7545 (2010).
6. Z. Q. Wang et al., Mice lacking ADPRT and poly(ADP-ribosyl)ation develop normally but are susceptible to skin disease. *Genes & Development* 9, 509-520 (1995).
7. M. Oumouna et al., Poly(ADP-ribose) polymerase-1 inhibition prevents eosinophil recruitment by modulating Th2 cytokines in a murine model of allergic airway inflammation: a potential specific effect on IL-5. *J Immunol* 177, 6489-6496 (2006).
8. K. Oumouna-Benachour et al., Poly(ADP-ribose) polymerase inhibition reduces atherosclerotic plaque size and promotes factors of plaque stability in apolipoprotein E-deficient mice: effects on macrophage recruitment, nuclear factor-kappaB nuclear translocation, and foam cell death. *Circulation* 115, 2442-2450 (2007).
9. M. A. Ghonim et al., PARP is activated in human asthma and its inhibition by olaparib blocks house dust mite-induced disease in mice. *Clin Sci (Lond)* 129, 951-962 (2015).
10. N. A. Berger et al., Opportunities for the repurposing of PARP inhibitors for the therapy of non-oncological diseases. *Br J Pharmacol,* (2017).
11. T. Nozaki et al., Parp-1 deficiency implicated in colon and liver tumorigenesis induced by azoxymethane. *Cancer Sci* 94, 497-500 (2003).
12. D. I. Gabrilovich, Myeloid-Derived Suppressor Cells. *Cancer Immunol Res* 5, 3-8 (2017).
13. V. Bronte et al., Recommendations for myeloid-derived suppressor cell nomenclature and characterization standards. *Nat Commun* 7, 12150 (2016).
14. S. Benzekry et al., Metronomic reloaded: Theoretical models bringing chemotherapy into the era of precision medicine. *Semin Cancer Biol* 35, 53-61 (2015).
15. A. G. Dalgleish, P. L. Stern, The failure of radical treatments to cure cancer: can less deliver more? *Ther Adv Vaccines Immunother* 6, 69-76 (2018).
16. J. M. de Murcia et al., Requirement of poly(ADP-ribose) polymerase in recovery from DNA damage in mice and in cells. *Proc Natl Acad Sci USA* 94, 7303-7307 (1997).
17. A. J. Snider et al., Murine Model for Colitis-Associated Cancer of the Colon. *Methods Mol Biol* 1438, 245-254 (2016).
18. B. Dorsam et al., PARP-1 protects against colorectal tumor induction, but promotes inflammation-driven colorectal tumor progression. *Proc Natl Acad Sci USA* 115, E4061-E4070 (2018).
19. C. B. Larmonier et al., Transcriptional Reprogramming and Resistance to Colonic Mucosal Injury in Poly(ADP-ribose) Polymerase 1 (PARP1)-deficient Mice. *J Biol Chem* 291, 8918-8930 (2016).
20. K. T. Velazquez et al., Quercetin Supplementation Attenuates the Progression of Cancer Cachexia in Apc (Min/+) Mice. *Journal of Nutrition* 144, 868-875 (2014).
21. P. Darvin, S. M. Toor, V. Sasidharan Nair, E. Elkord, Immune checkpoint inhibitors: recent progress and potential biomarkers. *Exp Mol Med* 50, 165 (2018).
22. J. Sceneay et al., Tracking the fate of adoptively transferred myeloid-derived suppressor cells in the primary breast tumor microenvironment. *PLoS One* 13, e0196040 (2018).
23. T. Condamine, J. Mastio, D. I. Gabrilovich, Transcriptional regulation of myeloid-derived suppressor cells. *J Leukoc Biol* 98, 913-922 (2015).
24. A. Marchetti, A. Di Lorito, F. Buttitta, Why anti-PD1/PDL1 therapy is so effective? Another piece in the puzzle. *J Thorac Dis* 9, 4863-4866 (2017).
25. A. Thomas et al., Durvalumab in Combination with Olaparib in Patients with Relapsed Small Cell Lung Cancer: Results from a Phase II Study. *J Thorac Oncol,* (2019).
26. S. Jiao et al., PARP Inhibitor Upregulates PD-L1 Expression and Enhances Cancer-Associated Immunosuppression. *Clin Cancer Res* 23, 3711-3720 (2017).
27. A. Chacon-Cabrera et al., Role of PARP activity in lung cancer-induced cachexia: Effects on muscle oxidative stress, proteolysis, anabolic markers, and phenotype. *J Cell Physiol* 232, 3744-3761 (2017).
28. M. A. Ghonim et al., PARP inhibition by olaparib or gene knockout blocks asthma-like manifestation in mice by modulating CD4(+) T cell function. *J Transl Med* 13, 225 (2015).
29. K. Oumouna-Benachour et al., Intrinsic resistance to apoptosis of colon epithelial cells is a potential determining factor in the susceptibility of the A/J mouse strain to dimethylhydrazine-induced colon tumorigenesis. *Mol Carcinog* 46, 993-1002 (2007).
30. M. Zerfaoui et al., Poly(ADP-ribose) polymerase-1 is a determining factor in Crm1-mediated nuclear export and retention of p65 NF-kappa B upon TLR4 stimulation. *J Immunol* 185, 1894-1902 (2010).
31. M. Zerfaoui et al., Effects of PARP-1 deficiency on airway inflammatory cell recruitment in response to LPS or TNF: differential effects on CXCR2 ligands and Duffy Antigen Receptor for Chemokines. *J Leukoc Biol* 86, 1385-1392 (2009).
32. M. Zerfaoui et al., Nuclear translocation of p65 NF-kappaB is sufficient for VCAM-1, but not ICAM-1, expression in TNF-stimulated smooth muscle cells: Differential requirement for PARP-1 expression and interaction. *Cell Signal* 20, 186-194 (2008).
33. A. A. Al-Khami et al., Fuelling the mechanisms of asthma: Increased fatty acid oxidation in inflammatory immune cells may represent a novel therapeutic target. *Clin Exp Allergy,* (2017).
34. A. S. Naura et al., Reciprocal regulation of iNOS and PARP-1 during allergen-induced eosinophilia. *Eur Respir J* 33, 252-262 (2009).
35. A. H. Boulares, M. C. Ferran, J. Lucas-Lenard, NF-kappaB activation Is delayed in mouse L929 cells infected with interferon suppressing, but not inducing, vesicular stomatitis virus strains. *Virology* 218, 71-80 (1996).

Supplementary Table 1: PCR Primer Sequences

SUPPLEMENTARY TABLE 1

PCR primer sequences

| Gene | Sequence | SEQ ID NO: |
|---|---|---|
| β-actin | Forward: 5'-TAC AGC TTC ACC ACC ACA GC-3' | 1 |
| | Reverse: 5'-TCT CCA GGG AGG AAG AGG AT-3' | 2 |
| ICAM-1 | Forward: 5'-GTG ATG CTC AGG TAT CCA TCC A-3' | 3 |
| | Reverse: 5'-CAC AGT TCT CAA AGC ACA GCG-3' | 4 |
| iNOS | Forward: 5'-TCT TCG AAA TCC CAC CTG AC-3' | 5 |
| | Reverse: 5'-CCA TGA TGG TCA CAT TCT GC-3' | 6 |
| IL-6 | Forward: 5'-CTG GAA GAG ACT TCC ATC GAG-3' | 7 |
| | Reverse: 5'-AGT GGT ATA GAC AGG TCT GTT GG-3' | 8 |
| TNF-α | Forward: 5'-CAT CTT CTC AAA ATT CGA GTG ACA A-3' | 9 |
| | Reverse: 5'-TGG GAG TAG ACA AGG TAC AAC CC-3' | 10 |
| VCAM-1 | Forward: 5'-TGC CGA GCT AAA TTA CAC ATT G-3' | 11 |
| | Reverse: 5'-CCT TGT GGA GGG ATG TAC AGA-3' | 12 |
| PARP-1 | Forward: 5'-CAT GTT CGA TGG GAA AGT CCC-3' | 13 |
| | Reverse 1: 5'-CCA GCG CAG CTC AGA GAA GCC A-3' | 14 |
| | Reverse 2: 5'-AGG TGA GAT GAC AGG AGA TC-3' | 15 |
| APC | WT: 5'-GCC ATC CCT TCA CGT TAG-3' | 16 |
| | Common antisense: 5'-TTC CAC TTT GGC ATA AGG C-3' | 17 |
| | APC$^{Min}$: 5'-TTC TGA GAA AGA CAG AAG TTA-3' | 18 |

Example 6

Protocol for Anti-PD-Li+PARPi Synergy Experiments:

Six to eight weeks old WT mice will be subcutaneously inoculated with $2.5 \times 10^5$ MC-38 cells (or other cancer models). Mice will be randomized and received i.p injections of olaparib, such as in doses of 0.2, 5, or 25 mg/kg three times per week, and others received i.p. anti-mouse PD-L1 (clone B7-H1) antibodies (such as 100 μg/mouse) or isotype (LTF-2) control (BioXCell, NH, USA) twice per week. Mice may also be treated with anti-EGFR (clone 225) or anti-VGEF-R2 (clone DC101) to examine the synergy between PARP inhibitors with non-check point inhibitor immunotherapy. Tumor volumes will be measured with a digital caliper or assessed using GFP/Luc-Biophotonic Imaging (Xenogen IVIS200, PerkinElmer, Boston, Mass.). Tumors will be measured by the greatest longitudinal diameter (length) and the greatest transverse diameter (width) using a digital caliper. Tumor volumes will be calculated using the following formula: tumor volume=(length×width$^2$)/2. For luciferase imaging, tumor-bearing mice will receive 150 mg/kg of D-luciferin potassium salt solution (PerkinElmer, Boston, Mass.) i.p. five minutes prior to anesthetic induction and imaging. Bioluminescence within a predetermined region of interest (ROI) on each mouse will be quantified in photons/sec/cm$^2$/sr. At the end of the protocol (day 20-24), mice will be sacrificed and tumors were harvested for further processing and analysis.

EQUIVALENTS

Those skilled in the art will recognize, or be able to ascertain, using no more than routine experimentation, numerous equivalents to the specific substances and procedures described herein. Such equivalents are considered to be within the scope of this invention, and are covered by the following claims.

What is claimed is:

1. A dosing regimen for the treatment of cancer in a subject, the dosing regimen comprising administering to a subject a metronomic dose of a PARP inhibitor compound and a therapeutically effective amount of at least one additional anti-cancer agent, wherein the cancer comprises colon cancer or lung cancer, wherein the metronomic dose comprises about 0.2 mg/kg body weight of a PARP inhibitor per day, and wherein the PARP inhibitor compound is:

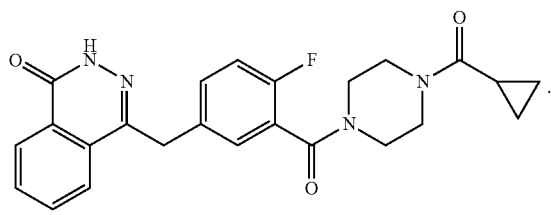 [SMILES: O=C(c1cc(Cc2n[nH]c(=O)c3ccccc23)ccc1F)N1CCN(C(=O)C2CC2)CC1]

2. The dosing regimen of claim 1, wherein the at least one additional anti-cancer agent is administered to the subject every four (4) days, every seven (7) days, every fourteen (14) days, every twenty-one (21) days, or every twenty-eight (28) days.

3. The dosing regimen of claim 1, wherein the at least one additional anti-cancer agent comprises an anti-PD1 antibody or anti-CTLA4 antibody.

4. The method of claim 1, wherein the PARP inhibitor compound inhibits PARP-1, PARP-2, PARP-3, PARP-4, PARP-5a, PARP-5b, PARP-6, PARP-7, PARP-8, PARP-9, PARP-10, PARP-11, PARP-12, PARP-13, PARP-14, PARP-15, PARP-16, or any combination thereof.

5. The method of claim 1, wherein the formation and/or growth of the cancer is exacerbated by chronic inflammation.

6. The method of claim 1, wherein the PARP inhibitor compound is administered as a pharmaceutical composition.

7. The method of claim 6, wherein the pharmaceutical composition further comprises at least one additional anti-cancer agent and/or an anti-inflammatory agent.

8. The method of claim 1, wherein the PARP inhibitor compound is administered orally, intraperitoneally, subcutaneously, intravenously, or intramuscularly.

* * * * *